US012781268B2

(12) United States Patent
Yu et al.

(10) Patent No.: US 12,781,268 B2
(45) Date of Patent: Nov. 3, 2026

(54) ROOM TEMPERATURE NUCLEIC ACID AMPLIFICATION REACTION

(71) Applicant: GenDx Biotech Co., Ltd, Suzhou (CN)

(72) Inventors: Jibin Yu, Suzhou (CN); Jun Li, Suzhou (CN); Chencui Ma, Suzhou (CN); Shanshan Gao, Suzhou (CN)

(73) Assignee: GenDx Biotech Co., Ltd, Suzhou (CN)

( * ) Notice: Subject to any disclaimer, the term of this patent is extended or adjusted under 35 U.S.C. 154(b) by 1011 days.

(21) Appl. No.: 17/601,381

(22) PCT Filed: Jun. 10, 2019

(86) PCT No.: PCT/CN2019/090586
§ 371 (c)(1),
(2) Date: Oct. 4, 2021

(87) PCT Pub. No.: WO2020/199342
PCT Pub. Date: Oct. 8, 2020

(65) Prior Publication Data

US 2023/0029069 A1 Jan. 26, 2023

(30) Foreign Application Priority Data

Apr. 2, 2019 (CN) ........................ 201910262085.3

(51) Int. Cl.
*C12N 9/12* (2006.01)
*C07K 14/005* (2006.01)
*C12Q 1/6844* (2018.01)

(52) U.S. Cl.
CPC .......... *C12Q 1/6844* (2013.01); *C07K 14/005* (2013.01); *C12N 2795/00022* (2013.01)

(58) Field of Classification Search
None
See application file for complete search history.

(56) References Cited

U.S. PATENT DOCUMENTS 8,071,308 B2 * 12/2011 Piepenburg .......... C12N 9/1241
435/6.12

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Franceus et al., J. Ind. Microbiol. Biotechnol. vol. 44, pp. 687-695, 2017.*
Uniprot Accession No. A0A0A7HB46, May 2019.*
Singh et al. (Curr. Protein Pept. Sci. 18:1-11, 2017).*
Zhang et al. (Structure 26:1474-1485, 2018).*

* cited by examiner

*Primary Examiner* — Richard G Hutson
(74) *Attorney, Agent, or Firm* — MUNCY, GEISSLER, OLDS & LOWE, P.C.

(57) ABSTRACT

The present invention provides an application of a cold-active bacteriophage protein in a room temperature nucleic acid amplification reaction; the cold-active bacteriophage is selected from vB_EcoM-VR5, vB_EcoM-VR7, and vB_EcoM-VR20,vB_EcoM-VR25, or vB_EcoM-VR26, and the cold-active bacteriophage protein is a uvsX protein, a uvsY protein and a gp32 protein and/or a variant protein having corresponding functions. Preferably, the uvsX protein and the variant protein thereof are selected from any sequence of SEQ ID Nos. 1-23 or 30, the uvsY protein and the variant protein thereof are selected from any sequence of SEQ ID Nos.27-29 or 32, and the gp32 protein and the variant protein thereof are selected from any sequence of SEQ ID Nos.24-26 or 31. The present invention further provides a room temperature nucleic acid amplification reaction system containing the cold-active bacteriophage protein.

9 Claims, 10 Drawing Sheets

Specification includes a Sequence Listing.

ROOM TEMPERATURE NUCLEIC ACID AMPLIFICATION REACTION

TECHNICAL FIELD

The present invention belongs to the field of biotechnology, and particularly relates to an enzyme having low-temperature activity and an application thereof for nucleic acid amplification reaction under an in vitro low temperature condition.

SEQUENCE LISTING

The instant application contains a Sequence Listing which has been submitted electronically in ASCII format and is hereby incorporated by reference in its entirety. Said ASCII copy, created on Sep. 25, 2021, is named Untitled_WorkFile2.TXT and is 33,771 bytes in size. Applicant hereby states that the submission, filed in accordance with 37 CFR 1.821(e), herein does not include new matter.

BACKGROUND

In vitro nucleic acid amplification is a very important technology in the field of modern life science. Since 1990, in vitro nucleic acid amplification technology has achieved rapid growth.

Moreover, the technical field further plays an increasingly important role in future life science field.

The early diagnosis of lots of human and animal diseases may be performed by nucleic acid technology, which relies on an effective in vitro nucleic acid amplification technology.

Polymerase chain reaction (PCR) is a classic in vitro nucleic acid amplification method. PCR has been put in use for more than 30 years since its naissance, and various kinds of nucleic acid testing methods having different functions have been derived on the basis of PCR, such as, Reverse Transcript PCR (RT-PCR), Quantitative PCR (qPCR), and nested-PCR. PCR reaction is as follows: double-stranded DNA is cracked into single strands under high temperature conditions, then cooled and annealed; a primer is paired with a template strand, and finally, the primer is extended at a condition of 72° C., and the above process is recycled and DNA shows exponential amplification. PCR reaction process needs to be done in an apparatus having a precise temperature control element, but such an apparatus is very expensive and requires operating personnel to possess very complicated professional skill. Therefore, the apparatus may be only provided in the laboratory or medical institution from some developed regions, which greatly limits the popularization and application of PCR-based molecular diagnostic technique. In consideration of the limitations in conventional PCR from instrument and equipment, electric power and other factors, in recent years, isothermal DNA amplification has been springing up quietly, such as, strand displacement amplification (SDA), helicase dependent amplification (HDA), nuclear acid sequence-based amplification (NASBA), loop-mediated isothermal amplification (LAMP), rolling circle amplification (RCA), and Recombinase Polymerase Amplification (RPA) [1]. The most widely used is LAMP and RPA, but LAMP and RPA reaction still needs to be performed under a specific temperature (LAMP: 60-65° C., RPA: 37-42° C.). Moreover, the reaction is comparatively sensitive to the change of temperature; the amplification efficiency will greatly reduce or fail to perform correct amplification not at a most suitable temperature.

In early stage, people have carried out in-depth studies on DNA duplication in vivo. Due to a simple structure, T4 bacteriophage will achieve rapid intracellular duplication of its genome DNA after invading into a bacterium. Therefore, predecessors serve T4 bacteriophage as a model organism for a large number of studies in virology and molecular genetics. In 1976, YASUO IMAE, et al., used a bacteriophage lysis solution protein for in vitro replication of T4 bacteriophage DNA [29]; in 1979, Sinha, et al., used T4 bacteriophage duplication-associated proteins (gene proteins 32,41,43,44, 62,45, and 61) to achieve efficient in vitro replication of double-stranded DNA, and the DNA extending rate is almost up to the amplification efficiency of 500 bases/s in vivo [2]. gp32 protein plays a pivotal role in DNA duplication,recombination and repair process of T4 bacteriophage, and the most important reason is that gp32 protein has a property of binding single-stranded DNA tightly [3]. In 1983, *Formosa* et al., immobilized gp32 protein on an agarose adsorption column to perform affinity chromatography on a bacterial lysate infected with T4 bacteriophage, finding that DNA polymerase (gp43 protein) and two important recombinant pathway proteins (uvsX and uvsYproteins) in T4 bacteriophage may specifically bind to gp32 protein [4]. It has been proved in the further study that uvsX protein has similar functions with recA in *Escherichia coli*, and has DNA-dependent ATPase activity, and may bind to single or double-stranded DNA under in vitro normal saline conditions, and may catalyze pairing with homologous double or single-stranded DNA fragments [5,6]. In the corresponding period, Deborah, et al.,expressed uvsX gene by cloning and recombination, and proved that in the presence of gp32 protein, uvsX protein is ATP-dependent and thus has the activity of replacing single-strand DNA into double-stranded DNA, thereby forming a D-Loop structure, and decomposes the substrate ATP into two products ADP and AMP [7A]. What is different from recA is that uvsX has an ATP catalytic hydrolysis rate 10-20 times of recA, moreover, the catalysate may be AMP+$PP_i$ and ADP+$P_i$, and ATP may be hydrolyzed more thoroughly, but recA catalyzes ATP to produce ADP+$P_i$only [7]. gp32 protein may greatly stimulate uvsX to catalyze the activity of homologous pairing of single-stranded DNA (ssDNA). Meanwhile, uvsX may further bind to uvsY tightly [7], moreover, uvsY may improve the single-stranded DNA dependent ATPase activity by enhancing the affinity between uvsX and ssDNA [8, 9]. The homologous recombination function brought by binding uvsX to ssDNA is closely associated with the duplication process of T4 DNA; after uvsX-ssDNA binds to homologous fragments, ssDNA may serve as a primer for DNA duplication [10]. The above evidences prove that gp32, uvsX and uvsY protein play a very important role in the duplication process of T4 bacteriophage DNA. It has been found in the further study that the uvsY-ssDNA complex formed by uvsY and ssDNA may cause the change of an ssDNA structure, such that ssDNA framework is more inclined to form a uvsX-SSDNA complex. Meanwhile, ATP binding makes the structure of uvsX-ssDNA more stable [11-14]. It has been found in the further study that gp32 protein and single-stranded ssDNA form a stable gp32-ssDNA complex. But under the action of uvsY, the gp32-ssDNA complex structure has an obviously reduced stability, and the ssDNA is more inclined to form a uvsX-ssDNA complex [15].

David A. Zarlinget al. used such a characteristic to perform nucleic acid amplification in a specific segment via *Escherichia coli*RecA protein and SSB protein and by means of a specific primer. Piepenburg made improvements based on this and replaced *Escherichia coli* protein into T4 bacteriophage proteins gp32, uvsX or uvsY; bsu DNA polymerase klenow fragment or sau DNA polymerase klenow fragment is selected as DNA polymerase, and the process was named RPA amplification (recombinase polymerase amplification) [22]. Gp32 protein has a similar function as the SSB protein in bacteria, and may specifically bind an ssDNA oligonucleotide primer to form a Gp32-primer complex, such that the primer maintains a single-stranded structure. Secondly, UvsY and Gp32-primer complex form a UvsY-Gp32-primer complex, and the binding affinity between Gp32 and the primer is reduced, such that UvsX competitively binds to the primer to form a UvsX-primer complex. Thirdly, under the action of ATP, the UvsX-primer complex has the characteristic of homologously pairing with the complementary sites in template strand and replaces the strand with the same base sequence, and then binds to the complementary strand to form a D-loop structure. Fourthly, under the action of DNA polymerase, 3' terminal exposed on the primer in the D-loop structure is extended till the end of duplication. After the above process is recycled, the target DNA fragment may achieve exponential amplification.

It is reported that RPA technology may achieve amplification under the condition of 30° C., but the amplification efficiency reduces sharply. Therefore, to further reduce the reaction temperature, the present patent performs combined screening in vitro of cold-active bacteriophage protein or amino acid mutation screening directed to proteins such as Gp32, UvsX and UvsY, DNA polymerase and creatine kinase, such that the amplification reaction may be performed efficiently at an exponential rate and a lower temperature, thus shortening the amplification time. In this way, rapid amplification may achieved merely in general indoor environment temperature without any temperature-controlled equipment. In combination with a nucleic acid testing method, the present application simplifies the equipment required by the whole nucleic acid amplification and detection and achieves more convenient operation. The scope of media for the reaction is broader, and the amplification reaction may be performed not limited to a heated medium, such as, fiber paper, nylon membrane, nitrocellulose membrane and cotton fiber ball.

SUMMARY OF THE INVENTION

The host of about 90% known T4-related bacteriophage is *Escherichia coli* or other enteric bacilli, and the host of the rest 10% is other bacteria, such as, *Aeromonas, vibrio* or Synechococcus [23]. Most of them are found in domestic sewage or wastewater, and the natural host is human or other animal intestinal tract [24]. Therefore, the optimum growth temperature is similar to the host thereof, namely, 37-40° C. [25]. According to the different optimum culture temperature of forming bacteriophage plaques, the bacteriophage is classified into three categories: more than 25° C. is called high-temperature (HT) bacteriophage, 30° C. below is low-temperature (LT) bacteriophage, and the one forming bacteriophage plaques between 15° C.-42° C. is moderate temperature (MT) bacteriophage [26]. T4 bacteriophage is a kind of typical room temperature bacteriophage.

Laura Kaliniene, et al. have successively found five cold-active bacteriophages, vB_EcoM-VR5, vB_EcoM-VR7 and vB_EcoM-VR20, vB_EcoM-VR25, and vB_EcoM-VR26. Three bacteriophages vB_EcoM-VR5, vB_EcoM-VR7 and vB_EcoM-VR20 were subjected to hemolytic plaque assay respectively at the temperature of 17° C., 24° C., 30° C., 35° C., 37° C., 39° C. and 40° C. according to the method of Seeley and Primrose [27]. The result shows that temperature sensibility of the three bacteriophages is obviously different from T4 bacteriophage, and the efficiency of plating is shown in FIG. 1, and it is determined that the three bacteriophages have an optimum temperature of 24° C. Genome is subjected to sequencing (Enterobacteria phage vB_EcoM_VR5, Accession: KP007359.1; vB_EcoM-VR7, Accession: HM563683.1; vB_EcoM_VR20, Accession: KP007360.1; vB_EcoM_VR25, Accession: KP007361.1; vB_EcoM_VR26, Accession: KP007362.1) to obtain protein sequences associated with DNA duplication.

By comparison with alignX software (as shown in FIG. 3), the protein sequence derived from the cold-active bacteriophage is obviously different from T4 bacteriophage, e.g., the uvsX protein of vB_EcoM-VR5 bacteriophage has only 65.6% homology to T4.

The corresponding DNA sequence is synthesized by reference to the above genome sequence, and cloned onto a pET22b expression vector with double enzyme digestion Nde I and EcoR I, and the expressed proteins are respectively named VR5X_NHis, VR7_25X_NHis, VR20_26X_NHis, VR5G_NHis, VR7G_NHis, VR25G_NHis, VR5Y_NHis, VR7_25_26Y_NHis, VR20Y_NHis, VR7_25X_CHis, VR7G_CHis, VR7_25_26Y_CHis, and the sequences are as follows:

| | |
|---|---|
| VR5X_NHis | Mhhhhhhsdlksrlikastskmtadltksklfngrdevptripmlnialggalnaglqsgl tifaapskhfktlfgltmvaaymkkypdaiclfydsefgasesyfrsmgvdlervvhtpiq sveqlkvdmtnqleeitrgekviifidsigntaskketedalnekvvgdmtrakslkslfri vtpyltikdipcvainhtameiggmypkeimgggtgilysastvffiskrqvkdgteltgy dftlkaeksrtvkekstfpitvnfeggidpfsgllemateigfvvkpkagwynrafldettg emvqeekswrakatdcvefwgplfkhapfraaienkyklgainsikevddavndlinsr vsknvavklsgdaqsaadiendleemdlnd (SEQ ID NO. 21) |
| VR7_25X_NHis | Mhhhhhhsiadlksrlikastskmtatltkskffndkdvvrtkipmlniaisgaldggmq sgltifagpskhfksnmgltmvsaymnkypeaiclfydsefgiteaylramkvdpervi htpiqsveqlkvdmvnqleaiergekviifidsignmaskketedalnekvvgdmtrak slkslfrivtpffsikdipcvavnhtietiemysktvmtggtgvmysadtvfiigkrqiketg kelegfqfvlnaeksrmvkekskffidvkfdggidpysglldmameigfvvkpkvgw ynreyldvetgemvreekswrakdtnctefwgplfkhepfrdaikrhyqlgaidsnavv daevdeliaskvekysapvgktkpsaadiendldmmedlde (SEQ ID NO. 22) |
| VR20_26X_NHis | Mhhhhhhsiadlksrlikastskmtatltkskffndkdvvrtkipmlniaisgaldggmq sgltifagpskhfksnmgltmvsaymnkypeaiclfydsefgiteaylramkvdpervi htpiqsveqlkvdmvnqleaiergekviifidsignmaskketedalnekvvgdmtrak slkslfrivtpffsikdipcvavnhtietiemysktvmtggtgvmysadtvfiigkrqiketg kelegfqfvlnaeksrmvkekskffidvkfdggidpysglldmameigfvvkpkvgw |

-continued

| | |
|---|---|
| | ynreyldvetgemvreekswrakdtnctefwgplfkhepfrdaikrhyqlgaidsnavv<br>daevdelisskvekysapegkskpsaadiendldmmedlde (SEQ ID NO. 23) |
| VR5G_NHis: | Mhhhhhhsmfkrrdpsqlaaqlnalkggssfssddksewklkddngvgtavirflpsk<br>deanpspfvklvnhgfkkngqwyiesctsthgdfdscpvckymnqndsfntnnaeyk<br>lmkrktsfwanilvikdsavpanegkvfkfrfgqkimdkinqmvevdtdigetpidvtc<br>pfdganfvlkskkvgdfknyddskfmnqseipnindeayqaklmeemhdlskllefks<br>fetneakfkkvvgtaalggaaakasaaadkigddldafsadldaydskpstparsttpeps<br>vspsdddglddllagl (SEQ ID NO. 24) |
| VR7G_NHis | Mhhhhhhfkrrpadlaaslnalkggagfssddkkewklkdtdgvgsavirflpskne<br>enpspfiklvnhgfknagqwyienctsthgdyencpvcaymnkndlyntneseyrklk<br>rntsywanilvikdpavpsnegqvfkyrfgkkimdkinqmvevdvdmgetaidvtcp<br>feganfvlkskmvsgyknyddskfmnqseiagindeafqkklwdemsdlnellvfksl<br>eenqkkfskvmgtaalggaaskaaaqadklgadlddfdkdmedftsnkpaksertata<br>pstpepsddglddllagl (SEQ ID NO. 25) |
| VR25G_NHis: | Mhhhhhhsmfkrknpadlaaslnalkggsgfssddkkewklkdtdgvgsavirflpsk<br>neenpspfiklvnhgfknagqwyienctsthgdyencpvcaymnkndlyntneseyr<br>klkrntsywanilvikdpavpsnegqvfkyrfgkkimdkinqmvevdvdmgetaidv<br>tcpfeganfvlkskmvsgyknyddskfmnqseiagindeafqkklwdemsdlnellvf<br>ksleenqkkfskvmgtaalggaaskaaaqadklgadlddfdkdmedftsskpakserta<br>tapstpepsddglddllagl (SEQ ID NO. 26) |
| VR5Y_NHis | mhhhhhhskeieyklesfqdaldedlkidgtrlqyevqnnvllhskwlrlytnckkeimr<br>leiqkktslkkrldfytgrgepgdevcmdqyekselktvmaadssvikidtsiqywallq<br>dfcssaldaikargfnlktmhemrqfeagk (SEQ ID NO. 27) |
| VR7_25_26Y_<br>NHis | mhhhhhhkteieyklevfqdeldadlkidgtqiqyetqnnvllhskwlrlytnckkeimr<br>leiqkktalkkrldhytgrgdpgeevcmdvyekselktvmaadssvlkidtsiqywallq<br>dfcsaaldgvksrsfalkhmleirqfeagk (SEQ ID NO. 28) |
| VR20Y_NHis | mhhhhhhkkeieyklevfqdeldadlkidgtqlqyetqnnvllhskwlrlytnckkeim<br>rleiqkktalkkrldhytgrgdpgeevcmdvyekselktvmaadssvlkidtsiqywall<br>qdfcsaaldgvksrsfalkhmleirqfeagk (SEQ ID NO. 29) |
| VR7_25X_CHis | msiadlksrlikastskmtatltkskffndkdvvrtkipmlniaisgaldggmqsgltifag<br>pskhfksnmgltmvsaymnkypeaiclfydsefgiteaylramkvdpervihtpiqsve<br>qlkvdmvnqleaiergekviifidsignmaskketedalnekvvgdmtrakslkslfrivt<br>pffsikdipcvavnhtietiemysktvmtggtgvmysadtvfiigkrqiketgkelegfqf<br>vlnaeksrmvkekskffidvkfdggidpysglldmameigfvvkpkvgwynreyldv<br>etgemvreekswrakdtnctefwgplfkhepfrdaikrhyqlgaidsnavvdaevdeli<br>askvekysapvgktkpsaadiendldmmedldehhhhhh (SEQ ID NO. 30) |
| VR7G_CHis | Mfkrrnpadlaaslnalkggagfssddkkewklkdtdgvgsavirflpskneenpspfi<br>klvnhgfknagqwyienctsthgdyencpvcaymnkndlyntneseyrklkrntsyw<br>anilvikdpavpsnegqvfkyrfgkkimdkinqmvevdvdmgetaidvtcpfeganf<br>vlkskmvsgyknyddskfmnqseiagindeafqkklwdemsdlnellvfksleenqk<br>kfskvmgtaalggaaskaaaqadklgadlddfdkdmedftsnkpaksertatapstpep<br>sddglddllaglhhhhhh (SEQ ID NO. 31) |
| VR7_25_26Y_<br>CHis | mkteieyklevfqdeldadlkidgtqiqyetqnnvllhskwlrlytnckkeimrleiqkkt<br>alkkrldhytgrgdpgeevcmdvyekselktvmaadssvlkidtsiqywallqdfcsaal<br>dgvksrsfalkhmleirqfeagkhhhhhh (SEQ ID NO. 32) |

Meanwhile, the corresponding genes uvsX, uvsY and gp32 of T4 bacteriophage are synthesized, and cloned onto an expression vector pET22b by molecular biology. The expressed amino acid sequence is as follows:

| | |
|---|---|
| Phage_T4_uvsX | MHHHHHHSDLKSRLIKASTSKLTAELTASKFFNEKDVVRT<br>KIPMMNIALSGEITGGMQSGLLILAGPSKSFKSNFGLTMVS<br>SYMRQYPDAVCLFYDSEFGITPAYLRSMGVDPERVIHTPVQ<br>SLEQLRIDMVNQLDAIERGEKVVVFIDSLGNLASKKETED<br>ALNEKVVSDMTRAKTMKSLFRIVTPYFSTKNIPCIAINHTY<br>ETQEMFSKTVMGGGTGPMYSADTVFIIGKRQIKDGSDLQG<br>YQFVLNVEKSRTVKEKSKFFIDVKFDGGIDPYSGLLDMAL<br>ELGFVVKPKNGWYAREFLDEETGEMIREEKSWRAKDTNC<br>TTFWGPLFKHQPFRDAIKRAYQLGAIDSNEIVEAEVDELIN<br>SKVEKFKSPESKSKSAADLETDLEQLSDMEEFNE (SEQ ID<br>NO. 33) |
| Phage_T4_uvsY | MHHHHHHRLEDLQEELKKDVFIDSTKLQYEAANNVMLYS<br>KWLNKHSSIKKEMLRIEAQKKVALKARLDYYSGRGDGDE<br>FSMDRYEKSEMKTVLSADKDVLKVDTSLQYWGILLDFCS<br>GALDAIKSRGFAIKHIQDMRAFEAGK (SEQ ID NO. 34) |

-continued

| | |
|---|---|
| Phage_T4_GP32 | MHHHHHHFKRKSTAELAAQMAKLNGNKGFSSEDKGEWK<br>LKLDNAGNGQAVIRFLPSKNDEQAPFAILVNHGFKKNGK<br>WYIETCSSTHGDYDSCPVCQYISKNDLYNTDNKEYSLVKR<br>KTSYWANILVVKDPAAPENEGKVFKYRFGKKIWDKINAMI<br>AVDVEMGETPVDVTCPWEGANFVLKVKQVSGFSNYDES<br>KFLNQSAIPNIDDESFQKELFEQMVDLSEMTSKDKFKSFEE<br>LNTKFGQVMGTAVMGGAAATAAKKADKVADDLDAFNVD<br>DFNTKTEDDFMSSSSGSSSSADDTDLDDLLNDL (SEQ ID<br>NO. 35) |

A host cell BL21(DE3) is transformed according to molecular cloning technique, and induced with IPTG for expression, then repeatedly frozen and lyzed, and purified [28] by a Ni column to obtain a high-purity protein, and the high-purity protein is subjected to amplification test.

UvsX function is similar to the RecA protein of *Escherichia coli*, and its homologous strand transferase displacement transferase activity is dependent on ATP. Different from RecA, uvsX decomposes ATP into two products of ADP and AMP. High-concentration ADP and AMP will produce an inhibiting effect on uvsX [31]. Therefore, the product needs to be transformed into ATP, thus reducing inhibition. The energy system is formulated by reference to Hinton, D. M, Birkenkamp-Demtroder and other methods, and ATP has a concentration of 1 mM-5 mM, phosphocreatine and myokinase [32, 33]. Myokinase may be selected from rabbit myokinase and carp myokinase. Myokinase M1 type (M1-CK) has adapted to low-temperature environment and PH value with body temperature. Wu CL, et al. have found that Gly in the 268th position of rabbit myokinase is changed into Asnmyokinase to significantly enhance the the activity of myokinase to form ATP under catalysis at low temperature. Therefore, myokinase is theoretically and preferably selected from G268N variant-type myokinase or carp myokinase [34,35].

The genes are synthesized respectively by reference to the protein sequences NCBI No. AAC96092.1 and NP_001075708.1, and respectively cloned onto a pET22b expression vector by double enzyme digestion Nde I and EcoR I; the corresponding proteins are respectively named RM-CK and Carp-M1-CK, and N terminal is fused with a 6xHis tag for the convenience of purification. Meanwhile, by reference to the above literature, the RM-CK encoding gene is mutated by means of a conventional gene site mutation technique, such that G in the position 268 free of histidine-tag) amino acid of the translated protein is mutated to N.

| | |
|---|---|
| RM-CK | Mhhhhhhpfgnthnkyklnykseeeypdlskhnnhmakvltpdlykklrdketpsgftl<br>ddviqtgvdnpghpfimtvgcvagdeesytvfkdlfdpiiqdrhggfkptdkhktdlnhen<br>kkggddldphyvlssrvrtgrsikgytlpphcsrgerraveklsvealnsltgefkgkyyplk<br>smteqeqqqliddhflfdkpvsplllasgmardwpdargiwhndnksflvwvneedhlr<br>vismekggnmkevfrrfcvglqkieeifkka**G**hpfmwnehlgyvltcpsnlgtglrggvh<br>vklahlskhpkfeeiltrlrlqkrgtggvdtaavgsvfdisnadrlgsseveqvqlvvdgvkl<br>mvemekklekgqsiddmipaqk (SEQ ID NO. 36) |
| RM-CK_G268N | Mhhhhhhpfgnthnkyklnykseeeypdlskhnnhmakvltpdlykklrdketpsgftl<br>ddviqtgvdnpghpfimtvgcvagdeesytvfkdlfdpiiqdrhggfkptdkhktdlnhen<br>lkggddldphyvlssrvrtgrsikgytlpphcsrgerraveklsvealnsltgefkgkyyplk<br>smteqeqqqliddhflfdkpvsplllasgmardwpdargiwhndnksflvwvneedhlr<br>vismekggnmkevfrrfcvglqkieeifkka***N***hpfmwnehlgyvltcpsnlgtglrggvh<br>vklahlskhpkfeeiltrlrlqkrgtggvdtaavgsvfdisnadrlgsseveqvqlvvdgvkl<br>mvemekklekgqsiddmipaqk (SEQ ID NO. 37) |
| Carp-M1-CK | mhhhhhhpfgnthnnfklnysvddefpdlakhnnhmakvltkemygklrdkqtstgftl<br>ddaiqtgvdnpghpfimtvgcvagdeesyevfkdlfdpvisdrhggykatdkhktdlnfe<br>nlkggddldpnyvlssrvrtgrsikgyalpphnsrgerraveklsvealnsldgefkgkyyp<br>lksmtdaeqeqliadhflfdkpvsplllaagmardwpdargiwhnenktflvwvneedhl<br>rvismqpggnmkevfrrfcvglqrieeifkkhnhgfmwnehlgfiltcpsnlgtglrggvhv<br>klpklsthakfdeiltrlrlqkrgtggvdtasvggvfdisnadrigssevdqvqcvvdgvklm<br>iemekklekgesidsmipaqk (SEQ ID NO. 38) |

Amplification reaction conditions are referring to the Sinha, N. K. method; Mg2+ concentration is 5-20 mM, K+ concentration is 20-120 mM, preferably, the concentration is 40-80 mM; dNTP concentration is 100 uM-1000 uM; preferably, the concentration is within 300 uM-600 uM.

To further improve the reaction efficiency, it attempts reducing temperature to obtain higher reaction efficiency. By synthesizing DNA directed mutation library and screening, double enzyme digestion Nde I and EcoR I are used for cloning onto a pET22b expression vector, and a plurality of protein variants having in vitro amplification activity are obtained after expression and purification; these variant proteins are respectively named VRX_Variant1, VRX_Variant2 . . . . . . numbered consecutively to VRX_Variant20. The expressed amino acid sequences are respectively as follows:

| | |
|---|---|
| VRX_<br>Variant 1 | Mhhhhhhsdlksrlikastskmtadltksklfngrdevptripmlnialggalnaglqsglt<br>ifaapsksfktlfgltmvaaymkkypdaiclfydsefgasesyfrsmgvdlervvhtpiqs<br>veqlkvdmtnqleeitrgekviifidsigntaskketedalnekvvgdmtrakslkslfrivt<br>pyltikdipcvainhtameiggmypkeimgggtgilysastvffiskrqvkdgteltgydf<br>tlkaeksrtvkekstfpitvnfeggidpfsgllemateigfvvkpkagwynrafldettge<br>mvqeekswrakatdcvefwgplfkhapfraaienkyklgainsikevddavndlinsrv<br>sknvavklsgdaqsaadiendleemdlnd (SEQ ID No. 1) |
| VRX_<br>Variant 2 | Mhhhhhhsdlksrlikastskmtadltksklfngrdevptripmlnialggalnaglqsglt<br>ifagpskhfktlfgltmvaaymkkypdaiclfydsefgasesyfrsmgvdlervvhtpiq<br>sveqlkvdmtnqleeitrgekviifidsigntaskketedalnekvvgsmtrakslkslfriv<br>tpyltikdipcvainhtameiggmypkeimgggtgilysastvffiskrqvkdgteltgyd<br>ftlkaeksrtvkekstfpitvnfeggidpfsgllemateigfvvkpkagwynrafldettge<br>mvqeekswrakatdcvefwgplfkhapfraaienkyklgainsikevddavndlinsrv<br>sknvavklsgdaqsaadiendleemdlnd (SEQ ID No. 2) |
| VRX_<br>Variant 3 | mhhhhhhsdlksrlikastskmtadltksklfngrdevptripmlnialggalnaglqsglt<br>ifagpsksfktlfgltmvaaymkkypdaiclfydsefgisesyfrsmgvdlervvhtpiqs<br>veqlkvdmtnqleeitrgekviifidsigntaskketedalnekvvgsmtrakslkslfrivt<br>pyltikdipcvainhtameiggmypkeimgggtgilysastvffiskrqvkdgteltgydf<br>tlkaeksrtvkekstfpitvnfeggidpfsgllemateigfvvkpkagwynrafldettge<br>mvqeekswrakatdcvefwgplfkhapfraaienkyklgainsikevddavndlinsrv<br>sknvavklsgdaqsaadiendleemdlnd (SEQ ID No. 3) |
| VRX_<br>Variant 4 | mhhhhhhsdlksrlikastskmtadltksklfngrdevptripmlnialggalnaglqsglt<br>ifagpskhfktlfgltmvaaymkkypdaiclfydsefgisesyfrsmgvdlervvhtpiqs<br>veqlkvdmtnqleeitrgekviifidsigntaskketedalnekvvgdmtrakslkslfrivt<br>pyltikdipcvainhtameiggmypkeimgggtgilysastvffiskrqvkdgteltgydf<br>tlkaeksrtvkekstfpitvnfeggidpfsgllemateigfvvkpkagwynrafldettge<br>mvqeekswrakatdcvefwgplfkhapfraaienkyklgainsikevddavndlinsrv<br>sknvavklsgdaqsaadiendleemdlnd (SEQ ID No. 4) |
| VRX_<br>Variant 5 | Mhhhhhhsiadlksrlikastskmtatltkskffndkdvvrtkipmlniaisgaldggmq<br>sgltifagpsksfksnmgltmvsaymnkypeaiclfydsefgiteaylramkvdpervih<br>tpiqsveqlkvdmvnqleaiergekviifidsignmaskketedalnekvvgdmtrakt<br>mkslfrivtpffsikdipcvavnhtietiemysktvmtggtgvmysadtvfiigkrqiketg<br>kelegfqfvlnaeksrmvkekskffidvkfdggidpysglldmameigfvvkpkvgw<br>ynreyldvetgemvreekswrakdtnctefwgplfkhepfrdaikrhyqlgaidsnavv<br>daevdeliaskvekysapvgktkpsaadiendldmmedlde (SEQ ID No. 5) |
| VRX_<br>Variant 6 | mhhhhhhsiadlksrlikastskmtatltkskffndkdvvrtkipmlniaisgaldggmqs<br>gltifagpskhfksnmgltmvsaymnkypeaiclfydsefgiteaylramkvdperviht<br>piqsveqlkvdmvnqleaiergekviifidsignmaskketedalnekvvgdmtraktm<br>kslfrivtpffsikdipcvavnhtietiemysktvmtggtgvmysadtvfiigkrqiketgk<br>elegfqfvlnaeksrmvkekskffidvkfdggidpysglldmameigfvvkpkvgwy<br>nreyldvetgemvreekswrakdtnctefwgplfkhepfrdaikrhyqlgaidsnavvd<br>aevdeliaskvekysapegktkpsaadiendldmmedlde (SEQ ID No. 6) |
| VRX_Var<br>7 | mhhhhhhsiadlksrlikastskmtatltkskffndkdvvrtkipmlniaisgaldgg<br>mqsgltifagpsksfksnmgltmvsaymnkypeaiclfydsefgiteaylramkvdper<br>vihtpiqsveqlkvdmvnqleaiergekviifidsignmaskketedalnekvvgdmtra<br>ktmkslfrivtpffsikdipcvavnhtietiemysktvmtggtgvmysadtvfiigkrqike<br>tgkelegfqfvlnaeksrmvkekskffidvkfdggidpysglldmameigfvvkpkvg<br>wynreyldvetgemvreekswrakdtnctefwgplfkhepfrdaikrhyqlgaidsnev<br>vdaevdeliaskvekysapvgktkpsaadiendldmmedlde (SEQ ID No. 7) |
| VRX_<br>Variant 8 | mhhhhhhsiadlksrlikastskmtatltkskffndkdvvrtkipmlniaisgaldgg<br>mqsgltifagpskhfksnmgltmvsaymnkypeaiclfydsefgiteaylramkvdpe<br>rvihtpiqsveqlkvdmvnqleaiergekviifidsignmaskketedalnekvvsdmtr<br>aktmkslfrivtpffsikdipcvavnhtietiemysktvmtggtgvmysadtvfiigkrqik<br>etgkelegfqfvlnaeksrmvkekskffidvkfdggidpysglldmameigfvvkpkv<br>gwynreyldvetgemvreekswrakdtnctefwgplfkhepfrdaikrhyqlgaidsne<br>vvdaevdeliaskvekysapegktkpsaadiendldmmedlde (SEQ ID No. 8) |
| VRX_<br>Variant 9 | mhhhhhhsiadlksrlikastskmtatltkskffndkdvvrtkipmlniaisgaldgg<br>mqsgltifagpsksfksnmgltmvsaymnkypeaiclfydsefgiteaylramkvdper<br>vihtpiqsveqlkvdmvnqleaiergekviifidsignmaskketedalnekvvgdmtra<br>kslkslfrivtpffsikdipcvavnhtietiemysktvmtggtgvmysadtvfiigkrqiket<br>gkelegfqfvlnaeksrmvkekskffidvkfdggidpysglldmameigfvvkpkvg<br>wynreyldvetgemvreekswrakdtnctefwgplfkhepfrdaikrhyqlgaidsnav<br>vdaevdelisskvekysapegkskpsaadiendldmmedlde (SEQ ID No. 9) |
| VRX_<br>Variant 10 | mhhhhhhsiadlksrlikastskmtatltkskffndkdvvrtkipmlniaisgaldgg<br>mqsgltifagpskhfksnmgltmvsaymnkypeaiclfydsefgiteaylramkvdpe<br>rvihtpiqsveqlkvdmvnqleaiergekviifidsignmaskketedalnekvvsdmtr<br>akslkslfrivtpffsikdipcvavnhtietiemysktvmtggtgvmysadtvfiigkrqik<br>etgkelegfqfvlnaeksrmvkekskffidvkfdggidpysglldmameigfvvkpkv<br>gwynreyldvetgemvreekswrakdtnctefwgplfkhepfrdaikrhyqlgaidsna<br>vvdaevdelisskvekysapegkskpsaadiendldmmedlde (SEQ ID No.<br>10) |

-continued

VRX_ Variant 11
mhhhhhhsiadlksrlikastskmtatltkskffndkdvvrtkipmlniaisgaldggmqs
gltifagpsksfksnmgltmvsaymnkypeaiclfydsefgiteaylramkvdperviht
piqsveqlkvdmvnqleaiergekviifidsignmaskketedalnekvvsdmtraktm
kslfrivtpffsikdipcvavnhtietiemysktvmtggtgvmysadtvfiigkrqiketgk
elegfqfvlnaeksrmvkekskffidvkfdggidpysglldmameigfvvkpkvgwy
nreyldvetgemvreekswrakdtnctefwgplfkhepfrdaikrhyqlgaidsnavvd
aevdelisskvekysapegkskpsaadiendldmmedlde (SEQ ID No. 11)

VRX_ Variant 12
mhhhhhhsiadlksrlikastskmtatltkskffndkdvvrtkipmlniaisgaldggmqs
gltifagpskhfksnmgltmvsaymnkypeaiclfydsefgiteaylramkvdperviht
piqsveqlkvdmvnqleaiergekviifidsignmaskketedalnekvvsdmtraktm
kslfrivtpffsikdipcvavnhtietiemysktvmtggtgvmysadtvfiigkrqiketgk
elegfqfvlnaeksrmvkekskffidvkfdggidpysglldmameigfvvkpkvgwy
nreyldvetgemvreekswrakdtnctefwgplfkhepfrdaikrhyqlgaidsnevvd
aevdelisskvekysapegkskpsaadiendldmmedlde (SEQ ID No. 12)

VRX_ Variant 13
mhhhhhhsiadlksrlikastskmtatltkskffndkdvvrtkipmlniaisgaldggmqs
gltifagpsksfksnmgltmvsaymnkypeaiclfydsefgiteaylramkvdperviht
piqsveqlkvdmvnqleaiergekviifidsignmaskketedalnekvvgdmtraksl
kslfrivtpffsikdipcvavnhtietiemysktvmtggtgvmysadtvfiigkrqiketgk
elegfqfvlnaeksrmvkekskfkidvkfdggidpysglldmameigfvvkpkvgwy
nreyldvetgemvreekswrakdtnctefwgplfkhepfrdaikrhyqlgaidsnavvd
aevdeliaskvekysapvgktkpsaadiendldmmedlde (SEQ ID No. 13)

VRX_ Variant 14
mhhhhhhsiadlksrlikastskmtatltkskffndkdvvrtkipmlniaisgaldggmqs
gltifagpskhfksnmgltmvsaymnkypeaiclfydsefgiteaylramkvdperviht
piqsveqlkvdmvnqleaiergekviifidsignmaskketedalnekvvgdmtraksl
kslfrivtpffsikdipcvavnhtietiemysktvmtggtgvmysadtvfiigkrqiketgk
elegfqfvlnaeksrmvkekskfkidvkfdggidpysglldmameigfvvkpkvgwy
nreyldvetgemvreekswrakdtnctefwgplfkhepfrdaikrhyqlgaidsnavvd
aevdeliaskvekysapvgktkpsaadiendldmmedlde (SEQ ID No. 14)

VRX_ Variant 15
mhhhhhhsiadlksrlikastskmtatltkskffndkdvvrtkipmlniaisgaldggmqs
gltifagpsksfksnmgltmvsaymnkypeaiclfydsefgiteaylramkvdperviht
piqsveqlkvdmvnqleaiergekviifidsignmaskketedalnekvvgdmtraktm
kslfrivtpffsikdipcvavnhtietiemysktvmtggtgvmysadtvfiigkrqiketgk
elegfqfvlnaeksrmvkekskfkidvkfdggidpysglldmameigfvvkpkvgwy
nreyldvetgemvreekswrakdtnctefwgplfkhepfrdaikrhyqlgaidsnevvd
aevdeliaskvekysapvgktkpsaadiendldmmedlde (SEQ ID No. 15)

VRX_ Variant 16
mhhhhhhsiadlksrlikastskmtatltkskffndkdvvrtkipmlniaisgaldggmqs
gltifagpskhfksnmgltmvsaymnkypeaiclfydsefgiteaylramkvdperviht
piqsveqlkvdmvnqleaiergekviifidsignmaskketedalnekvvgdmtraktm
kslfrivtpffsikdipcvavnhtietiemysktvmtggtgvmysadtvfiigkrqiketgk
elegfqfvlnaeksrmvkekskfkidvkfdggidpysglldmameigfvvkpkvgwy
nreyldvetgemvreekswrakdtnctefwgplfkhepfrdaikrhyqlgaidsnevvd
aevdeliaskvekysapvgktkpsaadiendldmmedlde (SEQ ID No. 16)

VRX_ Variant 17
mhhhhhhsiadlksrlikastskmtatltkskffndkdvvrtkipmlniaisgaldggmqs
gltifagpsksfksnmgltmvsaymnkypeaiclfydsefgiteaylramkvdperviht
piqsveqlkvdmvnqleaiergekviifidsignmaskketedalnekvvgdmtraksl
kslfrivtpffsikdipcvavnhtietiemysktvmtggtgvmysadtvfiigkrqiketgk
elegfqfvlnaeksrmvkekskfkidvkfdggidpysglldmameigfvvkpkvgwy
nreyldvetgemvreekswrakdtnctefwgplfkhepfrdaikrhyqlgaidsnavvd
aevdelisskvekysapegkskpsaadiendldmmedldelde (SEQ ID No.
17)

VRX_ Variant 18
mhhhhhhsiadlksrlikastskmtatltkskffndkdvvrtkipmlniaisgaldgg
mqsgltifagpskhfksnmgltmvsaymnkypeaiclfydsefgiteaylramkvdpe
rvihtpiqsveqlkvdmvnqleaiergekviifidsignmaskketedalnekvvsdmtr
akslkslfrivtpffsikdipcvavnhtietiemysktvmtggtgvmysadtvfiigkrqik
etgkelegfqfvlnaeksrmvkekskfkidvkfdggidpysglldmameigfvvkpkv
gwynreyldvetgemvreekswrakdtnctefwgplfkhepfrdaikrhyqlgaidsna
vvdaevdelisskvekysapegkskpsaadiendldmmedldelde (SEQ ID No.
18)

VRX_ Variant 19
mhhhhhhsiadlksrlikastskmtatltkskffndkdvvrtkipmlniaisgaldggmqs
gltifagpsksfksnmgltmvsaymnkypeaiclfydsefgiteaylramkvdperviht
piqsveqlkvdmvnqleaiergekviifidsignmaskketedalnekvvgdmtraktm
kslfrivtpffsikdipcvavnhtietiemysktvmtggtgvmysadtvfiigkrqiketgk
elegfqfvlnaeksrmvkekskfkidvkfdggidpysglldmameigfvvkpkvgwy
nreyldvetgemvreekswrakdtnctefwgplfkhepfrdaikrhyqlgaidsnevvd
aevdelisskvekysapegkskpsaadiendldmmedlde (SEQ ID No. 19)

VRX_ Variant 20
mhhhhhhsiadlksrlikastskmtatltkskffndkdvvrtkipmlniaisgaldggmqs
gltifagpskhfksnmgltmvsaymnkypeaiclfydsefgiteaylramkvdperviht
piqsveqlkvdmvnqleaiergekviifidsignmaskketedalnekvvsdmtraktm
kslfrivtpffsikdipcvavnhtietiemysktvmtggtgvmysadtvfiigkrqiketgk
elegfqfvlnaeksrmvkekskfkidvkfdggidpysglldmameigfvvkpkvgwy -continued nreyldvetgemvreekswrakdtnctefwgplfkhepfrdaikrhyqlgaidsnevvd
aevdelisskvekysapegkskpsaadiendldmmedldelde (SEQ ID No.
20)

Further, the room temperature amplification reaction system is constructed as follows:

| Reaction reagent | Final concentration |
|---|---|
| ris(hydroxymethyl) aminomethane-acetic acid buffer solution | 50-100 mM |
| Potassium acetate | 50-100 mM |
| Magnesium acetate | 5-20 mM |
| Dithiothreitol | 1-10 mM |
| Polyethylene glycol (molecular weight: 1450-20000) | 2.5%-12% |
| ATP | 1-10 mM |
| Phosphocreatine | 10-50 mM |
| Creatine kinase | 20-150 ng/ul |
| Cold-active bacteriophage uvsX | 200-600 ng/ul |
| Cold-active bacteriophage gp32 | 200-1000 ng/ul |
| Cold-active bacteriophage uvsY | 20-100 ng/ul |
| *Staphylococcus aureus* polymerase I klenow fragment (exo−) | / |
| Bacillus subtilis (exo−) | 8 Units |
| dNTP | 450 uM |
| Forward primer | 100 nM-600 nM |
| Reverse primer | 100 nM-600 nM |

TemplateCell lysis template/genome extraction/plasmid

Reaction conditions are as follows: 25 ul, amplification temperature: 20-45° C. A water bath, a thermostatic equipment or PCR instrument is taken. The reaction endpoint is monitored by agarose gel electrophoresis, Sybr green I or a specific probe. During Sybr green I monitoring, the reaction system has an increased final concentration of 0.3-0.5x Sybr green I. The reaction time may be within 20-40 min, and fluorescence is read every 30 s, and the fluorescent channel is FAM/HEX. The detection instrument may be ABI7500, FTC-3000, Bio-Rad CFX MiniOpticon System, GenDx thermostatic fluorescence detector GS8, or the like. For example, when a specific probe is used to detect the amplification system, an exonuclease III or an endonuclease IV is added to the reaction, and the reaction has a final concentration of 50-100 ng/ul, and the fluorescent-labeled probe has a final concentration of 120 nM. Probe labeling is designed and synthesize by reference to [22]. The fluorescence detection may be performed via ABI7500,FTC-3000, Bio-Rad CFX MiniOpticonSystemOpticon System, GenDx thermostatic fluorescence detector GS8, or the like.

The Present Invention has the Following Beneficial Effects:

the cold-active bacteriophage protein provided by the present invention is applied in room temperature nucleic acid amplification reaction, which may not only achieve nucleic acid amplification and detection at a lower temperature, but also may further improve detection sensitivity, capable of detecting 100 copies/ul nucleic acid.

DETAILED DESCRIPTION OF THE EMBODIMENTS

Figure 1:
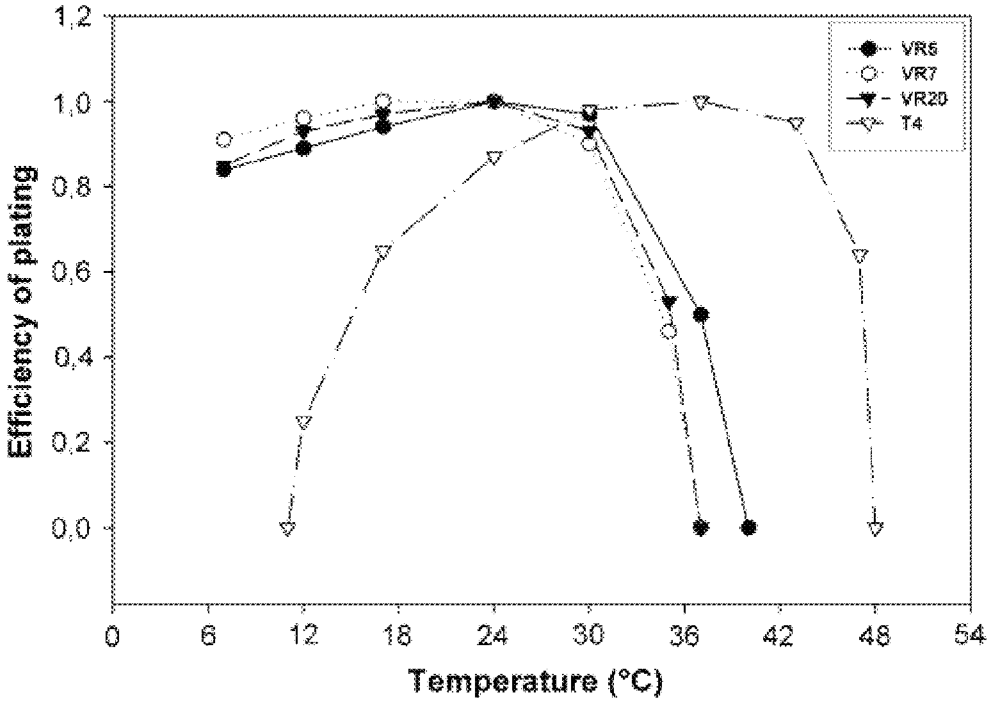
FIG. 1 shows efficiency of plating tests VR5, VR7, VR20 and T4 (control) at different temperatures.
Figure 2:
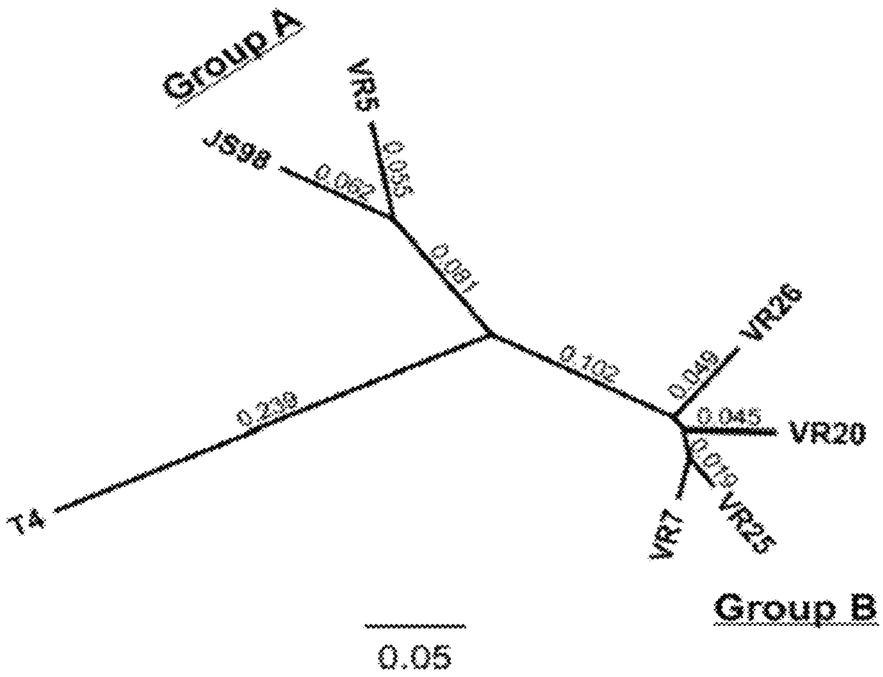
FIG. 2 shows phylogenetic analysis of genome Geneious v5.5.
Figure 3:
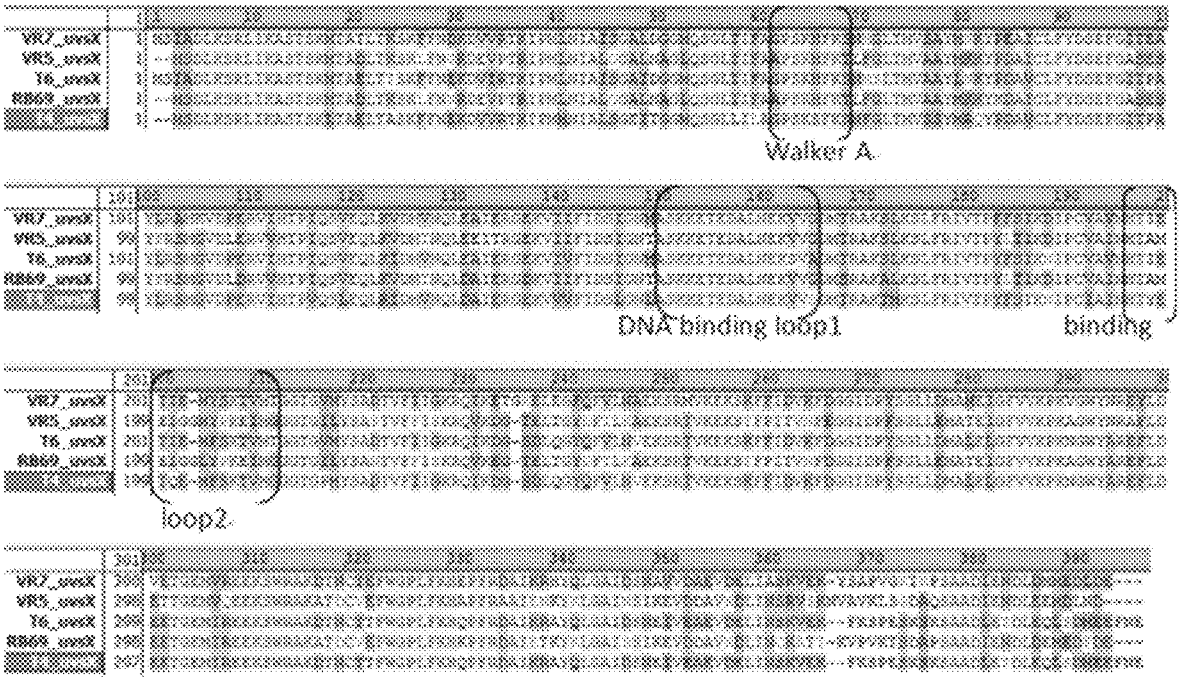
FIG. 3 shows uvsX sequence alignment between different species.

To describe the objective, technical solution and advantages of the present invention more clearly and apparently, the present application will be further described specifically by reference to the drawings and detailed embodiments. The following examples are only used to describe the present invention, but not intended to limit the scope of the present invention.

Example I Construction of a Recombinant Protein Expression Vector, Protein Expression and Purification The corresponding gene sequences were designed and synthesized respectively according to the NCBI genome sequences (Enterobacteria phage vB_EcoM_VR5, Accession: KP007359.1; vB_EcoM-VR7, Accession: HM563683.1; vB_EcoM_VR20, Accession: KP007360.1; vB_EcoM_VR25, Accession: KP007361.1; vB_EcoM_VR26, Accession: KP007362.1), and cloned onto a pET22b expression vector respectively by double enzyme digestion Nde I and EcoR I, where if a C terminal of the corresponding protein of the gene sequence was fused with 6 histidine-tag, gene +Chis was named, if an N terminal was was fused with 6 histidine-tag, gene +NHis was named; gene number was added simultaneously when the amino acid sequences were consistent among different virus strains, e.g., VR7_25_26Y_CHis, showing that the uvsY amino acid sequences of the three vB_EcoM_VR7, vB_EcoM_VR25 and vB_EcoM_VR26 were consistent, and the protein corresponding to the number was the protein with the addition of 6XHis tags on the C terminal. The expressed proteins were constructed and synthesized, including VR5X_NHis, VR7_25X_NHis, VR20_26X_NHis, VR5G_NHis, VR7G_NHis, VR25G_NHis, VR5Y_NHis, VR7_25_26Y_NHis, VR20Y_NHis, VR7_25X_CHis, VR7G_CHis, VR7_25_26Y_CHis and other corresponding plasmid vectors. A host cell BL21(DE3) was transformed according to molecular cloning technique, and induced with IPTG for expression, then repeatedly frozen and lyzed, and purified [28] by a Ni column to obtain a high-purity protein, and the high-purity protein was subjected to amplification test.

Example II Construction of an Enterobacteria Phage vB_EcoM VR5 Amplification System The reaction reagent and concentration thereof were as follows: 30 mMtris(hydroxymethyl) aminomethane-acetic acid buffer solution, 60 mM potassium acetate, 20 mM magnesium acetate, 2 mMdithiothreitol, 5% polyethylene glycol (molecular weight: 1450-20000), 3 mM ATP, 30 mM phosphocreatine, 90 ng/ulcreatine kinase, 200-600 ng/ul VR5X_NHis protein, 200-1000 ng/ul VR5G_NHis protein, 60 ng/ul VR5Y_NHis protein, 8 Units *Staphylococcus aureus* polymerase I klenow fragment (exo-), 450 uMdNTP, 250 nM forward primer: peu-F:5'-GCGAACGGGT-GAGTAACACGTATCCAATCT-3' (SEQ ID NO. 39, 250 nM reverse primer: peu-R1:5'-AGCCAT-TACCTGCTAAAGTCATTCTTCCCAAA-3' (SEQ ID NO. 40), and 10 ng/ul *Mycoplasma pneumoniae* genome DNA template, and the Sybr Green I had a final concentration of 0.4x. Reaction conditions were as follows: 20 ul, amplification temperature was 30° C. GenDx thermostatic fluorescence amplifier (specification: GS8) (http://www.gendx.cn/goods.php?id=64) was taken. The amplified result was realtimely detected by Sybr green I at the reaction endpoint. Amplification time: 30 min.

Figure 4:
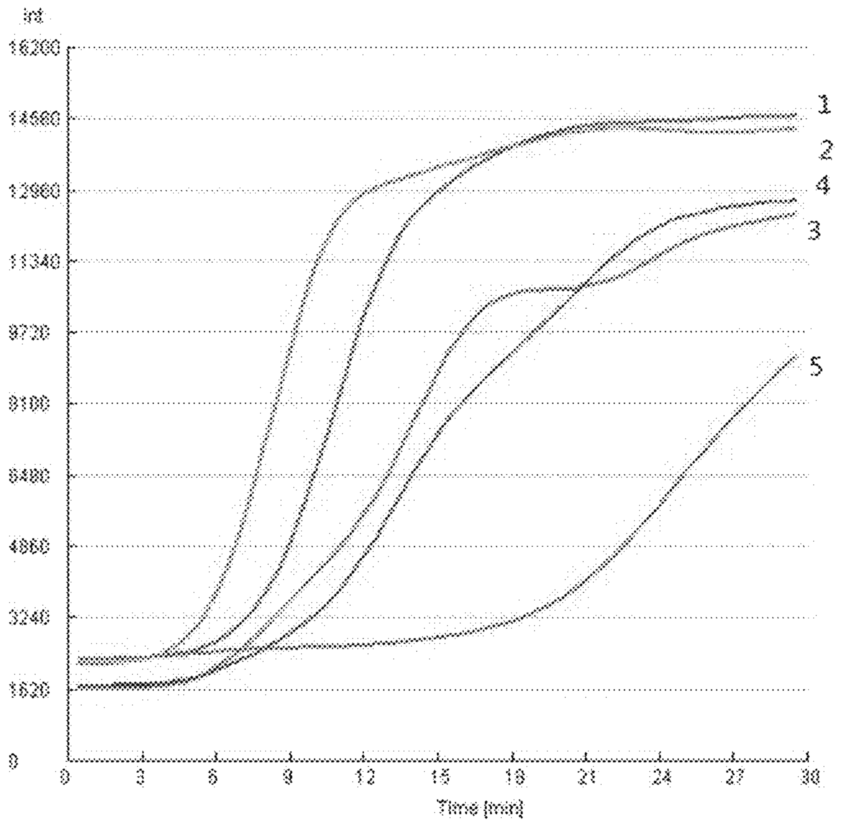
FIG. 4 is a curve graph showing isothermal amplification performed by an Enterobacteria phage vB_EcoM_VR5 amplification system.

The amplified result was shown in FIG. 4.

S1: VR5G_NHis protein, 1000 ng/ul VR5X_NHis protein, 300 ng/ul

S2: VR5G_NHis protein, 800 ng/ul VR5X_NHis protein, 400 ng/ul

S3: VR5G_NHis protein, 600 ng/ul VRSX_NHis protein, 300 ng/ul

S4: VR5G_NHis protein, 400 ng/ul VR5X_NHis protein, 200 ng/ul

S5: VR5G_NHis protein, 200 ng/ul VR5X_NHis protein, 600 ng/ul

VR5Y_NHis protein, 60 ng/ul, and other reagent components were consistent in this example.

The result shows that low temperature protein may be amplified directed to a specific template and be chimeric onto double strands by Sybr Green I, then a fluorescence signal was gave out to read and obtain the amplification curve by the fluorescence signal. The low temperature protein had inconsistent amplification efficiency at different concentrations in the solution.

Example III Construction of an Enterobacteria Phage vB_EcoM VR7 Amplification System The reaction reagent and concentration thereof were as follows: 100 mMtris(hydroxymethyl) aminomethane-acetic acid buffer solution, 120 mM potassium acetate, 15 mM magnesium acetate, 6 mMdithiothreitol, 6% polyethylene glycol (molecular weight: 1450-20000), 2 mM ATP, 40 mM phosphocreatine, 75 ng/ulcreatine kinase, 400 ng/ul VR7_25X_NHis or VR7_25X_CHis protein, 480 ng/ul VR7G_NHis or VR7G_CHis protein, 80 ng/ul VR7_25_26Y NHis or VR7_25_26Y_CHis protein, 8 Units *Bacillus subtilis* polymerase I klenow fragment (exo-), 450 uMdNTP, 50 ng/ulexo excision enzyme III, 250 nM forward primer ARMP-F, 250 nM reverse primer ARMP-R,120 nM fluorescent probe, about 25 ng/ul arginine *mycoplasma* genome DNA template, and primer and probe sequences were respectively as follows:

```
ARMP-F:
                                        (SEQ ID NO. 41)
5'-AGCATGTGGTTTAATTTGATGTTACGCGG-3'

ARMP-R:
                                        (SEQ ID NO. 42)
5'-CCATGCACCATCTGTCACTCCGTTAACCTCCG-3'

ARMP-PB:
                                        (SEQ ID NO. 43)
5'-TGTTACGCGGAGAACCTTACCCAC(Fam-dT)(THF)T(BHQ1-dT)
GACATCCTTCGCAAT-3'
```

Reaction conditions were as follows: 50 ul, amplification temperature was 40° C.

Figure 5:
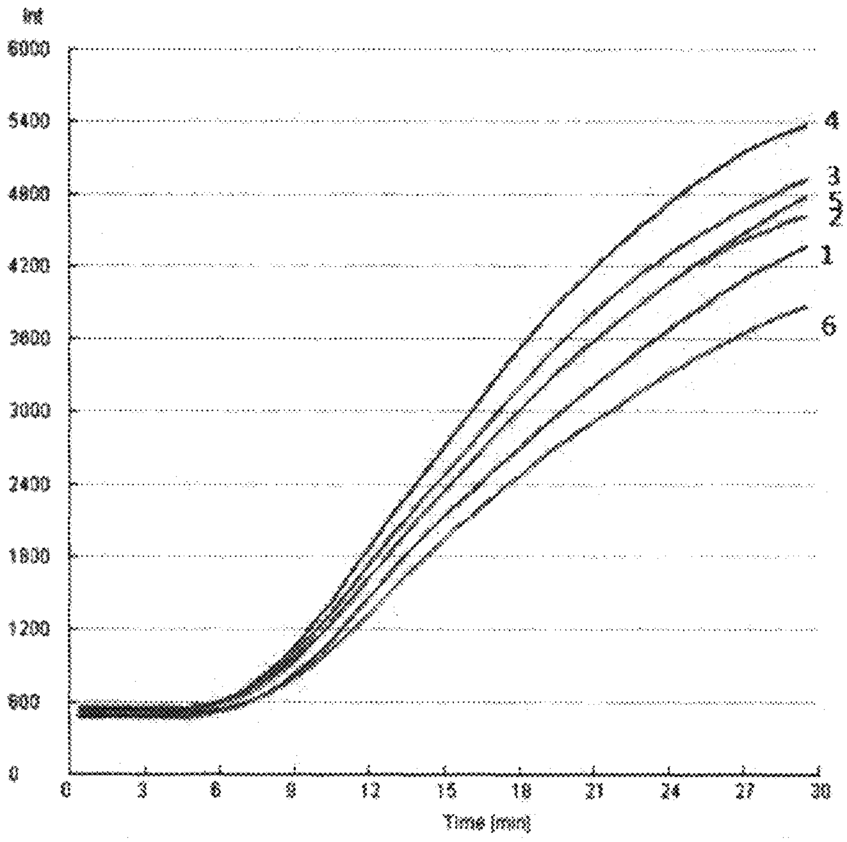
FIG. 5 shows a curve graph showing isothermal amplification performed by an Enterobacteria phage vB_EcoM_VR7 amplification system.

GenDx thermostatic fluorescence amplifier (specification: GS8) was taken. The amplified result was shown in FIG. 5.

S1/S2 reaction well: 400 ng/ul VR7_25X_NHis protein, 480 ng/ul VR7G_NHis protein; 80 ng/ul VR7_25_26Y_NHis protein.

S3/S4 reaction well: 400 ng/ul VR7_25X_CHis protein, 480 ng/ul VR7G_CHis protein, 80 ng/ul VR7_25_26Y_CHis protein.

S5 reaction well: 400 ng/ul VR7_25X_NHis protein, 480 ng/ul VR7G_CHis protein, 80 ng/ul VR7_25_26Y_NHis protein.

S6 reaction well: 400 ng/ul VR7_25X_CHis protein, 480 ng/ul VR7G_CHis protein, 80 ng/ul VR7_25_26Y_NHis protein.

The amplification result shows that even through the amplified fluorescence signal height value has certain differences, the detection threshold of the fluorescent amplification signal (the response time of the change of the fluorescence signal value might be monitored, TT, Threshold Time) was basically consistent. It is proved that the His protein tag has no obvious difference on the protein activity influence at the N-terminal or C-terminal of the fusion protein under the same protein concentration.

Example IV Construction of a Mixed Protein Amplification System Derived from Different Species Protein sequences derived from five different virus strains were mixed to test whether the mixed protein derived from different strains could be amplified. The reaction reagent and concentration thereof were as follows: 50 mMtris(hydroxymethyl) aminomethane-acetic acid buffer solution, 80 mM potassium acetate, 20 mM magnesium acetate, 2 mMdithiothreitol, 6% polyethylene glycol (molecular weight: 1450-20000), 2 mM ATP, 30 mM phosphocreatine, 60 ng/ulcreatine kinase, 400 ng/uI VR5X_NHis, VR7_25X_NHis or VR20_26X_NHis protein, 600 ng/uI VR7G_NHis or VR25G_NHis protein, 55 ng/uI VR7_25_26Y_NHis or VR20Y_NHis protein, 8 Units *Staphylococcus aureus* polymerase I klenow fragment (exo-), 450 uMdNTP, 50 ng/ulexo excision enzyme III, 400 nM forward primer susF, 400 nM reverse primer susR,120 nM fluorescent probe susPB, about 15 ng/uI swine genome DNA template (or NTC as control, replaced by the same volume of ddH2O); the reaction conditions were as follows: 50 uI, amplification temperature: 36° C. GenDx thermostatic fluorescence amplifier (specification: GS8) was taken.

Primer and probe sequences were as follows:

```
susF:
                                        (SEQ ID NO. 44)
5'-AGAGATCGGGAGCCTAAATCTCCCCTCAATGG-3'

susR:
                                        (SEQ ID NO. 45)
5'-TCGAGATTGTGCGGTTATTAATGAGTCGTTTGGG-3'

susPB:
                                        (SEQ ID NO. 46)
5'-TGCCACAACTAGATACATCCACATGATTCAT(FAM-dT)(THF)
CAA(BHQ1-dT)TACATCAATAAT(C3-SPACER)- 3'
```

The result was shown in FIG. 6. The amplification result proves that the uvsX protein, uvsY protein, and GP32 protein derived from different strains are added to the reaction according to a certain ratio; proteins from different sources may also be interacted to participate in primer binding and melting; under the action of polymerase, amplification is performed directed to a specific template. The protein concentration is consistent, but there are large differences in the amplification efficiency, which proves that proteins from different sources have inconsistent interaction ability.

| | | | |
|---|---|---|---|
| S1/S2: | VR5X_NHis | VR25G_NHis | VR7_25_26Y_NHis |
| S3/S4: | VR5X_NHis | VR25G_NHis | VR20Y_NHis |
| S5/S6: | VR7_25X_NHis | VR25G_NHis | VR7_25_26Y_NHis |
| S7/S8: | VR20_26X_NHis | VR25G_NHis | VR20Y_NHis |

Figure 6A:
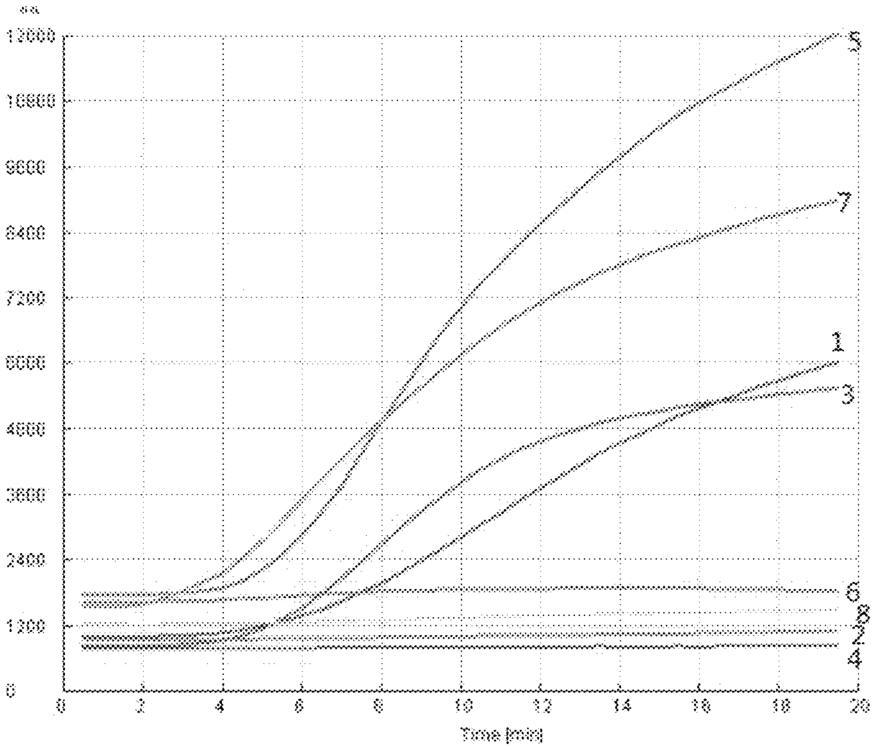
FIG. 6 shows a curve graph showing isothermal amplification performed by a mixed protein amplification system derived from different species.

S1/S3/S5/S7 was a template with the addition of genome DNA. S2/S4/S6/S8 was NTC negative control. (FIG. 6*a*)

| | | | |
|---|---|---|---|
| S1/S2: | VR5X_NHis | VR7G_NHis | VR7_25_26Y_NHis |
| S3/S4: | VR5X_NHis | VR7G_NHis | VR20Y_NHis |
| S5/S6: | VR5X_NHis | VR25G_NHis | VR7_25_26Y_NHis |
| S7/S8: | VR20_26X_NHis | VR25G_NHis | VR7_25_26Y_NHis |

Figure 6B:
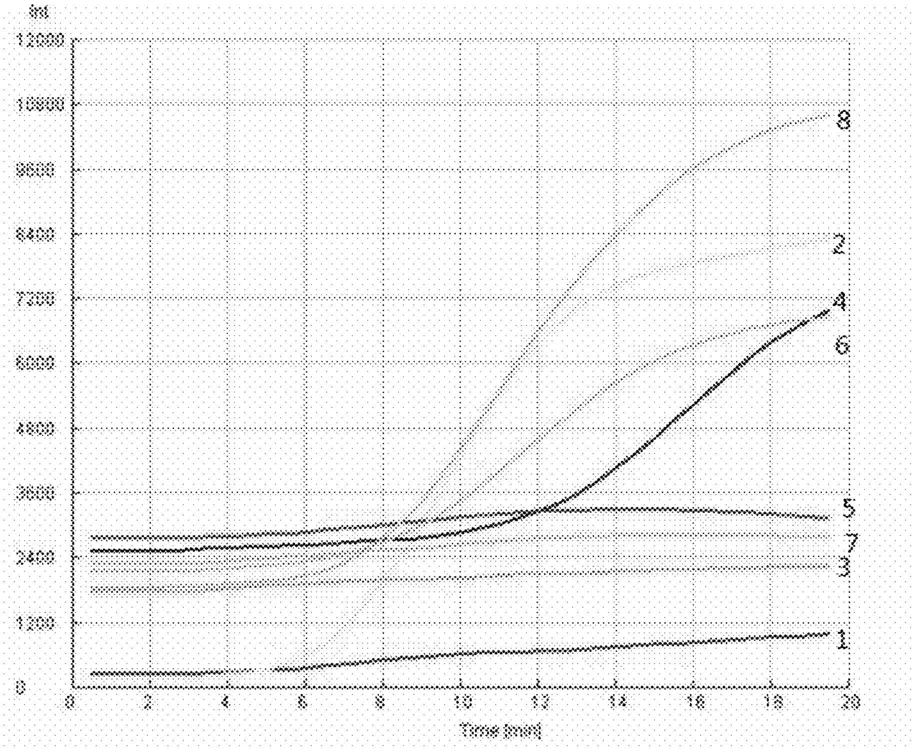

S1/S3/S5/S7 was NTC negative control. S2/S4/S6/S8 was a template with the addition of genome DNA. (FIG. 6*b*)

Figure 7:
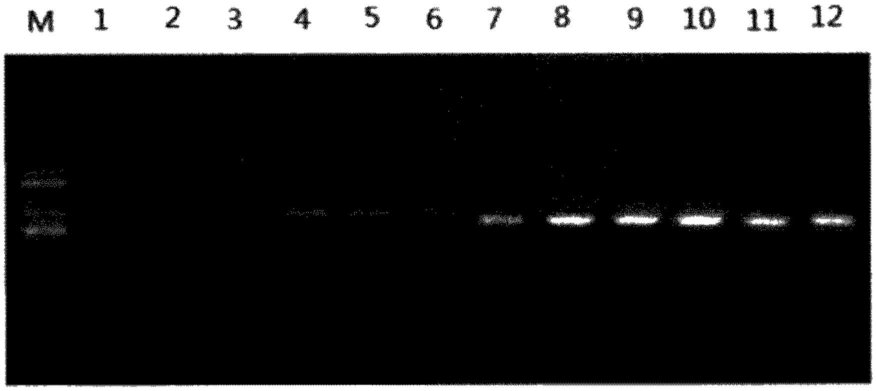
FIG. 7 shows electrophoretogram of an amplified product obtained by low temperature amplification by means of Enterobacteria phage vB_EcoM_VR5 amplification system and RPA (Recombinase polymerase amplification ) technology; strips 1, 2 and 3 are results respectively amplified by means of a RPA amplification reagent (TALQBAS01) at 20° C.; strips 4, 5 and 6 are results respectively amplified by means of a RPA amplification reagent (TALQBAS01) at 25° C.; strips 7, 8 and 9 are results respectively amplified by means of an Enterobacteria phage vB_EcoM_VR5 bacteriophage protein at 20° C.; and strips 10, 11 and 12 are results respectively amplified by means of an Enterobacteria phage vB_EcoM_VR5 bacteriophage at 25° C.

Example V Influence of Different Temperatures on Amplification Efficiency Tested by the Enterobacteria Phage vB_EcoM_VR5 Amplification System The Enterobacteria phage vB_EcoM_VR5 amplification system was used to test influences of different temperatures on amplification efficiency, and subjected to parallel comparison of amplification efficiency at low temperature with recombinase polymerase amplification (RPA). Enterobacteria phage vB_EcoM_VR5 amplification reaction reagent and concentration thereof were as follows: 20 mMtris(hydroxymethyl) aminomethane-acetic acid buffer solution, 120 mM potassium acetate, 10 mM magnesium acetate, 8 mMdithiothreitol, 5% polyethylene glycol (molecular weight: 20000), 3 mM ATP, 20 mM phosphocreatine, 30 ng/ulcreatine kinase, 350 ng/uI VR5X_NHis protein, 500 ng/uI VR5G_NHis protein, 50 ng/uI VR5Y_NHis protein, 10 Units *Bacillus subtilis* polymerase I klenow fragment (exo-), 450 uMdNTP, 250 nM forward primer: peu-F:5'-GCGAACGGGTGAGTAACACGTATCCAATCT-3'(SEQ ID NO. 47), 250 nM reverse primer: peu-R1:5'-AGCCATTACCTGCTAAAGTCATTCTTCCCAAA-3'(SEQ ID NO. 48), and about 100 pg/uI plasmid template carrying a segment of *Mycoplasma pneumoniae* 16srDNA gene sequence; the reaction conditions were as follows: 50 uI, and the amplification temperature was respectively configured into two temperatures: 20° C. and 25° C. A reagent TwistDx (www.twistdx.co.uk, Cat.No.: TALQBAS01) was used as control for the RPA technology; and products are used in strict accordance with the instruction. Three repeats were configured to each test. The reaction temperature was controlled by a water bath kettle; 1 h after reaction, the protein was inactivated immediately at a high temperature of 80° C.; the amplified product was precipitated by alcohol and then recycled, and dissolved by 20 uI TE; 10 uI recovered product was taken to detect the amplification result by gel electrophoresis, as shown in FIG. 7.

The sequence carrying the *Mycoplasma pneumoniae* 16srDNA segment gene was as follows:

```
                                        (SEQ ID NO. 49)
5'-AATACTTTAGAGGCGAACGGGTGAGTAACACGTATCCAATCTACCT

TATAATGGGGGATAACTAGTTGAAAGACTAGCTAATACCGCATAAGAAC

TTTGGTTCGCATGAATCAAAGTTGAAAGGACCTGCAAGGGTTCGTTATT

TGATGAGGGTGCGCCATATCAGCTAGTTGGTGGGGTAACGGCCTACCAA

GGCAATGACGTGTAGCTATGCTGAGAAGTAGAATAGCCACAATGGGACT

GAGACACGGCCCATACTCCTACGGGAGGCAGCAGTAGGGAATTTTTCAC

AATGAGCGAAAGCTTGATGGAGCAATGCCGCGTGAACGATGAAGGTCTT

TAAGATTGTAAAGTTCTTTTATTTGGGAAGAATGACTTTAGCAGGTAAT

GGCTAGAGTTTGACTGTACCATTTTGAATAAGTGACGACTAACTATGTG

CCAGCAGTCGCGGTAATACATAGGTCGCAAGCGTTATCCGGATTTATTG

GGCGTAAAGCAAGCGCAGGCGGATTGAAAAGTCTGGTGTTAAAGGCAGC

TGCTTAACAGTTGTATGCATTGGAAACTATTA-3'
```

The sequence was cloned onto a pUC57 vector, and the terminal sites were cut by an EcoR V enzyme.

It can be seen from the comparison of the reaction diagram that the amplification efficiency of the enzyme derived from low temperature species is obviously higher than that of T4 bacteriophage at low temperature of 20° C. and 25° C.

Based on the electrophoretic results of the amplification, the protein amplification efficiency derived from Enterobacteria phage vB_EcoM_VR5 bacteriophage is obviously superior to the amplification efficiency derived from T4 bacteriophage.

Figure 8:
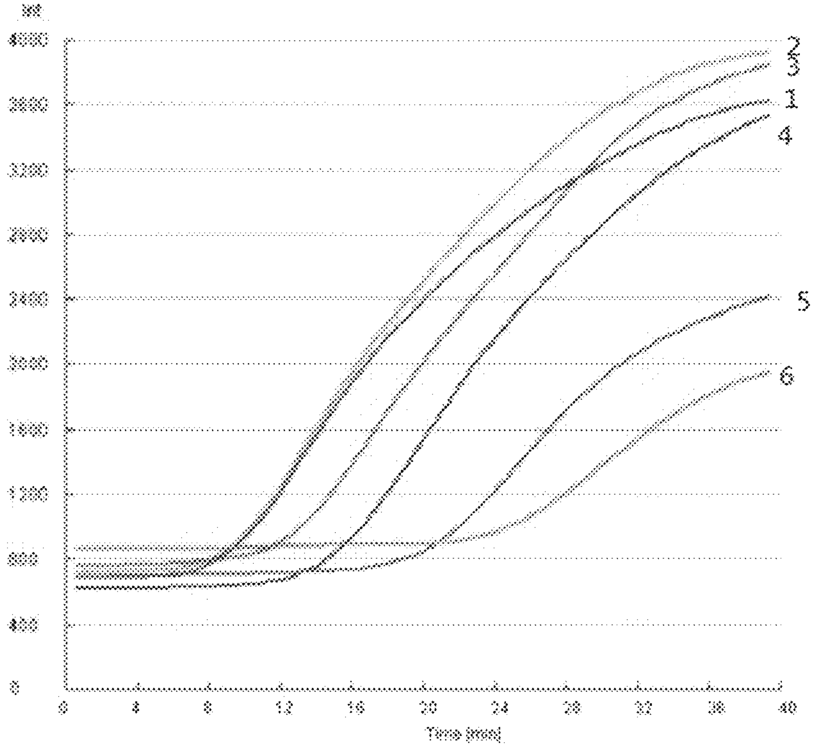
FIG. 8 shows a curve graph showing isothermal amplification performed by a variant-type creatine kinase and wild-type creatine kinase amplification system.

Example VI Influence of a Creatine Kinase Protein Variant Site on the Amplification Reaction The reaction reagent and concentration thereof were as follows: 30 mMtris(hydroxymethyl) aminomethane-acetic acid buffer solution, 60 mM potassium acetate, 8 mM magnesium acetate, 4 mMdithiothreitol, 3% polyethylene glycol (molecular weight: 1450-20000), 3 mM ATP, 50 mM phosphocreatine, 30-50 ng/ul RM-CK/RM-CK_G268N/Carp-M1-CK, 360 ng/ul VR7_25X_NHis protein, 500 ng/ul VR7G_NHis protein, 60 ng/ul VR7_25_26Y_NHis protein, 8 Units *Bacillus subtilis* polymerase I klenow fragment (exo-), 450 uMdNTP, 250 nM forward primer susF, 250 nM reverse primer susR, about 10 ng/ul pork tissue genome DNA template, a probe susPB was used for detection, nfo incision enzyme IV was used, and the final concentration was 130 ng/ul. Reaction conditions were as follows: 25 ul, amplification temperature was 32° C. The reaction was performed on a GenDx GS8 fluorescence amplifier, and the fluorescence scanning interval was 60 S, and the reaction time was 40 min. The result was shown in FIG. 8.

```
susF:
                                    (SEQ ID NO. 50)
5'-AGAGATCGGGAGCCTAAATCTCCCCTCAATGG-3'

susR:
                                    (SEQ ID NO. 51)
5'-TCGAGATTGTGCGGTTATTAATGAGTCGTTTGGG-3'

susPB:
                                    (SEQ ID NO. 52)
5'-TGCCACAACTAGATACATCCACATGATTCAT(FAM-dT)(THF)
CAA(BHQ1-dT)TACATCAATAAT(C3-SPACER)-3'

S1:
RM-CK_G268N/ 50 ng/µI

S2:
RM-CK_G268N/ 30 ng/µI

S3:
RM-CK/ 50 ng/µI

S4:
RM-CK/, 30 ng/µI;

S5:
Carp-M1-CK/ 50 ng/µI

S6:
Carp-M1-CK, 30 ng/µI
```

The test shows that in the reaction system using the enzyme of the present invention, the variant whose G is mutated into N in position 268 has amplification efficiency superior to the wild-type RM-CK.

Example VII Influence of Different Polymerases on Amplification Efficiency

The reaction system was as follows: 300 ng/ul VR7_25X_NHis protein, 400 ng/ul VR7G_CHis protein, 50 ng/ul VR7_25_26Y_NHis protein, 100 ng/ul polymerase (*Staphylococcus aureus* polymerase I klenow fragment (exo-)/*Bacillus subtilis* polymerase I klenow fragment (exo-)/*Escherichia coli* polymerase klenow fragment (exo-)/*Pseudomonas fluorescens* polymerase I klenow fragment (exo-); other reaction reagents and concentration thereof were the same as those in Example V, and Sybr Green I 0.4X was added additionally, and the amplification temperature was 33° C. The reaction was performed on a GenDx GS8 fluorescence amplifier, and the fluorescence scanning interval was 30 S, and the reaction time was 20 min.

Figure 9:
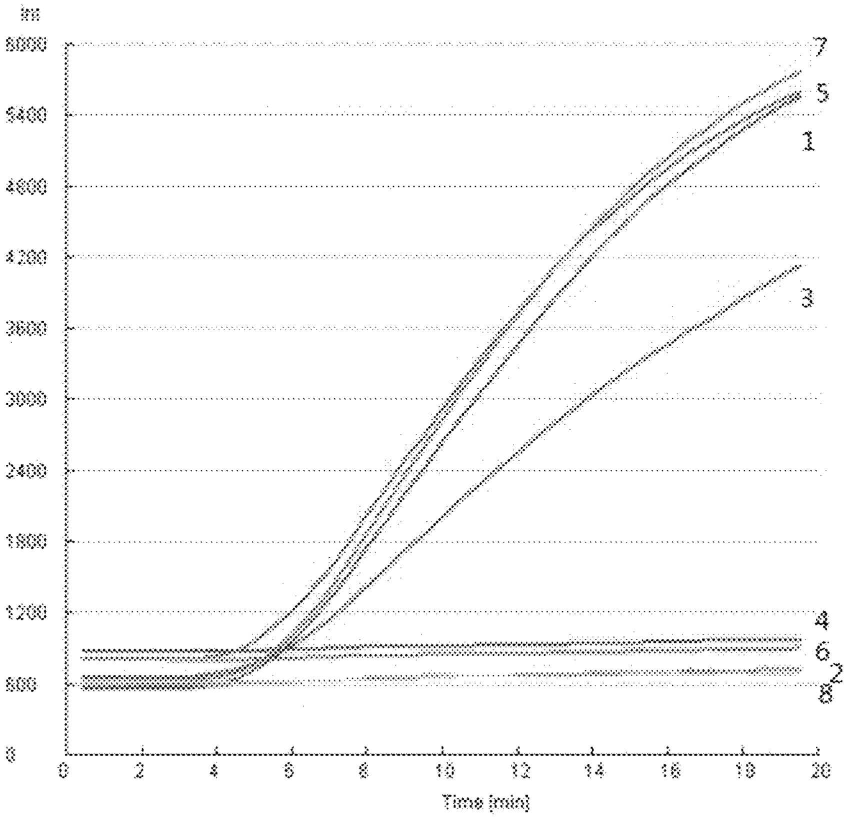
FIG. 9 shows a curve graph showing isothermal amplification performed by different polymerases in the reaction system.

The amplified result was shown in FIG. 9.

S1/S2: *Staphylococcus aureus* polymerase I klenow fragment (exo-)

S3/S4: *Bacillus subtilis* polymerase I klenow fragment (exo-)

S5/S6: *Escherichia coli* polymerase klenow fragment (exo-)

S7/S8: *Pseudomonas fluorescens* polymerase I klenow fragment (exo-)

S1/S3/S5/S7 was a template with the addition of genome DNA. S2/S4/S6/S8 was NTC negative control.

Based on the reaction result, *Escherichia coli* polymerase klenow fragment (exo-) has slightly low amplification efficiency, while the other three DNA polymerases have higher amplification efficiency.

Example VIII Lower Limit of Detection of the Amplification Sensitivity Tested at a Low Temperature of 35° C.

The reaction reagent and concentration thereof were as follows: 50 mMtris(hydroxymethyl) aminomethane-acetic acid buffer solution, 100 mM potassium acetate, 16 mM magnesium acetate, 2 mMdithiothreitol, 6% polyethylene glycol (molecular weight: 1450-20000), 2.5 mM ATP, 30 mM phosphocreatine, 120 ng/ulcreatine kinase, 450 ng/ul VR7_25X_NHis protein, 700 ng/ul VR7G_NHis protein, 70 ng/ul VR7_25_26Y_NHis protein, 8 Units *Staphylococcus aureus* polymerase I klenow fragment (exo-), 450 uMdNTP, 250 nM forward primer, 250 nM reverse primer; the template was a plasmid sequence synthesized by Grass Carp Reovirus GCRV VP7 protein gene, and respectively diluted into 10,000,000 copies/ul, 1,000,000 copies/ul, 100,000 copies/ul,10,000 copies/ul, 1000 copies/ul,100 copies/ul, and 10 copies/ul; the negative control was NTC, and 1 ul template was added to the reaction system during reaction. A probe was used for detection, exoexcision enzyme III was used, and the final concentration was 50 ng/ul. Reaction conditions were as follows: 50 ul, amplification temperature was 28° C.

```
GCRV-I-F203:
                                    (SEQ ID NO. 53)
5'-CCCACGCCAACGTCAAGACCATTCAAGACTCC-3'

GCRV-I-PB:
                                    (SEQ ID NO. 54)
5'-CAAATGAAGCCATTCGCTCATTAGTCGAAG(Fam-dT)
G(THF)G(BHQ1-dT)GACAAAGCGCAGACC(C3-SPACER)-3'

GCRV-I-R313:
                                    (SEQ ID NO. 55)
5'-TCCAATTCGTGATAGTCTACAGTACGGCTACC-3'
```

The sequence carrying Grass Carp Reovirus GCRV VP7 protein gene was as follows:

```
                                    (SEQ ID NO. 56)
5'-ATTCTAGCTAGCATGCCACTTCACATGATTCCGCAAGTCGCCCACG

CTATGGTGCGTGCAGCCGCTGCAGGACGCCTTACCTTATACACAAGAAC

TAGAACTGAGACCACCAACTTTGATCACGCTGAGTACGTCACCTGCGGG

CGGTACACCATCTGCGCCTTCTGCCTTACGACTCTGGCTCCCCACGCCA
```

-continued

```
ACGTCAAGACCATTCAAGACTCCCACGCTTGTTCACGTCAACCAAATGA

AGCCATTCGCTCATTAGTCGAAGTGAGTGACAAAGCGCAGACCGCCCTC

GTCGGTAGCCGTACTGTAGACTATCACGAATTGGATGTGAAAGCTGGGT

TCGTCGCCCCAACTGCCGATGAAACAATAGCCCCCTCTAAGGATATCGT

CGAACTTCCGTTTCGCACCTGTGACTTGTACGATTCCTCTGCTACCGCT

TGCGTCCGAAATCACTGCCAGGCCGGTCACGACGGCGTTATCCACCTCC

CGATCCTTTCTGGAGATTTCAAATTGCCTAACGAGCATCCCACCAAACC

GTTGGACGATACGCATCCCCACGACAAGGTGCTGACTCGCTGCCCCAAG

ACTGGTCTCCTCCTCGTCCATGACACTCACGCACACGCCACCGCCGTAG

TTGCCACCGCTGCTACGAGAGCTATCCTCATGCACGACCTCCTTACATC

AGCGAACGCGGATGACGGCCATCAAGCACGTTCCGCTTGCTACGGTCCA

GCGTTTAACAACCTGACCTTCGCTTGCCACTCCACCTGTGCTTCAGATA

TGGCTCACTTCGACTGCGGCCAGATCGTTGGACTCGACTTGCATGTGGA

GCCATCCGATTAACTCGAGCGGAAT-3'
```

The sequence was cloned onto a pUC57 vector, and the terminal sites were cut by an EcoR V enzyme.

The reaction was performed on a GenDx GS8 fluorescence amplifier, and the fluorescence scanning interval was 30 S, and the reaction time was 20 min.

Figure 10:
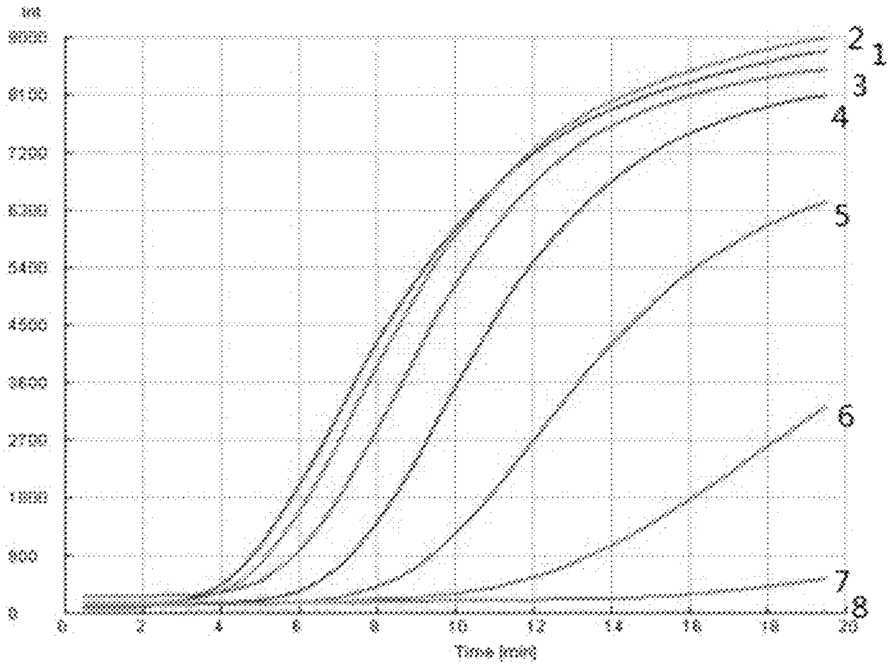
FIG. 10 shows a detection curve graph of sensitivity.
Figure 11A:
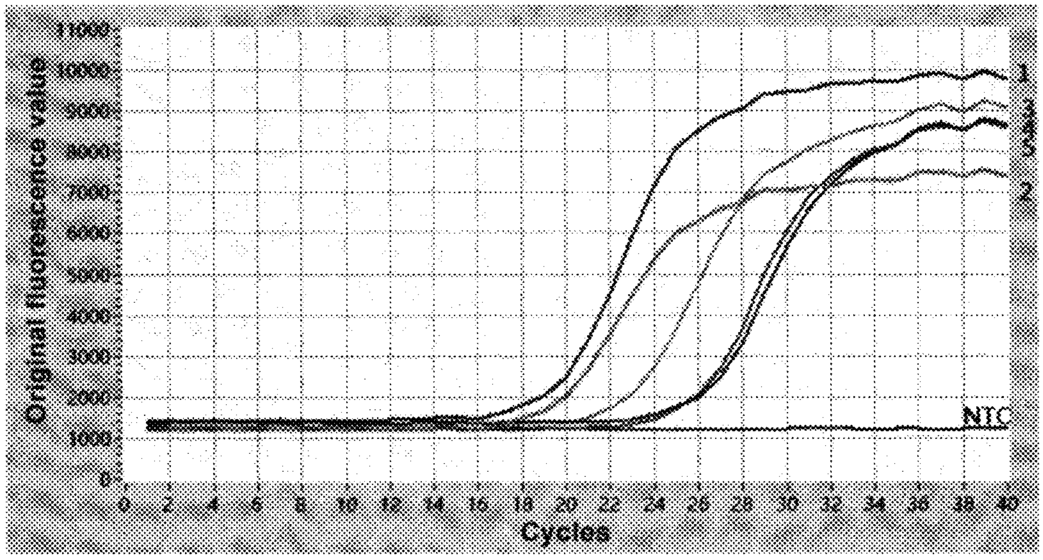
FIG. 11 is a curve graph showing isothermal amplification performed by different uvsX variants respectively in the reaction system.
Figure 11B:
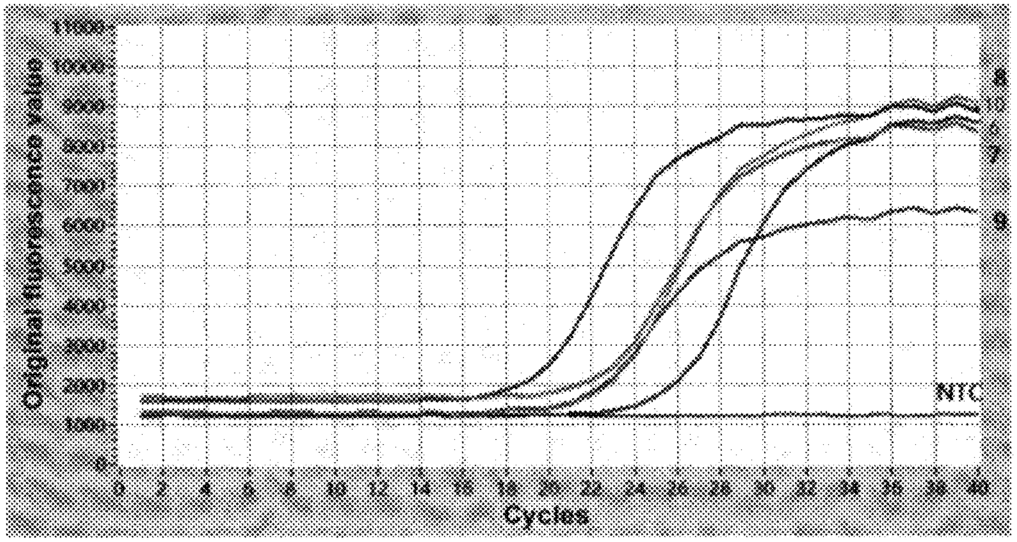
Figure 11C:
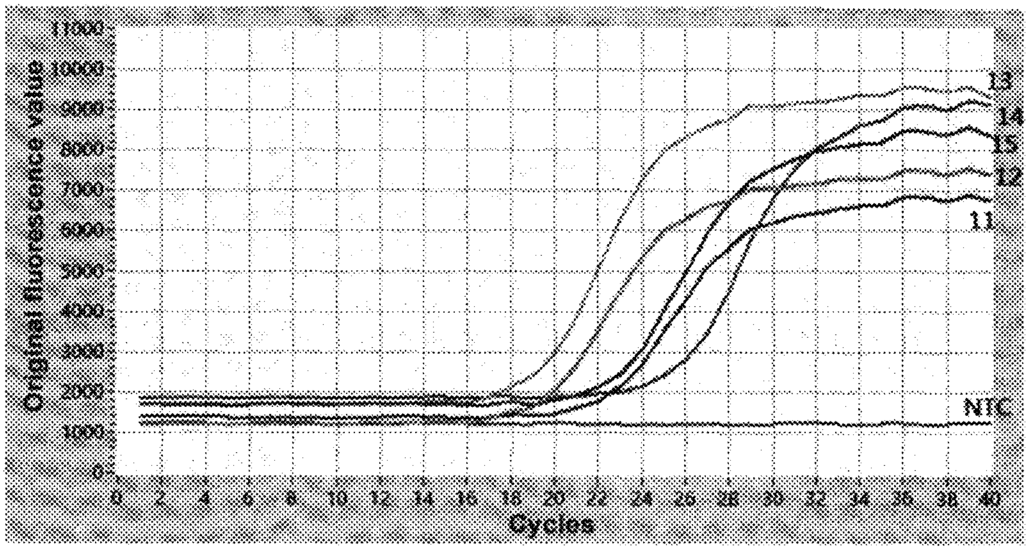
Figure 11D:
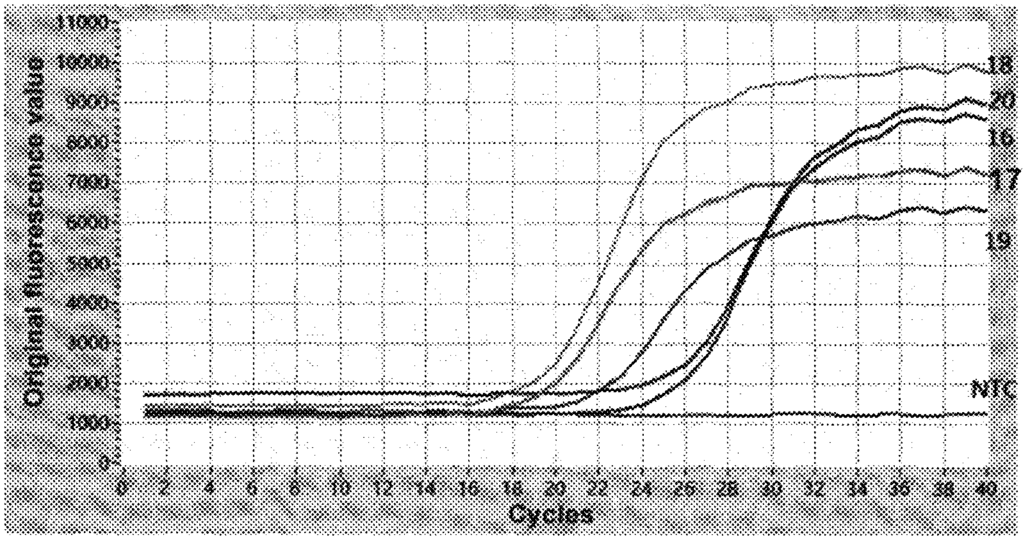
Figure 11E:
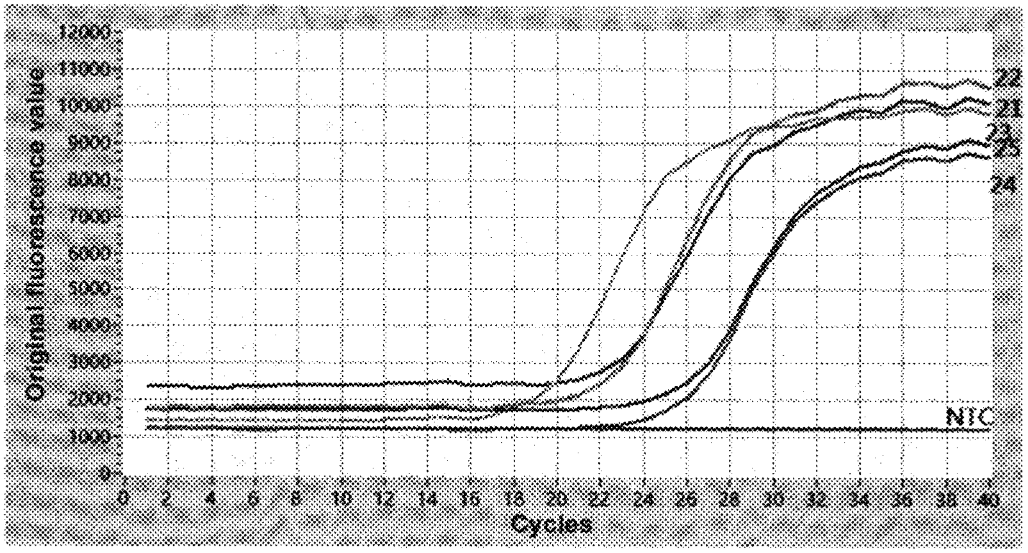

S1: 10,000,000 copies/uI,
S2: 1,000,000 copies/uI,
S3: 100,000 copies/uI,
S4: 10,000 copies/uI,
S5: 1000 copies/uI,
S6: 100 copies/uI,
S7: 10 copies/uI,
S8: Negative control was NTC;

The test result (FIG. 10) shows that the S6 sample has very obvious amplification, while the S7 sample has slightly increased fluorescence signal. Therefore, the detection sensitivity may be not lower than 100 copies/uI, and close to the sensitivity detected by other molecular diagnostic techniques. By optimization directed to the primer and probe sequence, it should be expected to obtain more excellent effect, thus achieving the detection for the amplified fluorescence signal of a single copy.

Example IX Influence of a uvsX Variant Site on the Amplification Reaction

The reaction reagent and concentration thereof were as follows: 20 mMtris(hydroxymethyl) aminomethane-acetic acid buffer solution, 120 mM potassium acetate, 10 mM magnesium acetate, 6% polyethylene glycol (molecular weight: 1450-20000), 4 mM ATP, 45 mM phosphocreatine, 90 ng/ulcreatine kinase, 450 ng/uluvsX protein from 20 different variants, 550 ng/uI VR7G_CHis protein, 60 ng/uI VR7_25_26Y_NHis protein, 120 ng/uI*Staphylococcus aureus* polymerase I klenow fragment (exo-), 450 uMdNTP, 400 nM forward primer ARMP-F, 400 nM reverse primer ARMP-R, and about 3000 copies/uI plasmid template carrying a segment of *Mycoplasma pneumoniae* 16srDNA gene sequence; Sybr Green I had a concentration of 0.5X; the reaction conditions were as follows: 50 uI, and the amplification temperature was 34° C. The reaction was performed on an MolARRAY MA-6000 fluorescent quantitative PCR amplifier, and the fluorescence scanning interval was 30 S, and the reaction time was 20 min.

```
peu-F:
                                        (SEQ ID NO. 57)
5'-GCGAACGGGTGAGTAACACGTATCCAATCT-3'

peu-R2:
                                        (SEQ ID NO. 58)
5'-CAAAGTTCTTATGCGGTATTAGCTAGTCTT-3'
```

The result was shown in 11 (a)-(e). In FIG. 11 (*a*):

| | |
|---|---|
| S1: | VRX_Variant1 450 ng/uI; VR5G_NHis 550 ng/ul; VR5Y_NHis 60 ng/uI; |
| S2: | VRX_Variant2 450 ng/uI; VR5G_NHis 550 ng/ul; VR5Y_NHis 60 ng/uI; |
| S3: | VRX_Variant3 450 ng/uI; VR5G_NHis 550 ng/ul; VR5Y_NHis 60 ng/uI; |
| S4: | VRX_Variant4 450 ng/uI; VR5G_NHis 550 ng/ul; VR5Y_NHis 60 ng/uI; |
| S5: | VR5X_NHis 450 ng/uI; VR5G_NHis 550 ng/ul; VR5Y_NHis 60 ng/ul; |
| NTC: | VR5X_NHis 450 ng/ul; VR5G_NHis 550 ng/ul; VR5Y_NHis 60 ng/uI; |

there was no template.

In FIG. 11 (*b*):

| | |
|---|---|
| S6: | VRX_Variant5 450 ng/ul; VR7G_NHis 550 ng/ul; VR7_25_26Y_NHis 60 ng/ul; |
| S7: | VRX_Variant6 450 ng/ul; VR7G_NHis 550 ng/ul; VR7_25_26Y_NHis 60 ng/ul; |
| S8: | VRX_Variant7 450 ng/ul; VR7G_NHis 550 ng/ul; VR7_25_26Y_NHis 60 ng/ul; |
| S9: | VRX_Variant8 450 ng/ul; VR7G_NHis 550 ng/ul; VR7_25_26Y_NHis 60 ng/ul; |
| S10: | VR7_25X_NHis 450 ng/ul; VR7G_NHis 550 ng/ul; VR7_25_26Y_NHis 60 ng/ul; |
| NTC: | VR7_25X_NHis 450 ng/ul; VR7G_NHis 550 ng/ul; VR7_25_26Y_NHis 60 ng/ul; |

there was no template.

In FIG. 11 (*c*):

| | |
|---|---|
| S11: | VRX_Variant9 450 ng/ul; VR25G_NHis 550 ng/ul; VR20Y_NHis 60 ng/ul; |
| S12: | VRX_Variant10 450 ng/ul; VR25G_NHis 550 ng/ul; VR20Y_NHis 60 ng/ul; |
| S13: | VRX_Variant11 450 ng/ul; VR25G_NHis 550 ng/ul; VR20Y_NHis 60 ng/ul; |
| S14: | VRX_Variant12 450 ng/ul; VR25G_NHis 550 ng/ul; VR20Y_NHis 60 ng/ul; |
| S15: | VR20_26X_NHis 450 ng/ul; VR25G_NHis 550 ng/ul; VR20Y_NHis 60 ng/ul; |
| NTC: | VR20_26X_NHis 450 ng/ul; VR25G_NHis 550 ng/ul; VR20Y_NHis 60 ng/ul; |

there was no template.

In FIG. 11 (*d*):

| | |
|---|---|
| S16: | VRX_Variant13 450 ng/ul; VR7G_NHis 550 ng/ul; VR7_25_26Y_NHis 60 ng/ul; |
| S17: | VRX_Variant14 450 ng/ul; VR7G_NHis 550 ng/ul; VR7_25_26Y_NHis 60 ng/ul; |
| S18: | VRX_Variant15 450 ng/ul; VR7G_NHis 550 ng/ul; VR7_25_26Y_NHis 60 ng/ul; |
| S19: | VRX_Variant16 450 ng/ul; VR7G_NHis 550 ng/ul; VR7_25_26Y_NHis 60 ng/ul; |
| S20: | VR7_25X_NHis 450 ng/ul; VR7G_NHis 550 ng/ul; VR7_25_26Y_NHis 60 ng/ul; |

-continued

| | |
|---|---|
| NTC: | VR7_25X_NHis 450 ng/ul; VR7G_NHis 550 ng/ul; VR7_25_26Y_NHis 60 ng/ul; |

there was no template.

In FIG. 11 (*e*):

| | |
|---|---|
| S21: | VRX_Variant17 450 ng/ul; VR25G_NHis 550 ng/ul; VR7_25_26Y_NHis 60 ng/ul; |
| S22: | VRX_Variant18 450 ng/ul; VR25G_NHis 550 ng/ul; VR7_25_26Y_NHis 60 ng/ul; |
| S23: | VRX_Variant19 450 ng/ul; VR25G_NHis 550 ng/ul; VR7_25_26Y_NHis 60 ng/ul; |
| S24: | VRX_Variant20 450 ng/ul; VR25G_NHis 550 ng/ul; VR7_25_26Y_NHis 60 ng/ul; |
| S25: | VR20_26X_NHis 450 ng/ul; VR25G_NHis 550 ng/ul; VR7_25_26Y_NHis 60 ng/ul; |
| NTC: | VR20_26X_NHis 450 ng/ul; VR25G_NHis 550 ng/ul; VR7_25_26Y_NHis 60 ng/ul; |

there was no template.

The test result shows that the amplifiation efficiency of partial variants is obviously higher than the wild-type uvsX protein at different variant sites,such as, VRX_Variant1, VRX_Variant7, VRX_Variant11, VRX_Variant17, and VRX_Variant18. Moreover, it is presumed according to the above experiment that other variants may be also superior to the wild-type protein in combination with different gp32 and uvsY proteins.

Example X Detection on a Cell *Mycoplasma*-Contaminated Sample

The reaction reagent and concentration thereof were as follows: 30 mMtris(hydroxymethyl) aminomethane-acetic acid buffer solution, 60 mM potassium acetate, 8 mM magnesium acetate, 4mMdithiothreitol, 5% polyethylene glycol (molecular weight: 20000), 3 mM ATP, 50 mM phosphocreatine, 30 ng/ul RM-CK, 360 ng/ul VR7_25X_NHis protein, 500 ng/ul VR7G_NHis protein, 60 ng/ul VR7_25_26Y_NHis protein, 8 Units *Bacillus subtilis* polymerase I klenow fragment (exo-), 450 uMdNTP, 250 nM forward primer susF, 250 nM reverse primer susR, about 10 ng/ul pork tissue genome DNA template, a probe susPB was used for detection, and the probe susPB had a final concentration was 120 nM, and exonuclease III (exo III) had a final concentration of 70 ng/ul.Reaction conditions were as follows: 50 uI. Moreover, a reagent TwistDx (www.twistdx.co.uk, Cat.No.: TALQBASO1) was used for the RPA technology; exonuclease III (exo III) having a final concentration of 70 ng/uI was further added as control, and other amplificationconditions were consistent. The amplification temperature: 20-45° C., a temperature gradient every other 5° C. There were six groups of reaction (20, 25, 30, 35, 40, and 45° C.). The reaction was performed on a GenDx GS8 fluorescence amplifier, and the fluorescence scanning interval was 30 S, and the reaction time was 40 min.

Figure 12:
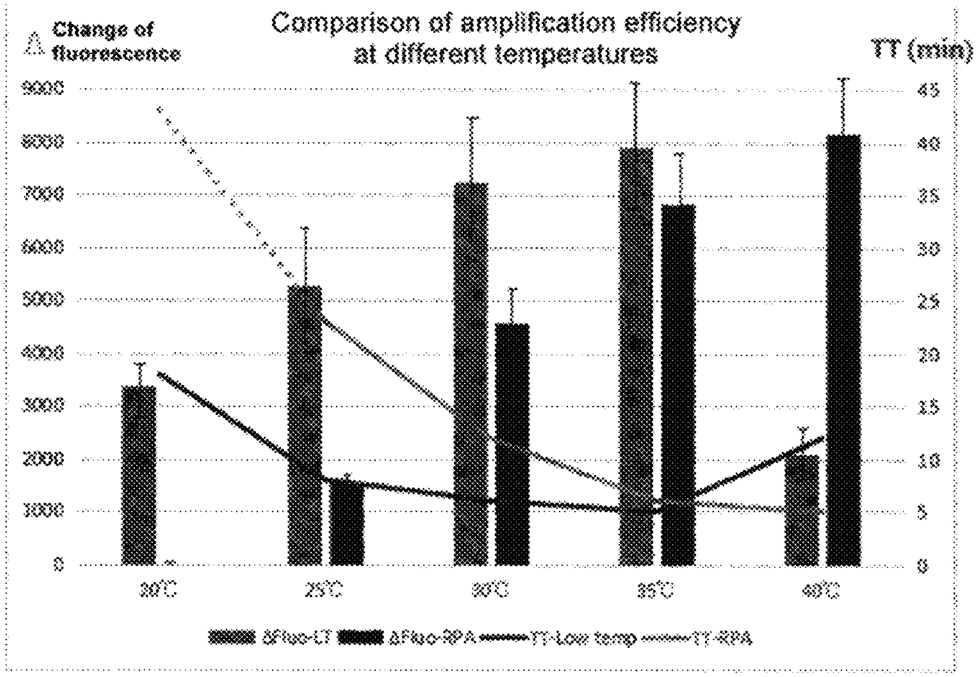
FIG. 12 shows influences of different temperatures on the amplification efficiency of a cold-active bacteriophage protein amplification system.

The experiment result was shown in FIG. 12: left y-coordinate: change of fluorescence signal value; right y-coordinate: time of beginning to change of the scanningfluorescence value after reaction; x-coordinate denotes different temperatures (where, 45° C. was not listed since no amplification was detected for the two reagents). Bar graph: fluorescence signal change value after amplification at different temperature, where gray denotes low-temperature protein derived from VR7, black denotes a RPA amplification reagent of exonuclease III (exo III); broken line graph denotes change time of the fluorescence signal (TT), where gray denotes low-temperature protein derived from VR7, black denotesexonuclease III.

The amplification result proves that different from RPA amplification reagent, the low-temperature protein system derived from VR7 has more obvious amplification effect at a condition of 20-30° C., and the RPA amplification reagent has higher amplification efficiency at 35-40° C., which is consistent with the literature report. In this test, no amplified fluorescence signal change was detected for the RPA reagent at a condition of 20° C.

Example XI Detection on Whether there was *Mycoplasma* Contamination in a Cell Sample by Amplification of Combined Proteins VRX_Variant1, VR5G_NHis, VR5Y_NHis The reaction reagent and concentration thereof were as follows: 100 mMtris(hydroxymethyl) aminomethane-acetic acid buffer solution, 120 mM potassium acetate, 15 mM magnesium acetate, 6mMdithiothreitol, 5% polyethylene glycol (molecular weight: 20000), 2 mM ATP, 40 mM phosphocreatine, 450 ng/uI VRX_Variant1,550 ng/uI VR5G_NHis,60 ng/uI VR5Y_NHis, 8 Units *Bacillus subtilis* polymerase I klenow fragment (exo-), 450 uMdNTP, and Sybr Green I 0.4X, 250 nM forward primer ARMP-F, 250 nM reverse primer ARMP-R, 120 nM fluorescent probe ARMP-PB; the primer and probe sequences were respectively as follows:

```
ARMP-F:
                                    (SEQ ID NO. 59)
5'-AGCATGTGGTTTAATTTGATGTTACGCGG-3'

ARMP-R:
                                    (SEQ ID NO. 60)
5'-CCATGCACCATCTGTCACTCCGTTAACCTCCG-3'
```

Reaction conditions were as follows: 50 uI, amplification temperature was 32° C. The sample was a cell culture fluid confirmed to be contaminated with *mycoplasma*; the fluorescence curve was detected after amplification.

Sample treatment: 500 μl cell supernatant (or the above cell suspension) was taken and centrifuged for 6 min at 14000 rpm; then supernatant was removed to collect precipitate (note: the supernatant may be absorbed by a sucker), and 50 μl sterile water was added and vibrated evenly, heated in a 95° C. water bath for 3 min, then slightly vibrated and mixed evenly, after rapid centrifugation, a DNA template was released to the supernatant; during the reaction, 2.5 uI were taken and added to the system as a template.

The reaction was performed on a Bio-Rad Mini Opticon fluorescent quantitative PCR instrument, and the fluorescence scanning interval was 30 S, and the reaction time was 25 min.

Figure 13:
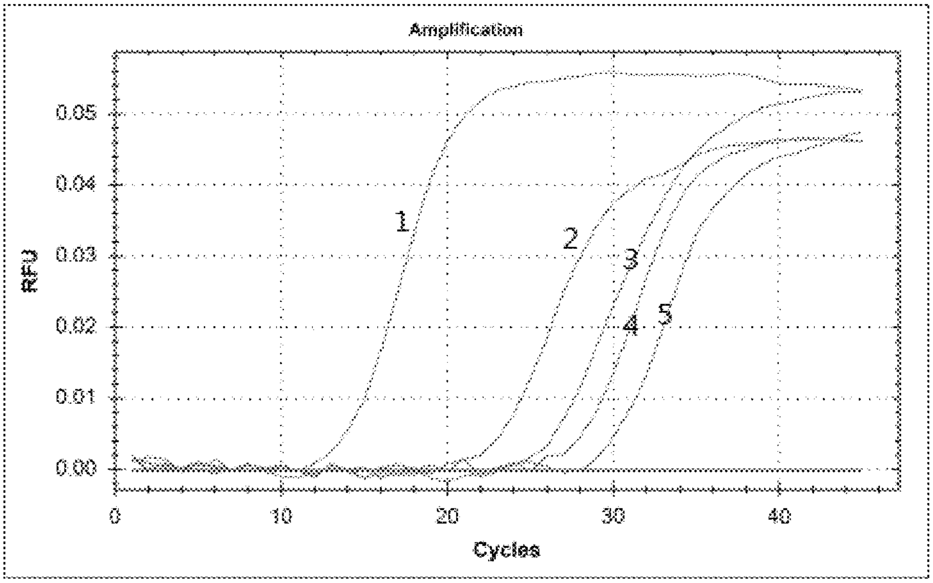
FIG. 13 is a curve graph showing isothermal amplification of a cell *mycoplasma*-contaminated sample detected by 450ng/uVRX_Variant1, 550ng/ul VR5G_NHis, 60ng/ul VR5Y_NHisamplification system.

The amplified result was shown in FIG. 13.

In FIG. 13:

S1: Sample No. 1

S2: Sample No. 2

S3: Sample No. 3

S4: Sample No. 4

S5: Sample No. 5

It is verified by amplification that the above samples may obtain positive amplification curves; according to different ct values, it is preliminarily presumed that No. 1 sample has more serious contamination.

REFERENCES

1. Yan L, Zhou J, Zheng Y, et al.
Isothermal amplified detection of DNA and RNA[J].Molecular Biosystems,2014,10(5):970-1003.
2. Sinha N K, Morris C F,
Alberts B M.Efficient in vitro replication of double-stranded DNA templates by a purified T4 bacter iophage replication system [J].Journal of Biological Chemistry,1980,255(9): 4290-4293.
3. Alberts B M,
Frey L.T4 Bacteriophage Gene 32:A Structural Protein in the Replication and Recombination of DN A[J].Nature, 1970,227(5265):1313-1318.
4. Formosa T, Burke R L, Alberts B M.
Affinity purification of bacteriophage T4 proteins essential for DNA replication and genetic recomb ination.[J].Proceedings of the National Academy of Sciences of the United States of America,1983, 80(9):2442-2446.
5. Yonesaki T, Ryo Y, Minagawa T, Takahashi H.
Purification and some of the functions of the products of bacteriophage T4 recombination genes, uvsX and uvsY Eur J Biochem.1985 Apr 1; 148(1):127-34.
6. Griffith J, Formosa T.
The uvsX protein of bacteriophage T4 arranges single-stranded and double-stranded DNA into simil ar helical nucleoprotein filaments.[J].Journal of Biological Chemistry, 1985,260(7):4484.
7. Formosa T, Alberts B M.
Purification and characterization of the T4 bacteriophage uvsX protein.[J].Journal of Biological Che mistry,1986,261 (13):6107-18.
8. Minagawa T, Fujisawa H, Yonesaki T, et al. Function of cloned T4 recombination genes, uvsX and uvsY, in cells of *Escherichia coli*.[J]. Molecular & General Genetics Mgg,1988,211(2):350-356.
9. Harris L D, Griffith J D.
UvsY protein of bacteriophage T4 is an accessory protein for in vitro catalysis of strand exchange. J Mol Biol.1989 Mar 5; 206(1):19-27.
10. Morrical S W, Alberts B M.
The UvsY protein of bacteriophage T4 modulates recombination-dependent DNA synthesis in vitro[J]. Journal of Biological Chemistry, 1990, 265(25): 15096-15103.
11. Beernink, H. T., and Morrical, S. W.(1999)
RMPPs:recombination/replication mediator proteins,Trends Biochem. Sci.24, 385-389.
12. Sweezy, M. A., and Morrical, S. W.(1999)
Biochemical interactions within a ternary complex of the bacteriophage T4 recombination proteins uvsY and gp32 bound to single-stranded DNA, Biochemistry 38, 936-944.
13. Beernink, H. T., and Morrical,
S. W.(1998)The uvsY recombination protein of bacteriophage T4 forms hexamers in the presence an d absence of single-stranded DNA, Biochemistry 37, 5673-5681.
14. Jie Liu, Jeffrey P. Bond, §, ‖ and, Scott W. Morrical, §, ‖.
Mechanism of Presynaptic Filament Stabilization by the Bacteriophage T4 UvsY Recombination M ediator[J]. Biochemistry, 2006, 45(17):5493.
15. Pant K, Shokri L, Karpel R L, et al.Modulation of T4 gene 32 protein DNA binding activity by the recombination mediator protein UvsY[J]. Journal of Molecular Biology, 2008, 380(5): 799-811.
16. U.S. Pat. No. 5,223,414 to Zarling et al.
17. Formosa T, Alberts B M. DNA synthesis dependent on genetic recombination: characterization of a reaction catalyzed by purified bacteriophage T4 proteins[J]. Cell, 1986, 47(5): 793-806.
18. Morrical S W, Wong M L, Alberts B M.
Amplification of snap-back DNA synthesis reactions by the uvsX recombinase of bacteriophage T4. [J]. Journal of Biological Chemistry, 1991, 266(21): 14031.
19. Salinas F, Jiang H, Kodadek T.
Homology dependence of UvsX protein-catalyzed joint molecule formation.[J].
Journal of Biological Chemistry, 1995, 270(10): 5181-6.
20. Morel P, Cherny D, Ehrlich S D, et al.
Recombination-dependent repair of DNA double-strand breaks with purified proteins from Escheric hia *coli*.[J]. Journal of Biological Chemistry, 1997, 272(27): 17091-6.
21. International patent application WO 02/086167, Benkovic and Salinas
22. Piepenburg, Olaf, Williams,Colin H.; Stemple,Derek L.; Armes, Niall A. (2006). "DNA Detection Using Recombination Proteins". PLoS Biology. 4(7): e204. Doi: 10.1371/journal.
Pbio. 0040204. PMC 1475771. PMID 16756388.
23. Comeau A M, Bertrand C, Letarov A, Tétart F, Krisch H M (2007)
Modular architecture of the T4 phage superfamily:a conserved core genome and a plastic periphery.
Virology 362: 384-396. doi:10. 1016/J. virol.2
24. Ackermann H-W, Krisch H M (1997)
A catalogue of T4-type bacteriophages.Arch Virol 142: 2329-2345
25. Leclerc H, Mossel DAA, Edberg SC, Struijk CB (2001)
Advances in the bacteriology of the coliform group:their suitability as markers of microbial water sa fety. Annu Rev Microbiol 55:201-234
26. Fileé J, Tétart F, Suttle C A, Krisch H M (2005) Marine T4-type bacteriophages, a ubiquitous component of the dark matter of the biosphere. Proc Natl Acad Sci USA 102: 12471-12476.
27. Seeley N D, Primrose S B (1980) The effect of temperature on the ecology of aquatic bacteriophages. J Gen Virol 46: 87-95
28. J. Written by Sambrook, et al., and translated by Huang Peitang, et al. Molecular Cloning, Version III, Science Press. 2002
29. YASUO IMAE, et al, Replication of T4 DNA In Vitro II.
Assay System for and Some Properties of Gene Products Required for T4 DNA Replication.
JOURNAL OF VIROLOGY, 1976, Vol. 19, No. 3 p.765-774
30. Alberts, B. M., and L. Frey. 1970. T4 bacteriophage gene 32:
a structural protein in the replication and recombination of DNA.Nature (London) 227: 1313-1318.
31. Fujisawa, H., Yonesaki, T.& Minagawa,T.(1985). Sequence of the T4 recombination gene, uvsX, and its comparison with that of the recA gene of *Escherichia coli*. Nucl. Acids Res. 13, 7473-7481.
32. Hinton, D. M. et al.
Cloning of the bacteriophage T4 uvsX gene and purification and characterization of the T4 uvsX rec ombination protein. 1986, Vol. 261, No. 12, Issue of April 25, pp. 5663-5673
33. et al.
Inhibition of Holliday structure resolving endonuclease VII of bacteriophage T4 by recombination e nzymes UvsX and UvsY J. Mol. Biol. (1997) 267, 150-162

34. Wu C L, Li Y H, Lin H C, Yeh Y H, Yan H Y, Hsiao C D, Hui C F, Wu J L.
Activity and function of rabbit muscle-specific creatine kinase at low temperature by mutation at gl y268 to asn268. Comp Biochem Physiol B Biochem Mol Biol.2011 Mar; 158(3): 189-98. Doi: 10.1016/j. cbpb. 2010.11.009. Epub 2010 Dec 3.

35. Wu C L, Li B Y, Wu J L, Hui C F.
The activity of carp muscle-specific creatine kinase at low temperature is enhanced by decreased hy drophobicity of residue 268. Physiol Biochem Zool. 2014 Jul-Aug; 87(4): 507-16. doi:10. 1086/676466. Epub 2014 Jun 3.

The invention claimed is:

1. A room temperature nucleic acid amplification reaction system, wherein the system comprises: a cold-active bacteriophage uvsX mutated protein having the amino acid sequence of SEQ ID NO: 1, a cold-active bacteriophage uvsY protein having the amino acid sequence of SEQ ID NO: 27, and a cold-active bacteriophage gp32 protein having the amino acid sequence of SEQ ID NO: 24, wherein the room temperature nucleic acid amplification reaction system further comprises a fluorescent probe sequence, wherein the room temperature nucleic acid amplification is Recombinase Polymerase Amplification (RPA) and has a reaction temperature of 34° C.

2. The room temperature nucleic acid amplification reaction system according to claim 1, wherein the system further comprises a polymerase, a nuclease, dNTP, a crowding agent, an energy substance, and a salt ion.

3. The room temperature nucleic acid amplification reaction system according to claim 2, wherein the polymerase is selected from any one or a combination of more than one of an *Escherichia coli* polymerase klenow fragment (exo-), a *Staphylococcus aureus* polymerase I klenow fragment (exo-), a *Bacillus subtilis* polymerase I klenow (exo-), a *Pseudomonas fluorescens* polymerase I klenow (exo-), and variants or klenow fragments of these enzymes.

4. The room temperature nucleic acid amplification reaction system according to claim 2, wherein the crowding agent is selected from any one or a combination of more than one of polyethylene glycol, polyvinyl alcohol, dextran or polysucrose.

5. The room temperature nucleic acid amplification reaction system according to claim 4, wherein the polyethylene glycol is selected from one or more of PEG1450, PEG3000, PEG8000, PEGIOOOO, PEG14000, PEG20000, PEG25000 and PEG30000.

6. The room temperature nucleic acid amplification reaction system according to claim 2, wherein the energy substance is selected from a combination of ATP or ATP, phosphocreatine or creatine kinase.

7. The room temperature nucleic acid amplification reaction system according to claim 2, wherein the salt ion is selected from any one or a combination of magnesium ion and potassium ion.

8. The room temperature nucleic acid amplification reaction system according to claim 2, wherein in the system, the polymerase is the *Staphylococcus aureus* polymerase I klenow fragment (exo-), the *Bacillus subtilis* polymerase I klenow fragment (exo-), the *Pseudomonas fluorescens* polymerase I klenow fragment (exo-), or a combination thereof.

9. The room temperature nucleic acid amplification reaction system according to claim 1, wherein the system further comprises a primer sequence and a template sequence.

* * * * *

SEQUENCE LISTING

```
<160> NUMBER OF SEQ ID NOS: 65

<210> SEQ ID NO 1
<211> LENGTH: 398
<212> TYPE: PRT
<213> ORGANISM: Artificial Sequence
<220> FEATURE:
<223> OTHER INFORMATION: Synthetic: VRX_Variant1

<400> SEQUENCE: 1

Asn Met His His His His His His Ser Asp Leu Lys Ser Arg Leu Ile
1               5                   10                  15

Lys Ala Ser Thr Ser Lys Met Thr Ala Asp Leu Thr Lys Ser Lys Leu
            20                  25                  30

Phe Asn Gly Arg Asp Glu Val Pro Thr Arg Ile Pro Met Leu Asn Ile
        35                  40                  45

Ala Leu Gly Gly Ala Leu Asn Ala Gly Leu Gln Ser Gly Leu Thr Ile
    50                  55                  60

Phe Ala Ala Pro Ser Lys Ser Phe Lys Thr Leu Phe Gly Leu Thr Met
65                  70                  75                  80

Val Ala Ala Tyr Met Lys Lys Tyr Pro Asp Ala Ile Cys Leu Phe Tyr
                85                  90                  95

Asp Ser Glu Phe Gly Ala Ser Glu Ser Tyr Phe Arg Ser Met Gly Val
            100                 105                 110

Asp Leu Glu Arg Val Val His Thr Pro Ile Gln Ser Val Glu Gln Leu
        115                 120                 125

Lys Val Asp Met Thr Asn Gln Leu Glu Glu Ile Thr Arg Gly Glu Lys
    130                 135                 140

Val Ile Ile Phe Ile Asp Ser Ile Gly Asn Thr Ala Ser Lys Lys Glu
145                 150                 155                 160

Thr Glu Asp Ala Leu Asn Glu Lys Val Val Gly Asp Met Thr Arg Ala
                165                 170                 175

Lys Ser Leu Lys Ser Leu Phe Arg Ile Val Thr Pro Tyr Leu Thr Ile
            180                 185                 190

Lys Asp Ile Pro Cys Val Ala Ile Asn His Thr Ala Met Glu Ile Gly
        195                 200                 205

Gly Met Tyr Pro Lys Glu Ile Met Gly Gly Gly Thr Gly Ile Leu Tyr
    210                 215                 220

Ser Ala Ser Thr Val Phe Phe Ile Ser Lys Arg Gln Val Lys Asp Gly
225                 230                 235                 240

Thr Glu Leu Thr Gly Tyr Asp Phe Thr Leu Lys Ala Glu Lys Ser Arg
                245                 250                 255

Thr Val Lys Glu Lys Ser Thr Phe Pro Ile Thr Val Asn Phe Glu Gly
            260                 265                 270

Gly Ile Asp Pro Phe Ser Gly Leu Leu Glu Met Ala Thr Glu Ile Gly
        275                 280                 285

Phe Val Val Lys Pro Lys Ala Gly Trp Tyr Asn Arg Ala Phe Leu Asp
    290                 295                 300

Glu Thr Thr Gly Glu Met Val Gln Glu Glu Lys Ser Trp Arg Ala Lys
```

```
305                 310                 315                 320

Ala Thr Asp Cys Val Glu Phe Trp Gly Pro Leu Phe Lys His Ala Pro
                325                 330                 335

Phe Arg Ala Ala Ile Glu Asn Lys Tyr Lys Leu Gly Ala Ile Asn Ser
            340                 345                 350

Ile Lys Glu Val Asp Asp Ala Val Asn Asp Leu Ile Asn Ser Arg Val
        355                 360                 365

Ser Lys Asn Val Ala Val Lys Leu Ser Gly Asp Ala Gln Ser Ala Ala
    370                 375                 380

Asp Ile Glu Asn Asp Leu Glu Glu Met Asp Leu Asn Asp Cys
385                 390                 395


<210> SEQ ID NO 2
<211> LENGTH: 396
<212> TYPE: PRT
<213> ORGANISM: Artificial Sequence
<220> FEATURE:
<223> OTHER INFORMATION: Synthetic: VRX_Variant2

<400> SEQUENCE: 2

Met His His His His His His Ser Asp Leu Lys Ser Arg Leu Ile Lys
1               5                   10                  15

Ala Ser Thr Ser Lys Met Thr Ala Asp Leu Thr Lys Ser Lys Leu Phe
            20                  25                  30

Asn Gly Arg Asp Glu Val Pro Thr Arg Ile Pro Met Leu Asn Ile Ala
        35                  40                  45

Leu Gly Gly Ala Leu Asn Ala Gly Leu Gln Ser Gly Leu Thr Ile Phe
    50                  55                  60

Ala Gly Pro Ser Lys His Phe Lys Thr Leu Phe Gly Leu Thr Met Val
65                  70                  75                  80

Ala Ala Tyr Met Lys Lys Tyr Pro Asp Ala Ile Cys Leu Phe Tyr Asp
                85                  90                  95

Ser Glu Phe Gly Ala Ser Glu Ser Tyr Phe Arg Ser Met Gly Val Asp
            100                 105                 110

Leu Glu Arg Val Val His Thr Pro Ile Gln Ser Val Glu Gln Leu Lys
        115                 120                 125

Val Asp Met Thr Asn Gln Leu Glu Glu Ile Thr Arg Gly Glu Lys Val
    130                 135                 140

Ile Ile Phe Ile Asp Ser Ile Gly Asn Thr Ala Ser Lys Lys Glu Thr
145                 150                 155                 160

Glu Asp Ala Leu Asn Glu Lys Val Val Gly Ser Met Thr Arg Ala Lys
                165                 170                 175

Ser Leu Lys Ser Leu Phe Arg Ile Val Thr Pro Tyr Leu Thr Ile Lys
            180                 185                 190

Asp Ile Pro Cys Val Ala Ile Asn His Thr Ala Met Glu Ile Gly Gly
        195                 200                 205

Met Tyr Pro Lys Glu Ile Met Gly Gly Gly Thr Gly Ile Leu Tyr Ser
    210                 215                 220

Ala Ser Thr Val Phe Phe Ile Ser Lys Arg Gln Val Lys Asp Gly Thr
225                 230                 235                 240

Glu Leu Thr Gly Tyr Asp Phe Thr Leu Lys Ala Glu Lys Ser Arg Thr
                245                 250                 255

Val Lys Glu Lys Ser Thr Phe Pro Ile Thr Val Asn Phe Glu Gly Gly
            260                 265                 270

Ile Asp Pro Phe Ser Gly Leu Leu Glu Met Ala Thr Glu Ile Gly Phe
```

```
        275                 280                 285

Val Val Lys Pro Lys Ala Gly Trp Tyr Asn Arg Ala Phe Leu Asp Glu
    290                 295                 300

Thr Thr Gly Glu Met Val Gln Glu Glu Lys Ser Trp Arg Ala Lys Ala
305                 310                 315                 320

Thr Asp Cys Val Glu Phe Trp Gly Pro Leu Phe Lys His Ala Pro Phe
                325                 330                 335

Arg Ala Ala Ile Glu Asn Lys Tyr Lys Leu Gly Ala Ile Asn Ser Ile
            340                 345                 350

Lys Glu Val Asp Asp Ala Val Asn Asp Leu Ile Asn Ser Arg Val Ser
        355                 360                 365

Lys Asn Val Ala Val Lys Leu Ser Gly Asp Ala Gln Ser Ala Ala Asp
    370                 375                 380

Ile Glu Asn Asp Leu Glu Glu Met Asp Leu Asn Asp
385                 390                 395


<210> SEQ ID NO 3
<211> LENGTH: 396
<212> TYPE: PRT
<213> ORGANISM: Artificial Sequence
<220> FEATURE:
<223> OTHER INFORMATION: Synthetic: VRX_Variant3

<400> SEQUENCE: 3

Met His His His His His His Ser Asp Leu Lys Ser Arg Leu Ile Lys
1               5                   10                  15

Ala Ser Thr Ser Lys Met Thr Ala Asp Leu Thr Lys Ser Lys Leu Phe
            20                  25                  30

Asn Gly Arg Asp Glu Val Pro Thr Arg Ile Pro Met Leu Asn Ile Ala
        35                  40                  45

Leu Gly Gly Ala Leu Asn Ala Gly Leu Gln Ser Gly Leu Thr Ile Phe
    50                  55                  60

Ala Gly Pro Ser Lys Ser Phe Lys Thr Leu Phe Gly Leu Thr Met Val
65                  70                  75                  80

Ala Ala Tyr Met Lys Lys Tyr Pro Asp Ala Ile Cys Leu Phe Tyr Asp
                85                  90                  95

Ser Glu Phe Gly Ile Ser Glu Ser Tyr Phe Arg Ser Met Gly Val Asp
            100                 105                 110

Leu Glu Arg Val Val His Thr Pro Ile Gln Ser Val Glu Gln Leu Lys
        115                 120                 125

Val Asp Met Thr Asn Gln Leu Glu Glu Ile Thr Arg Gly Glu Lys Val
    130                 135                 140

Ile Ile Phe Ile Asp Ser Ile Gly Asn Thr Ala Ser Lys Lys Glu Thr
145                 150                 155                 160

Glu Asp Ala Leu Asn Glu Lys Val Val Gly Ser Met Thr Arg Ala Lys
                165                 170                 175

Ser Leu Lys Ser Leu Phe Arg Ile Val Thr Pro Tyr Leu Thr Ile Lys
            180                 185                 190

Asp Ile Pro Cys Val Ala Ile Asn His Thr Ala Met Glu Ile Gly Gly
        195                 200                 205

Met Tyr Pro Lys Glu Ile Met Gly Gly Gly Thr Gly Ile Leu Tyr Ser
    210                 215                 220

Ala Ser Thr Val Phe Phe Ile Ser Lys Arg Gln Val Lys Asp Gly Thr
225                 230                 235                 240

Glu Leu Thr Gly Tyr Asp Phe Thr Leu Lys Ala Glu Lys Ser Arg Thr
```

-continued

```
                245                 250                 255

Val Lys Glu Lys Ser Thr Phe Pro Ile Thr Val Asn Phe Glu Gly Gly
            260                 265                 270

Ile Asp Pro Phe Ser Gly Leu Leu Glu Met Ala Thr Glu Ile Gly Phe
        275                 280                 285

Val Val Lys Pro Lys Ala Gly Trp Tyr Asn Arg Ala Phe Leu Asp Glu
    290                 295                 300

Thr Thr Gly Glu Met Val Gln Glu Glu Lys Ser Trp Arg Ala Lys Ala
305                 310                 315                 320

Thr Asp Cys Val Glu Phe Trp Gly Pro Leu Phe Lys His Ala Pro Phe
                325                 330                 335

Arg Ala Ala Ile Glu Asn Lys Tyr Lys Leu Gly Ala Ile Asn Ser Ile
            340                 345                 350

Lys Glu Val Asp Asp Ala Val Asn Asp Leu Ile Asn Ser Arg Val Ser
        355                 360                 365

Lys Asn Val Ala Val Lys Leu Ser Gly Asp Ala Gln Ser Ala Ala Asp
    370                 375                 380

Ile Glu Asn Asp Leu Glu Glu Met Asp Leu Asn Asp
385                 390                 395


<210> SEQ ID NO 4
<211> LENGTH: 396
<212> TYPE: PRT
<213> ORGANISM: Artificial Sequence
<220> FEATURE:
<223> OTHER INFORMATION: Synthetic: VRX_Variant4

<400> SEQUENCE: 4

Met His His His His His His Ser Asp Leu Lys Ser Arg Leu Ile Lys
1               5                   10                  15

Ala Ser Thr Ser Lys Met Thr Ala Asp Leu Thr Lys Ser Lys Leu Phe
            20                  25                  30

Asn Gly Arg Asp Glu Val Pro Thr Arg Ile Pro Met Leu Asn Ile Ala
        35                  40                  45

Leu Gly Gly Ala Leu Asn Ala Gly Leu Gln Ser Gly Leu Thr Ile Phe
    50                  55                  60

Ala Gly Pro Ser Lys His Phe Lys Thr Leu Phe Gly Leu Thr Met Val
65                  70                  75                  80

Ala Ala Tyr Met Lys Lys Tyr Pro Asp Ala Ile Cys Leu Phe Tyr Asp
                85                  90                  95

Ser Glu Phe Gly Ile Ser Glu Ser Tyr Phe Arg Ser Met Gly Val Asp
            100                 105                 110

Leu Glu Arg Val Val His Thr Pro Ile Gln Ser Val Glu Gln Leu Lys
        115                 120                 125

Val Asp Met Thr Asn Gln Leu Glu Glu Ile Thr Arg Gly Glu Lys Val
    130                 135                 140

Ile Ile Phe Ile Asp Ser Ile Gly Asn Thr Ala Ser Lys Lys Glu Thr
145                 150                 155                 160

Glu Asp Ala Leu Asn Glu Lys Val Val Gly Asp Met Thr Arg Ala Lys
                165                 170                 175

Ser Leu Lys Ser Leu Phe Arg Ile Val Thr Pro Tyr Leu Thr Ile Lys
            180                 185                 190

Asp Ile Pro Cys Val Ala Ile Asn His Thr Ala Met Glu Ile Gly Gly
        195                 200                 205

Met Tyr Pro Lys Glu Ile Met Gly Gly Gly Thr Gly Ile Leu Tyr Ser
```

```
    210                 215                 220

Ala Ser Thr Val Phe Phe Ile Ser Lys Arg Gln Val Lys Asp Gly Thr
225                 230                 235                 240

Glu Leu Thr Gly Tyr Asp Phe Thr Leu Lys Ala Glu Lys Ser Arg Thr
                245                 250                 255

Val Lys Glu Lys Ser Thr Phe Pro Ile Thr Val Asn Phe Glu Gly Gly
            260                 265                 270

Ile Asp Pro Phe Ser Gly Leu Leu Glu Met Ala Thr Glu Ile Gly Phe
        275                 280                 285

Val Val Lys Pro Lys Ala Gly Trp Tyr Asn Arg Ala Phe Leu Asp Glu
    290                 295                 300

Thr Thr Gly Glu Met Val Gln Glu Glu Lys Ser Trp Arg Ala Lys Ala
305                 310                 315                 320

Thr Asp Cys Val Glu Phe Trp Gly Pro Leu Phe Lys His Ala Pro Phe
                325                 330                 335

Arg Ala Ala Ile Glu Asn Lys Tyr Lys Leu Gly Ala Ile Asn Ser Ile
            340                 345                 350

Lys Glu Val Asp Asp Ala Val Asn Asp Leu Ile Asn Ser Arg Val Ser
        355                 360                 365

Lys Asn Val Ala Val Lys Leu Ser Gly Asp Ala Gln Ser Ala Ala Asp
    370                 375                 380

Ile Glu Asn Asp Leu Glu Glu Met Asp Leu Asn Asp
385                 390                 395


<210> SEQ ID NO 5
<211> LENGTH: 398
<212> TYPE: PRT
<213> ORGANISM: Artificial Sequence
<220> FEATURE:
<223> OTHER INFORMATION: Synthetic: VRX_Variant5

<400> SEQUENCE: 5

Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys Ser Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Gly Asp Met Thr Arg
                165                 170                 175

Ala Lys Thr Met Lys Ser Leu Phe Arg Ile Val Thr Pro Phe Phe Ser
```

```
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Phe Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ala Ser Lys
        355                 360                 365

Val Glu Lys Tyr Ser Ala Pro Val Gly Lys Thr Lys Pro Ser Ala Ala
    370                 375                 380

Asp Ile Glu Asn Asp Leu Asp Met Met Glu Asp Leu Asp Glu
385                 390                 395


<210> SEQ ID NO 6
<211> LENGTH: 398
<212> TYPE: PRT
<213> ORGANISM: Artificial Sequence
<220> FEATURE:
<223> OTHER INFORMATION: Synthetic: VRX_Variant6

<400> SEQUENCE: 6

Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys His Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
```

```
145                 150                 155                 160

Glu Thr Glu Asp Ala Leu Asn Glu Lys Val Val Gly Asp Met Thr Arg
                165                 170                 175

Ala Lys Thr Met Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Phe Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ala Ser Lys
        355                 360                 365

Val Glu Lys Tyr Ser Ala Pro Glu Gly Lys Thr Lys Pro Ser Ala Ala
    370                 375                 380

Asp Ile Glu Asn Asp Leu Asp Met Met Glu Asp Leu Asp Glu
385                 390                 395
```

<210> SEQ ID NO 7
<211> LENGTH: 398
<212> TYPE: PRT
<213> ORGANISM: Artificial Sequence
<220> FEATURE:
<223> OTHER INFORMATION: Synthetic: VRX_Var7

<400> SEQUENCE: 7

```
Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys Ser Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
```

```
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Gly Asp Met Thr Arg
                165                 170                 175

Ala Lys Thr Met Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Phe Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Glu Val Val Asp Ala Glu Val Asp Glu Leu Ile Ala Ser Lys
        355                 360                 365

Val Glu Lys Tyr Ser Ala Pro Val Gly Lys Thr Lys Pro Ser Ala Ala
    370                 375                 380

Asp Ile Glu Asn Asp Leu Asp Met Met Glu Asp Leu Asp Glu
385                 390                 395


<210> SEQ ID NO 8
<211> LENGTH: 337
<212> TYPE: PRT
<213> ORGANISM: Artificial Sequence
<220> FEATURE:
<223> OTHER INFORMATION: Synthetic: VRX_Variant8

<400> SEQUENCE: 8

Gly Leu Thr Ile Phe Ala Gly Pro Ser Lys His Phe Lys Ser Asn Met
1               5                   10                  15

Gly Leu Thr Met Val Ser Ala Tyr Met Asn Lys Tyr Pro Glu Ala Ile
            20                  25                  30

Cys Leu Phe Tyr Asp Ser Glu Phe Gly Ile Thr Glu Ala Tyr Leu Arg
        35                  40                  45

Ala Met Lys Val Asp Pro Glu Arg Val Ile His Thr Pro Ile Gln Ser
    50                  55                  60

Val Glu Gln Leu Lys Val Asp Met Val Asn Gln Leu Glu Ala Ile Glu
65                  70                  75                  80

Arg Gly Glu Lys Val Ile Ile Phe Ile Asp Ser Ile Gly Asn Met Ala
```

```
                85                  90                  95

Ser Lys Lys Glu Thr Glu Asp Ala Leu Asn Glu Lys Val Val Ser Asp
            100                 105                 110

Met Thr Arg Ala Lys Thr Met Lys Ser Leu Phe Arg Ile Val Thr Pro
        115                 120                 125

Phe Phe Ser Ile Lys Asp Ile Pro Cys Val Ala Val Asn His Thr Ile
    130                 135                 140

Glu Thr Ile Glu Met Tyr Ser Lys Thr Val Met Thr Gly Gly Thr Gly
145                 150                 155                 160

Val Met Tyr Ser Ala Asp Thr Val Phe Ile Ile Gly Lys Arg Gln Ile
                165                 170                 175

Lys Glu Thr Gly Lys Glu Leu Glu Gly Phe Gln Phe Val Leu Asn Ala
            180                 185                 190

Glu Lys Ser Arg Met Val Lys Glu Lys Ser Lys Phe Phe Ile Asp Val
        195                 200                 205

Lys Phe Asp Gly Gly Ile Asp Pro Tyr Ser Gly Leu Leu Asp Met Ala
    210                 215                 220

Met Glu Ile Gly Phe Val Val Lys Pro Lys Val Gly Trp Tyr Asn Arg
225                 230                 235                 240

Glu Tyr Leu Asp Val Glu Thr Gly Glu Met Val Arg Glu Glu Lys Ser
                245                 250                 255

Trp Arg Ala Lys Asp Thr Asn Cys Thr Glu Phe Trp Gly Pro Leu Phe
            260                 265                 270

Lys His Glu Pro Phe Arg Asp Ala Ile Lys Arg His Tyr Gln Leu Gly
        275                 280                 285

Ala Ile Asp Ser Asn Glu Val Val Asp Ala Glu Val Asp Glu Leu Ile
    290                 295                 300

Ala Ser Lys Val Glu Lys Tyr Ser Ala Pro Glu Gly Lys Thr Lys Pro
305                 310                 315                 320

Ser Ala Ala Asp Ile Glu Asn Asp Leu Asp Met Met Glu Asp Leu Asp
                325                 330                 335

Glu


<210> SEQ ID NO 9
<211> LENGTH: 398
<212> TYPE: PRT
<213> ORGANISM: Artificial Sequence
<220> FEATURE:
<223> OTHER INFORMATION: Synthetic: VRX_Variant9

<400> SEQUENCE: 9

Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys Ser Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110
```

```
Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Gly Asp Met Thr Arg
                165                 170                 175

Ala Lys Ser Leu Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Phe Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ser Ser Lys
        355                 360                 365

Val Glu Lys Tyr Ser Ala Pro Glu Gly Lys Ser Lys Pro Ser Ala Ala
    370                 375                 380

Asp Ile Glu Asn Asp Leu Asp Met Met Glu Asp Leu Asp Glu
385                 390                 395
```

<210> SEQ ID NO 10
<211> LENGTH: 398
<212> TYPE: PRT
<213> ORGANISM: Artificial Sequence
<220> FEATURE:
<223> OTHER INFORMATION: Synthetic: VRX_Variant10

<400> SEQUENCE: 10

```
Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys His Phe Lys Ser Asn Met Gly Leu Thr
65                  70                  75                  80
```

Met Val Ser Ala Tyr Met Asn Lys Tyr Pro Glu Ala Ile Cys Leu Phe
85 90 95

Tyr Asp Ser Glu Phe Gly Ile Thr Glu Ala Tyr Leu Arg Ala Met Lys
100 105 110

Val Asp Pro Glu Arg Val Ile His Thr Pro Ile Gln Ser Val Glu Gln
115 120 125

Leu Lys Val Asp Met Val Asn Gln Leu Glu Ala Ile Glu Arg Gly Glu
130 135 140

Lys Val Ile Ile Phe Ile Asp Ser Ile Gly Asn Met Ala Ser Lys Lys
145 150 155 160

Glu Thr Glu Asp Ala Leu Asn Glu Lys Val Val Ser Asp Met Thr Arg
165 170 175

Ala Lys Ser Leu Lys Ser Leu Phe Arg Ile Val Thr Pro Phe Phe Ser
180 185 190

Ile Lys Asp Ile Pro Cys Val Ala Val Asn His Thr Ile Glu Thr Ile
195 200 205

Glu Met Tyr Ser Lys Thr Val Met Thr Gly Gly Thr Gly Val Met Tyr
210 215 220

Ser Ala Asp Thr Val Phe Ile Ile Gly Lys Arg Gln Ile Lys Glu Thr
225 230 235 240

Gly Lys Glu Leu Glu Gly Phe Gln Phe Val Leu Asn Ala Glu Lys Ser
245 250 255

Arg Met Val Lys Glu Lys Ser Lys Phe Phe Ile Asp Val Lys Phe Asp
260 265 270

Gly Gly Ile Asp Pro Tyr Ser Gly Leu Leu Asp Met Ala Met Glu Ile
275 280 285

Gly Phe Val Val Lys Pro Lys Val Gly Trp Tyr Asn Arg Glu Tyr Leu
290 295 300

Asp Val Glu Thr Gly Glu Met Val Arg Glu Glu Lys Ser Trp Arg Ala
305 310 315 320

Lys Asp Thr Asn Cys Thr Glu Phe Trp Gly Pro Leu Phe Lys His Glu
325 330 335

Pro Phe Arg Asp Ala Ile Lys Arg His Tyr Gln Leu Gly Ala Ile Asp
340 345 350

Ser Asn Ala Val Val Asp Ala Glu Val Asp Glu Leu Ile Ser Ser Lys
355 360 365

Val Glu Lys Tyr Ser Ala Pro Glu Gly Lys Ser Lys Pro Ser Ala Ala
370 375 380

Asp Ile Glu Asn Asp Leu Asp Met Met Glu Asp Leu Asp Glu
385 390 395

<210> SEQ ID NO 11
<211> LENGTH: 398
<212> TYPE: PRT
<213> ORGANISM: Artificial Sequence
<220> FEATURE:
<223> OTHER INFORMATION: Synthetic: VRX_Variant11

<400> SEQUENCE: 11

Met His His His His His His Ser Ile Ala Asp Leu Lys Ser Arg Leu
1 5 10 15

Ile Lys Ala Ser Thr Ser Lys Met Thr Ala Thr Leu Thr Lys Ser Lys
20 25 30

Phe Phe Asn Asp Lys Asp Val Val Arg Thr Lys Ile Pro Met Leu Asn
35 40 45

```
Ile Ala Ile Ser Gly Ala Leu Asp Gly Gly Met Gln Ser Gly Leu Thr
    50                  55                  60

Ile Phe Ala Gly Pro Ser Lys Ser Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Ser Asp Met Thr Arg
                165                 170                 175

Ala Lys Thr Met Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Phe Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ser Ser Lys
        355                 360                 365

Val Glu Lys Tyr Ser Ala Pro Glu Gly Lys Ser Lys Pro Ser Ala Ala
    370                 375                 380

Asp Ile Glu Asn Asp Leu Asp Met Met Glu Asp Leu Asp Glu
385                 390                 395
```

<210> SEQ ID NO 12
<211> LENGTH: 398
<212> TYPE: PRT
<213> ORGANISM: Artificial Sequence
<220> FEATURE:
<223> OTHER INFORMATION: Synthetic: VRX_Variant12

<400> SEQUENCE: 12

```
Met His His His His His His Ser Ile Ala Asp Leu Lys Ser Arg Leu
1               5                   10                  15
```

```
Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys His Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Ser Asp Met Thr Arg
                165                 170                 175

Ala Lys Thr Met Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Phe Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Glu Val Val Asp Ala Glu Val Asp Glu Leu Ile Ser Ser Lys
        355                 360                 365

Val Glu Lys Tyr Ser Ala Pro Glu Gly Lys Ser Lys Pro Ser Ala Ala
    370                 375                 380

Asp Ile Glu Asn Asp Leu Asp Met Met Glu Asp Leu Asp Glu
385                 390                 395
```

<210> SEQ ID NO 13
<211> LENGTH: 398
<212> TYPE: PRT
<213> ORGANISM: Artificial Sequence
<220> FEATURE:

-continued

<223> OTHER INFORMATION: Synthetic: VRX_Variant13

<400> SEQUENCE: 13

```
Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys Ser Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Gly Asp Met Thr Arg
                165                 170                 175

Ala Lys Ser Leu Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Lys Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ala Ser Lys
        355                 360                 365

Val Glu Lys Tyr Ser Ala Pro Val Gly Lys Thr Lys Pro Ser Ala Ala
    370                 375                 380

Asp Ile Glu Asn Asp Leu Asp Met Met Glu Asp Leu Asp Glu
385                 390                 395
```

<210> SEQ ID NO 14
<211> LENGTH: 398
<212> TYPE: PRT
<213> ORGANISM: Artificial Sequence
<220> FEATURE:
<223> OTHER INFORMATION: Synthetic: VRX_Variant14

<400> SEQUENCE: 14

Met His His His His His His Ser Ile Ala Asp Leu Lys Ser Arg Leu
1 5 10 15

Ile Lys Ala Ser Thr Ser Lys Met Thr Ala Thr Leu Thr Lys Ser Lys
20 25 30

Phe Phe Asn Asp Lys Asp Val Val Arg Thr Lys Ile Pro Met Leu Asn
35 40 45

Ile Ala Ile Ser Gly Ala Leu Asp Gly Gly Met Gln Ser Gly Leu Thr
50 55 60

Ile Phe Ala Gly Pro Ser Lys His Phe Lys Ser Asn Met Gly Leu Thr
65 70 75 80

Met Val Ser Ala Tyr Met Asn Lys Tyr Pro Glu Ala Ile Cys Leu Phe
85 90 95

Tyr Asp Ser Glu Phe Gly Ile Thr Glu Ala Tyr Leu Arg Ala Met Lys
100 105 110

Val Asp Pro Glu Arg Val Ile His Thr Pro Ile Gln Ser Val Glu Gln
115 120 125

Leu Lys Val Asp Met Val Asn Gln Leu Glu Ala Ile Glu Arg Gly Glu
130 135 140

Lys Val Ile Ile Phe Ile Asp Ser Ile Gly Asn Met Ala Ser Lys Lys
145 150 155 160

Glu Thr Glu Asp Ala Leu Asn Glu Lys Val Val Gly Asp Met Thr Arg
165 170 175

Ala Lys Ser Leu Lys Ser Leu Phe Arg Ile Val Thr Pro Phe Phe Ser
180 185 190

Ile Lys Asp Ile Pro Cys Val Ala Val Asn His Thr Ile Glu Thr Ile
195 200 205

Glu Met Tyr Ser Lys Thr Val Met Thr Gly Gly Thr Gly Val Met Tyr
210 215 220

Ser Ala Asp Thr Val Phe Ile Ile Gly Lys Arg Gln Ile Lys Glu Thr
225 230 235 240

Gly Lys Glu Leu Glu Gly Phe Gln Phe Val Leu Asn Ala Glu Lys Ser
245 250 255

Arg Met Val Lys Glu Lys Ser Lys Phe Lys Ile Asp Val Lys Phe Asp
260 265 270

Gly Gly Ile Asp Pro Tyr Ser Gly Leu Leu Asp Met Ala Met Glu Ile
275 280 285

Gly Phe Val Val Lys Pro Lys Val Gly Trp Tyr Asn Arg Glu Tyr Leu
290 295 300

Asp Val Glu Thr Gly Glu Met Val Arg Glu Glu Lys Ser Trp Arg Ala
305 310 315 320

Lys Asp Thr Asn Cys Thr Glu Phe Trp Gly Pro Leu Phe Lys His Glu
325 330 335

Pro Phe Arg Asp Ala Ile Lys Arg His Tyr Gln Leu Gly Ala Ile Asp
340 345 350

Ser Asn Ala Val Val Asp Ala Glu Val Asp Glu Leu Ile Ala Ser Lys
355 360 365

```
Val Glu Lys Tyr Ser Ala Pro Val Gly Lys Thr Lys Pro Ser Ala Ala
    370                 375                 380

Asp Ile Glu Asn Asp Leu Asp Met Met Glu Asp Leu Asp Glu
385                 390                 395


<210> SEQ ID NO 15
<211> LENGTH: 398
<212> TYPE: PRT
<213> ORGANISM: Artificial Sequence
<220> FEATURE:
<223> OTHER INFORMATION: Synthetic: VRX_Variant15

<400> SEQUENCE: 15

Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys Ser Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Gly Asp Met Thr Arg
                165                 170                 175

Ala Lys Thr Met Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Lys Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335
```

-continued

Pro Phe Arg Asp Ala Ile Lys Arg His Tyr Gln Leu Gly Ala Ile Asp
340 345 350

Ser Asn Glu Val Val Asp Ala Glu Val Asp Glu Leu Ile Ala Ser Lys
355 360 365

Val Glu Lys Tyr Ser Ala Pro Val Gly Lys Thr Lys Pro Ser Ala Ala
370 375 380

Asp Ile Glu Asn Asp Leu Asp Met Met Glu Asp Leu Asp Glu
385 390 395

<210> SEQ ID NO 16
<211> LENGTH: 398
<212> TYPE: PRT
<213> ORGANISM: Artificial Sequence
<220> FEATURE:
<223> OTHER INFORMATION: Synthetic: VRX_Variant16

<400> SEQUENCE: 16

Met His His His His His His Ser Ile Ala Asp Leu Lys Ser Arg Leu
1 5 10 15

Ile Lys Ala Ser Thr Ser Lys Met Thr Ala Thr Leu Thr Lys Ser Lys
20 25 30

Phe Phe Asn Asp Lys Asp Val Val Arg Thr Lys Ile Pro Met Leu Asn
35 40 45

Ile Ala Ile Ser Gly Ala Leu Asp Gly Gly Met Gln Ser Gly Leu Thr
50 55 60

Ile Phe Ala Gly Pro Ser Lys His Phe Lys Ser Asn Met Gly Leu Thr
65 70 75 80

Met Val Ser Ala Tyr Met Asn Lys Tyr Pro Glu Ala Ile Cys Leu Phe
85 90 95

Tyr Asp Ser Glu Phe Gly Ile Thr Glu Ala Tyr Leu Arg Ala Met Lys
100 105 110

Val Asp Pro Glu Arg Val Ile His Thr Pro Ile Gln Ser Val Glu Gln
115 120 125

Leu Lys Val Asp Met Val Asn Gln Leu Glu Ala Ile Glu Arg Gly Glu
130 135 140

Lys Val Ile Ile Phe Ile Asp Ser Ile Gly Asn Met Ala Ser Lys Lys
145 150 155 160

Glu Thr Glu Asp Ala Leu Asn Glu Lys Val Val Gly Asp Met Thr Arg
165 170 175

Ala Lys Thr Met Lys Ser Leu Phe Arg Ile Val Thr Pro Phe Phe Ser
180 185 190

Ile Lys Asp Ile Pro Cys Val Ala Val Asn His Thr Ile Glu Thr Ile
195 200 205

Glu Met Tyr Ser Lys Thr Val Met Thr Gly Gly Thr Gly Val Met Tyr
210 215 220

Ser Ala Asp Thr Val Phe Ile Ile Gly Lys Arg Gln Ile Lys Glu Thr
225 230 235 240

Gly Lys Glu Leu Glu Gly Phe Gln Phe Val Leu Asn Ala Glu Lys Ser
245 250 255

Arg Met Val Lys Glu Lys Ser Lys Phe Lys Ile Asp Val Lys Phe Asp
260 265 270

Gly Gly Ile Asp Pro Tyr Ser Gly Leu Leu Asp Met Ala Met Glu Ile
275 280 285

Gly Phe Val Val Lys Pro Lys Val Gly Trp Tyr Asn Arg Glu Tyr Leu
290 295 300

Asp Val Glu Thr Gly Glu Met Val Arg Glu Glu Lys Ser Trp Arg Ala
305 310 315 320

Lys Asp Thr Asn Cys Thr Glu Phe Trp Gly Pro Leu Phe Lys His Glu
325 330 335

Pro Phe Arg Asp Ala Ile Lys Arg His Tyr Gln Leu Gly Ala Ile Asp
340 345 350

Ser Asn Glu Val Val Asp Ala Glu Val Asp Glu Leu Ile Ala Ser Lys
355 360 365

Val Glu Lys Tyr Ser Ala Pro Val Gly Lys Thr Lys Pro Ser Ala Ala
370 375 380

Asp Ile Glu Asn Asp Leu Asp Met Met Glu Asp Leu Asp Glu
385 390 395

<210> SEQ ID NO 17
<211> LENGTH: 401
<212> TYPE: PRT
<213> ORGANISM: Artificial Sequence
<220> FEATURE:
<223> OTHER INFORMATION: Synthetic: VRX_Variant17

<400> SEQUENCE: 17

Met His His His His His His Ser Ile Ala Asp Leu Lys Ser Arg Leu
1 5 10 15

Ile Lys Ala Ser Thr Ser Lys Met Thr Ala Thr Leu Thr Lys Ser Lys
20 25 30

Phe Phe Asn Asp Lys Asp Val Val Arg Thr Lys Ile Pro Met Leu Asn
35 40 45

Ile Ala Ile Ser Gly Ala Leu Asp Gly Gly Met Gln Ser Gly Leu Thr
50 55 60

Ile Phe Ala Gly Pro Ser Lys Ser Phe Lys Ser Asn Met Gly Leu Thr
65 70 75 80

Met Val Ser Ala Tyr Met Asn Lys Tyr Pro Glu Ala Ile Cys Leu Phe
85 90 95

Tyr Asp Ser Glu Phe Gly Ile Thr Glu Ala Tyr Leu Arg Ala Met Lys
100 105 110

Val Asp Pro Glu Arg Val Ile His Thr Pro Ile Gln Ser Val Glu Gln
115 120 125

Leu Lys Val Asp Met Val Asn Gln Leu Glu Ala Ile Glu Arg Gly Glu
130 135 140

Lys Val Ile Ile Phe Ile Asp Ser Ile Gly Asn Met Ala Ser Lys Lys
145 150 155 160

Glu Thr Glu Asp Ala Leu Asn Glu Lys Val Val Gly Asp Met Thr Arg
165 170 175

Ala Lys Ser Leu Lys Ser Leu Phe Arg Ile Val Thr Pro Phe Phe Ser
180 185 190

Ile Lys Asp Ile Pro Cys Val Ala Val Asn His Thr Ile Glu Thr Ile
195 200 205

Glu Met Tyr Ser Lys Thr Val Met Thr Gly Gly Thr Gly Val Met Tyr
210 215 220

Ser Ala Asp Thr Val Phe Ile Ile Gly Lys Arg Gln Ile Lys Glu Thr
225 230 235 240

Gly Lys Glu Leu Glu Gly Phe Gln Phe Val Leu Asn Ala Glu Lys Ser
245 250 255

Arg Met Val Lys Glu Lys Ser Lys Phe Lys Ile Asp Val Lys Phe Asp
260 265 270

```
Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ser Ser Lys
        355                 360                 365

Val Glu Lys Tyr Ser Ala Pro Glu Gly Lys Ser Lys Pro Ser Ala Ala
    370                 375                 380

Asp Ile Glu Asn Asp Leu Asp Met Met Glu Asp Leu Asp Glu Leu Asp
385                 390                 395                 400

Glu


<210> SEQ ID NO 18
<211> LENGTH: 401
<212> TYPE: PRT
<213> ORGANISM: Artificial Sequence
<220> FEATURE:
<223> OTHER INFORMATION: Synthetic: VRX_Variant18

<400> SEQUENCE: 18

Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys His Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Ser Asp Met Thr Arg
                165                 170                 175

Ala Lys Ser Leu Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
```

```
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Lys Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ser Ser Lys
        355                 360                 365

Val Glu Lys Tyr Ser Ala Pro Glu Gly Lys Ser Lys Pro Ser Ala Ala
    370                 375                 380

Asp Ile Glu Asn Asp Leu Asp Met Met Glu Asp Leu Asp Glu Leu Asp
385                 390                 395                 400

Glu


<210> SEQ ID NO 19
<211> LENGTH: 398
<212> TYPE: PRT
<213> ORGANISM: Artificial Sequence
<220> FEATURE:
<223> OTHER INFORMATION: Synthetic: VRX_Variant19

<400> SEQUENCE: 19

Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys Ser Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Gly Asp Met Thr Arg
                165                 170                 175

Ala Lys Thr Met Lys Ser Leu Phe Arg Ile Val Thr Pro Phe Phe Ser
            180                 185                 190
```

Ile Lys Asp Ile Pro Cys Val Ala Val Asn His Thr Ile Glu Thr Ile
195 200 205

Glu Met Tyr Ser Lys Thr Val Met Thr Gly Gly Thr Gly Val Met Tyr
210 215 220

Ser Ala Asp Thr Val Phe Ile Ile Gly Lys Arg Gln Ile Lys Glu Thr
225 230 235 240

Gly Lys Glu Leu Glu Gly Phe Gln Phe Val Leu Asn Ala Glu Lys Ser
245 250 255

Arg Met Val Lys Glu Lys Ser Lys Phe Lys Ile Asp Val Lys Phe Asp
260 265 270

Gly Gly Ile Asp Pro Tyr Ser Gly Leu Leu Asp Met Ala Met Glu Ile
275 280 285

Gly Phe Val Val Lys Pro Lys Val Gly Trp Tyr Asn Arg Glu Tyr Leu
290 295 300

Asp Val Glu Thr Gly Glu Met Val Arg Glu Glu Lys Ser Trp Arg Ala
305 310 315 320

Lys Asp Thr Asn Cys Thr Glu Phe Trp Gly Pro Leu Phe Lys His Glu
325 330 335

Pro Phe Arg Asp Ala Ile Lys Arg His Tyr Gln Leu Gly Ala Ile Asp
340 345 350

Ser Asn Glu Val Val Asp Ala Glu Val Asp Glu Leu Ile Ser Ser Lys
355 360 365

Val Glu Lys Tyr Ser Ala Pro Glu Gly Lys Ser Lys Pro Ser Ala Ala
370 375 380

Asp Ile Glu Asn Asp Leu Asp Met Met Glu Asp Leu Asp Glu
385 390 395

<210> SEQ ID NO 20
<211> LENGTH: 401
<212> TYPE: PRT
<213> ORGANISM: Artificial Sequence
<220> FEATURE:
<223> OTHER INFORMATION: Synthetic: VRX_Variant20

<400> SEQUENCE: 20

Met His His His His His His Ser Ile Ala Asp Leu Lys Ser Arg Leu
1 5 10 15

Ile Lys Ala Ser Thr Ser Lys Met Thr Ala Thr Leu Thr Lys Ser Lys
20 25 30

Phe Phe Asn Asp Lys Asp Val Val Arg Thr Lys Ile Pro Met Leu Asn
35 40 45

Ile Ala Ile Ser Gly Ala Leu Asp Gly Gly Met Gln Ser Gly Leu Thr
50 55 60

Ile Phe Ala Gly Pro Ser Lys His Phe Lys Ser Asn Met Gly Leu Thr
65 70 75 80

Met Val Ser Ala Tyr Met Asn Lys Tyr Pro Glu Ala Ile Cys Leu Phe
85 90 95

Tyr Asp Ser Glu Phe Gly Ile Thr Glu Ala Tyr Leu Arg Ala Met Lys
100 105 110

Val Asp Pro Glu Arg Val Ile His Thr Pro Ile Gln Ser Val Glu Gln
115 120 125

Leu Lys Val Asp Met Val Asn Gln Leu Glu Ala Ile Glu Arg Gly Glu
130 135 140

Lys Val Ile Ile Phe Ile Asp Ser Ile Gly Asn Met Ala Ser Lys Lys
145 150 155 160

```
Glu Thr Glu Asp Ala Leu Asn Glu Lys Val Val Ser Asp Met Thr Arg
                165                 170                 175

Ala Lys Thr Met Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Lys Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Glu Val Val Asp Ala Glu Val Asp Glu Leu Ile Ser Ser Lys
        355                 360                 365

Val Glu Lys Tyr Ser Ala Pro Glu Gly Lys Ser Lys Pro Ser Ala Ala
    370                 375                 380

Asp Ile Glu Asn Asp Leu Asp Met Met Glu Asp Leu Asp Glu Leu Asp
385                 390                 395                 400

Glu


<210> SEQ ID NO 21
<211> LENGTH: 396
<212> TYPE: PRT
<213> ORGANISM: Artificial Sequence
<220> FEATURE:
<223> OTHER INFORMATION: Synthetic: VR7_25X_NHis

<400> SEQUENCE: 21

Met His His His His His His Ser Asp Leu Lys Ser Arg Leu Ile Lys
1               5                   10                  15

Ala Ser Thr Ser Lys Met Thr Ala Asp Leu Thr Lys Ser Lys Leu Phe
            20                  25                  30

Asn Gly Arg Asp Glu Val Pro Thr Arg Ile Pro Met Leu Asn Ile Ala
        35                  40                  45

Leu Gly Gly Ala Leu Asn Ala Gly Leu Gln Ser Gly Leu Thr Ile Phe
    50                  55                  60

Ala Ala Pro Ser Lys His Phe Lys Thr Leu Phe Gly Leu Thr Met Val
65                  70                  75                  80

Ala Ala Tyr Met Lys Lys Tyr Pro Asp Ala Ile Cys Leu Phe Tyr Asp
                85                  90                  95

Ser Glu Phe Gly Ala Ser Glu Ser Tyr Phe Arg Ser Met Gly Val Asp
            100                 105                 110
```

```
Leu Glu Arg Val Val His Thr Pro Ile Gln Ser Val Glu Gln Leu Lys
        115                 120                 125

Val Asp Met Thr Asn Gln Leu Glu Glu Ile Thr Arg Gly Glu Lys Val
    130                 135                 140

Ile Ile Phe Ile Asp Ser Ile Gly Asn Thr Ala Ser Lys Lys Glu Thr
145                 150                 155                 160

Glu Asp Ala Leu Asn Glu Lys Val Val Gly Asp Met Thr Arg Ala Lys
                165                 170                 175

Ser Leu Lys Ser Leu Phe Arg Ile Val Thr Pro Tyr Leu Thr Ile Lys
            180                 185                 190

Asp Ile Pro Cys Val Ala Ile Asn His Thr Ala Met Glu Ile Gly Gly
        195                 200                 205

Met Tyr Pro Lys Glu Ile Met Gly Gly Gly Thr Gly Ile Leu Tyr Ser
    210                 215                 220

Ala Ser Thr Val Phe Phe Ile Ser Lys Arg Gln Val Lys Asp Gly Thr
225                 230                 235                 240

Glu Leu Thr Gly Tyr Asp Phe Thr Leu Lys Ala Glu Lys Ser Arg Thr
                245                 250                 255

Val Lys Glu Lys Ser Thr Phe Pro Ile Thr Val Asn Phe Glu Gly Gly
            260                 265                 270

Ile Asp Pro Phe Ser Gly Leu Leu Glu Met Ala Thr Glu Ile Gly Phe
        275                 280                 285

Val Val Lys Pro Lys Ala Gly Trp Tyr Asn Arg Ala Phe Leu Asp Glu
    290                 295                 300

Thr Thr Gly Glu Met Val Gln Glu Glu Lys Ser Trp Arg Ala Lys Ala
305                 310                 315                 320

Thr Asp Cys Val Glu Phe Trp Gly Pro Leu Phe Lys His Ala Pro Phe
                325                 330                 335

Arg Ala Ala Ile Glu Asn Lys Tyr Lys Leu Gly Ala Ile Asn Ser Ile
            340                 345                 350

Lys Glu Val Asp Asp Ala Val Asn Asp Leu Ile Asn Ser Arg Val Ser
        355                 360                 365

Lys Asn Val Ala Val Lys Leu Ser Gly Asp Ala Gln Ser Ala Ala Asp
    370                 375                 380

Ile Glu Asn Asp Leu Glu Glu Met Asp Leu Asn Asp
385                 390                 395


<210> SEQ ID NO 22
<211> LENGTH: 398
<212> TYPE: PRT
<213> ORGANISM: Artificial Sequence
<220> FEATURE:
<223> OTHER INFORMATION: Synthetic: VR7_25X_NHis

<400> SEQUENCE: 22

Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45

Ile Ala Ile Ser Gly Ala Leu Asp Gly Gly Met Gln Ser Gly Leu Thr
    50                  55                  60

Ile Phe Ala Gly Pro Ser Lys His Phe Lys Ser Asn Met Gly Leu Thr
65                  70                  75                  80
```

```
Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Gly Asp Met Thr Arg
                165                 170                 175

Ala Lys Ser Leu Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Phe Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ala Ser Lys
        355                 360                 365

Val Glu Lys Tyr Ser Ala Pro Val Gly Lys Thr Lys Pro Ser Ala Ala
    370                 375                 380

Asp Ile Glu Asn Asp Leu Asp Met Met Glu Asp Leu Asp Glu
385                 390                 395


<210> SEQ ID NO 23
<211> LENGTH: 398
<212> TYPE: PRT
<213> ORGANISM: Artificial Sequence
<220> FEATURE:
<223> OTHER INFORMATION: Synthetic: VR20_26X_NHis

<400> SEQUENCE: 23

Met His His His His His His Ser Ile Ala Asp Leu Lys Ser Arg Leu
1               5                   10                  15

Ile Lys Ala Ser Thr Ser Lys Met Thr Ala Thr Leu Thr Lys Ser Lys
            20                  25                  30

Phe Phe Asn Asp Lys Asp Val Val Arg Thr Lys Ile Pro Met Leu Asn
        35                  40                  45
```

```
Ile Ala Ile Ser Gly Ala Leu Asp Gly Gly Met Gln Ser Gly Leu Thr
    50                  55                  60

Ile Phe Ala Gly Pro Ser Lys His Phe Lys Ser Asn Met Gly Leu Thr
65                  70                  75                  80

Met Val Ser Ala Tyr Met Asn Lys Tyr Pro Glu Ala Ile Cys Leu Phe
                85                  90                  95

Tyr Asp Ser Glu Phe Gly Ile Thr Glu Ala Tyr Leu Arg Ala Met Lys
            100                 105                 110

Val Asp Pro Glu Arg Val Ile His Thr Pro Ile Gln Ser Val Glu Gln
        115                 120                 125

Leu Lys Val Asp Met Val Asn Gln Leu Glu Ala Ile Glu Arg Gly Glu
    130                 135                 140

Lys Val Ile Ile Phe Ile Asp Ser Ile Gly Asn Met Ala Ser Lys Lys
145                 150                 155                 160

Glu Thr Glu Asp Ala Leu Asn Glu Lys Val Val Gly Asp Met Thr Arg
                165                 170                 175

Ala Lys Ser Leu Lys Ser Leu Phe Arg Ile Val Thr Pro Phe Phe Ser
            180                 185                 190

Ile Lys Asp Ile Pro Cys Val Ala Val Asn His Thr Ile Glu Thr Ile
        195                 200                 205

Glu Met Tyr Ser Lys Thr Val Met Thr Gly Gly Thr Gly Val Met Tyr
    210                 215                 220

Ser Ala Asp Thr Val Phe Ile Ile Gly Lys Arg Gln Ile Lys Glu Thr
225                 230                 235                 240

Gly Lys Glu Leu Glu Gly Phe Gln Phe Val Leu Asn Ala Glu Lys Ser
                245                 250                 255

Arg Met Val Lys Glu Lys Ser Lys Phe Phe Ile Asp Val Lys Phe Asp
            260                 265                 270

Gly Gly Ile Asp Pro Tyr Ser Gly Leu Leu Asp Met Ala Met Glu Ile
        275                 280                 285

Gly Phe Val Val Lys Pro Lys Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ser Ser Lys
        355                 360                 365

Val Glu Lys Tyr Ser Ala Pro Glu Gly Lys Ser Lys Pro Ser Ala Ala
    370                 375                 380

Asp Ile Glu Asn Asp Leu Asp Met Met Glu Asp Leu Asp Glu
385                 390                 395


<210> SEQ ID NO 24
<211> LENGTH: 309
<212> TYPE: PRT
<213> ORGANISM: Artificial Sequence
<220> FEATURE:
<223> OTHER INFORMATION: Synthetic: VR5G_NHis

<400> SEQUENCE: 24

Met His His His His His His Ser Met Phe Lys Arg Arg Asp Pro Ser
1               5                   10                  15
```

```
Gln Leu Ala Ala Gln Leu Asn Ala Leu Lys Gly Gly Ser Ser Phe Ser
            20                  25                  30

Ser Asp Asp Lys Ser Glu Trp Lys Leu Lys Asp Asp Asn Gly Val Gly
        35                  40                  45

Thr Ala Val Ile Arg Phe Leu Pro Ser Lys Asp Glu Ala Asn Pro Ser
    50                  55                  60

Pro Phe Val Lys Leu Val Asn His Gly Phe Lys Lys Asn Gly Gln Trp
65                  70                  75                  80

Tyr Ile Glu Ser Cys Thr Ser Thr His Gly Asp Phe Asp Ser Cys Pro
                85                  90                  95

Val Cys Lys Tyr Met Asn Gln Asn Asp Ser Phe Asn Thr Asn Asn Ala
            100                 105                 110

Glu Tyr Lys Leu Met Lys Arg Lys Thr Ser Phe Trp Ala Asn Ile Leu
        115                 120                 125

Val Ile Lys Asp Ser Ala Val Pro Ala Asn Glu Gly Lys Val Phe Lys
    130                 135                 140

Phe Arg Phe Gly Gln Lys Ile Met Asp Lys Ile Asn Gln Met Val Glu
145                 150                 155                 160

Val Asp Thr Asp Ile Gly Glu Thr Pro Ile Asp Val Thr Cys Pro Phe
                165                 170                 175

Asp Gly Ala Asn Phe Val Leu Lys Ser Lys Lys Val Gly Asp Phe Lys
            180                 185                 190

Asn Tyr Asp Asp Ser Lys Phe Met Asn Gln Ser Glu Ile Pro Asn Ile
        195                 200                 205

Asn Asp Glu Ala Tyr Gln Ala Lys Leu Met Glu Glu Met His Asp Leu
    210                 215                 220

Ser Lys Leu Leu Glu Phe Lys Ser Phe Glu Thr Asn Glu Ala Lys Phe
225                 230                 235                 240

Lys Lys Val Val Gly Thr Ala Ala Leu Gly Gly Ala Ala Ala Lys Ala
                245                 250                 255

Ser Ala Ala Ala Asp Lys Ile Gly Asp Asp Leu Asp Ala Phe Ser Ala
            260                 265                 270

Asp Leu Asp Ala Tyr Asp Ser Lys Pro Ser Thr Pro Ala Arg Ser Thr
        275                 280                 285

Thr Pro Glu Pro Ser Val Ser Pro Ser Asp Asp Asp Gly Leu Asp Asp
    290                 295                 300

Leu Leu Ala Gly Leu
305
```

<210> SEQ ID NO 25
<211> LENGTH: 307
<212> TYPE: PRT
<213> ORGANISM: Artificial Sequence
<220> FEATURE:
<223> OTHER INFORMATION: Synthetic: VR7G_NHis

<400> SEQUENCE: 25

```
Met His His His His His His Phe Lys Arg Arg Asn Pro Ala Asp Leu
1               5                   10                  15

Ala Ala Ser Leu Asn Ala Leu Lys Gly Gly Ala Gly Phe Ser Ser Asp
            20                  25                  30

Asp Lys Lys Glu Trp Lys Leu Lys Asp Thr Asp Gly Val Gly Ser Ala
        35                  40                  45

Val Ile Arg Phe Leu Pro Ser Lys Asn Glu Glu Asn Pro Ser Pro Phe
    50                  55                  60
```

Ile Lys Leu Val Asn His Gly Phe Lys Asn Ala Gly Gln Trp Tyr Ile
65 70 75 80

Glu Asn Cys Thr Ser Thr His Gly Asp Tyr Glu Asn Cys Pro Val Cys
85 90 95

Ala Tyr Met Asn Lys Asn Asp Leu Tyr Asn Thr Asn Glu Ser Glu Tyr
100 105 110

Arg Lys Leu Lys Arg Asn Thr Ser Tyr Trp Ala Asn Ile Leu Val Ile
115 120 125

Lys Asp Pro Ala Val Pro Ser Asn Glu Gly Gln Val Phe Lys Tyr Arg
130 135 140

Phe Gly Lys Lys Ile Met Asp Lys Ile Asn Gln Met Val Glu Val Asp
145 150 155 160

Val Asp Met Gly Glu Thr Ala Ile Asp Val Thr Cys Pro Phe Glu Gly
165 170 175

Ala Asn Phe Val Leu Lys Ser Lys Met Val Ser Gly Tyr Lys Asn Tyr
180 185 190

Asp Asp Ser Lys Phe Met Asn Gln Ser Glu Ile Ala Gly Ile Asn Asp
195 200 205

Glu Ala Phe Gln Lys Lys Leu Trp Asp Glu Met Ser Asp Leu Asn Glu
210 215 220

Leu Leu Val Phe Lys Ser Leu Glu Glu Asn Gln Lys Lys Phe Ser Lys
225 230 235 240

Val Met Gly Thr Ala Ala Leu Gly Gly Ala Ala Ser Lys Ala Ala Ala
245 250 255

Gln Ala Asp Lys Leu Gly Ala Asp Leu Asp Asp Phe Asp Lys Asp Met
260 265 270

Glu Asp Phe Thr Ser Asn Lys Pro Ala Lys Ser Glu Arg Thr Ala Thr
275 280 285

Ala Pro Ser Thr Pro Glu Pro Ser Asp Asp Gly Leu Asp Asp Leu Leu
290 295 300

Ala Gly Leu
305

<210> SEQ ID NO 26
<211> LENGTH: 309
<212> TYPE: PRT
<213> ORGANISM: Artificial Sequence
<220> FEATURE:
<223> OTHER INFORMATION: Synthetic: VR25G_NHis

<400> SEQUENCE: 26

Met His His His His His His Ser Met Phe Lys Arg Lys Asn Pro Ala
1 5 10 15

Asp Leu Ala Ala Ser Leu Asn Ala Leu Lys Gly Gly Ser Gly Phe Ser
20 25 30

Ser Asp Asp Lys Lys Glu Trp Lys Leu Lys Asp Thr Asp Gly Val Gly
35 40 45

Ser Ala Val Ile Arg Phe Leu Pro Ser Lys Asn Glu Glu Asn Pro Ser
50 55 60

Pro Phe Ile Lys Leu Val Asn His Gly Phe Lys Asn Ala Gly Gln Trp
65 70 75 80

Tyr Ile Glu Asn Cys Thr Ser Thr His Gly Asp Tyr Glu Asn Cys Pro
85 90 95

Val Cys Ala Tyr Met Asn Lys Asn Asp Leu Tyr Asn Thr Asn Glu Ser
100 105 110

```
Glu Tyr Arg Lys Leu Lys Arg Asn Thr Ser Tyr Trp Ala Asn Ile Leu
        115                 120                 125

Val Ile Lys Asp Pro Ala Val Pro Ser Asn Glu Gly Gln Val Phe Lys
    130                 135                 140

Tyr Arg Phe Gly Lys Lys Ile Met Asp Lys Ile Asn Gln Met Val Glu
145                 150                 155                 160

Val Asp Val Asp Met Gly Glu Thr Ala Ile Asp Val Thr Cys Pro Phe
                165                 170                 175

Glu Gly Ala Asn Phe Val Leu Lys Ser Lys Met Val Ser Gly Tyr Lys
            180                 185                 190

Asn Tyr Asp Asp Ser Lys Phe Met Asn Gln Ser Glu Ile Ala Gly Ile
        195                 200                 205

Asn Asp Glu Ala Phe Gln Lys Lys Leu Trp Asp Glu Met Ser Asp Leu
    210                 215                 220

Asn Glu Leu Leu Val Phe Lys Ser Leu Glu Glu Asn Gln Lys Lys Phe
225                 230                 235                 240

Ser Lys Val Met Gly Thr Ala Ala Leu Gly Gly Ala Ala Ser Lys Ala
                245                 250                 255

Ala Ala Gln Ala Asp Lys Leu Gly Ala Asp Leu Asp Asp Phe Asp Lys
            260                 265                 270

Asp Met Glu Asp Phe Thr Ser Ser Lys Pro Ala Lys Ser Glu Arg Thr
        275                 280                 285

Ala Thr Ala Pro Ser Thr Pro Glu Pro Ser Asp Asp Gly Leu Asp Asp
    290                 295                 300

Leu Leu Ala Gly Leu
305
```

<210> SEQ ID NO 27
<211> LENGTH: 150
<212> TYPE: PRT
<213> ORGANISM: Artificial Sequence
<220> FEATURE:
<223> OTHER INFORMATION: Synthetic: VR5Y_NHis

<400> SEQUENCE: 27

```
Met His His His His His His Ser Lys Glu Ile Glu Tyr Lys Leu Glu
1               5                   10                  15

Ser Phe Gln Asp Ala Leu Asp Glu Asp Leu Lys Ile Asp Gly Thr Arg
            20                  25                  30

Leu Gln Tyr Glu Val Gln Asn Asn Val Leu Leu His Ser Lys Trp Leu
        35                  40                  45

Arg Leu Tyr Thr Asn Cys Lys Lys Glu Ile Met Arg Leu Glu Ile Gln
    50                  55                  60

Lys Lys Thr Ser Leu Lys Lys Arg Leu Asp Phe Tyr Thr Gly Arg Gly
65                  70                  75                  80

Glu Pro Gly Asp Glu Val Cys Met Asp Gln Tyr Glu Lys Ser Glu Leu
                85                  90                  95

Lys Thr Val Met Ala Ala Asp Ser Ser Val Ile Lys Ile Asp Thr Ser
            100                 105                 110

Ile Gln Tyr Trp Ala Leu Leu Gln Asp Phe Cys Ser Ser Ala Leu Asp
        115                 120                 125

Ala Ile Lys Ala Arg Gly Phe Asn Leu Lys Thr Met His Glu Met Arg
    130                 135                 140

Gln Phe Glu Ala Gly Lys
145                 150
```

<210> SEQ ID NO 28
<211> LENGTH: 150
<212> TYPE: PRT
<213> ORGANISM: Artificial Sequence
<220> FEATURE:
<223> OTHER INFORMATION: Synthetic: VR7_25_26Y_NHis

<400> SEQUENCE: 28

```
Met His His His His His His Lys Thr Glu Ile Glu Tyr Lys Leu Glu
1               5                   10                  15

Val Phe Gln Asp Glu Leu Asp Ala Asp Leu Lys Ile Asp Gly Thr Gln
            20                  25                  30

Ile Gln Tyr Glu Thr Gln Asn Asn Val Leu Leu His Ser Lys Trp Leu
        35                  40                  45

Arg Leu Tyr Thr Asn Cys Lys Lys Glu Ile Met Arg Leu Glu Ile Gln
    50                  55                  60

Lys Lys Thr Ala Leu Lys Lys Arg Leu Asp His Tyr Thr Gly Arg Gly
65                  70                  75                  80

Asp Pro Gly Glu Glu Val Cys Met Asp Val Tyr Glu Lys Ser Glu Leu
                85                  90                  95

Lys Thr Val Met Ala Ala Asp Ser Ser Val Leu Lys Ile Asp Thr Ser
            100                 105                 110

Ile Gln Tyr Trp Ala Leu Leu Gln Asp Phe Cys Ser Ala Ala Leu Asp
        115                 120                 125

Gly Val Lys Ser Arg Ser Phe Ala Leu Lys His Met Leu Glu Ile Arg
    130                 135                 140

Gln Phe Glu Ala Gly Lys
145                 150
```

<210> SEQ ID NO 29
<211> LENGTH: 150
<212> TYPE: PRT
<213> ORGANISM: Artificial Sequence
<220> FEATURE:
<223> OTHER INFORMATION: Synthetic: VR20Y_NHis

<400> SEQUENCE: 29

```
Met His His His His His His Lys Lys Glu Ile Glu Tyr Lys Leu Glu
1               5                   10                  15

Val Phe Gln Asp Glu Leu Asp Ala Asp Leu Lys Ile Asp Gly Thr Gln
            20                  25                  30

Leu Gln Tyr Glu Thr Gln Asn Asn Val Leu Leu His Ser Lys Trp Leu
        35                  40                  45

Arg Leu Tyr Thr Asn Cys Lys Lys Glu Ile Met Arg Leu Glu Ile Gln
    50                  55                  60

Lys Lys Thr Ala Leu Lys Lys Arg Leu Asp His Tyr Thr Gly Arg Gly
65                  70                  75                  80

Asp Pro Gly Glu Glu Val Cys Met Asp Val Tyr Glu Lys Ser Glu Leu
                85                  90                  95

Lys Thr Val Met Ala Ala Asp Ser Ser Val Leu Lys Ile Asp Thr Ser
            100                 105                 110

Ile Gln Tyr Trp Ala Leu Leu Gln Asp Phe Cys Ser Ala Ala Leu Asp
        115                 120                 125

Gly Val Lys Ser Arg Ser Phe Ala Leu Lys His Met Leu Glu Ile Arg
    130                 135                 140

Gln Phe Glu Ala Gly Lys
145                 150
```

<210> SEQ ID NO 30
<211> LENGTH: 398
<212> TYPE: PRT
<213> ORGANISM: Artificial Sequence
<220> FEATURE:
<223> OTHER INFORMATION: Synthetic: VR7_25X_CHis

<400> SEQUENCE: 30

Met Ser Ile Ala Asp Leu Lys Ser Arg Leu Ile Lys Ala Ser Thr Ser
1 5 10 15

Lys Met Thr Ala Thr Leu Thr Lys Ser Lys Phe Phe Asn Asp Lys Asp
20 25 30

Val Val Arg Thr Lys Ile Pro Met Leu Asn Ile Ala Ile Ser Gly Ala
35 40 45

Leu Asp Gly Gly Met Gln Ser Gly Leu Thr Ile Phe Ala Gly Pro Ser
50 55 60

Lys His Phe Lys Ser Asn Met Gly Leu Thr Met Val Ser Ala Tyr Met
65 70 75 80

Asn Lys Tyr Pro Glu Ala Ile Cys Leu Phe Tyr Asp Ser Glu Phe Gly
85 90 95

Ile Thr Glu Ala Tyr Leu Arg Ala Met Lys Val Asp Pro Glu Arg Val
100 105 110

Ile His Thr Pro Ile Gln Ser Val Glu Gln Leu Lys Val Asp Met Val
115 120 125

Asn Gln Leu Glu Ala Ile Glu Arg Gly Glu Lys Val Ile Ile Phe Ile
130 135 140

Asp Ser Ile Gly Asn Met Ala Ser Lys Lys Glu Thr Glu Asp Ala Leu
145 150 155 160

Asn Glu Lys Val Val Gly Asp Met Thr Arg Ala Lys Ser Leu Lys Ser
165 170 175

Leu Phe Arg Ile Val Thr Pro Phe Phe Ser Ile Lys Asp Ile Pro Cys
180 185 190

Val Ala Val Asn His Thr Ile Glu Thr Ile Glu Met Tyr Ser Lys Thr
195 200 205

Val Met Thr Gly Gly Thr Gly Val Met Tyr Ser Ala Asp Thr Val Phe
210 215 220

Ile Ile Gly Lys Arg Gln Ile Lys Glu Thr Gly Lys Glu Leu Glu Gly
225 230 235 240

Phe Gln Phe Val Leu Asn Ala Glu Lys Ser Arg Met Val Lys Glu Lys
245 250 255

Ser Lys Phe Phe Ile Asp Val Lys Phe Asp Gly Gly Ile Asp Pro Tyr
260 265 270

Ser Gly Leu Leu Asp Met Ala Met Glu Ile Gly Phe Val Val Lys Pro
275 280 285

Lys Val Gly Trp Tyr Asn Arg Glu Tyr Leu Asp Val Glu Thr Gly Glu
290 295 300

Met Val Arg Glu Glu Lys Ser Trp Arg Ala Lys Asp Thr Asn Cys Thr
305 310 315 320

Glu Phe Trp Gly Pro Leu Phe Lys His Glu Pro Phe Arg Asp Ala Ile
325 330 335

Lys Arg His Tyr Gln Leu Gly Ala Ile Asp Ser Asn Ala Val Val Asp
340 345 350

Ala Glu Val Asp Glu Leu Ile Ala Ser Lys Val Glu Lys Tyr Ser Ala
355 360 365

```
Pro Val Gly Lys Thr Lys Pro Ser Ala Ala Asp Ile Glu Asn Asp Leu
    370                 375                 380

Asp Met Met Glu Asp Leu Asp Glu His His His His His His
385                 390                 395


<210> SEQ ID NO 31
<211> LENGTH: 307
<212> TYPE: PRT
<213> ORGANISM: Artificial Sequence
<220> FEATURE:
<223> OTHER INFORMATION: Synthetic: VR7G_CHis

<400> SEQUENCE: 31

Met Phe Lys Arg Arg Asn Pro Ala Asp Leu Ala Ala Ser Leu Asn Ala
1               5                   10                  15

Leu Lys Gly Gly Ala Gly Phe Ser Ser Asp Asp Lys Lys Glu Trp Lys
            20                  25                  30

Leu Lys Asp Thr Asp Gly Val Gly Ser Ala Val Ile Arg Phe Leu Pro
        35                  40                  45

Ser Lys Asn Glu Glu Asn Pro Ser Pro Phe Ile Lys Leu Val Asn His
    50                  55                  60

Gly Phe Lys Asn Ala Gly Gln Trp Tyr Ile Glu Asn Cys Thr Ser Thr
65                  70                  75                  80

His Gly Asp Tyr Glu Asn Cys Pro Val Cys Ala Tyr Met Asn Lys Asn
                85                  90                  95

Asp Leu Tyr Asn Thr Asn Glu Ser Glu Tyr Arg Lys Leu Lys Arg Asn
            100                 105                 110

Thr Ser Tyr Trp Ala Asn Ile Leu Val Ile Lys Asp Pro Ala Val Pro
        115                 120                 125

Ser Asn Glu Gly Gln Val Phe Lys Tyr Arg Phe Gly Lys Lys Ile Met
    130                 135                 140

Asp Lys Ile Asn Gln Met Val Glu Val Asp Val Asp Met Gly Glu Thr
145                 150                 155                 160

Ala Ile Asp Val Thr Cys Pro Phe Glu Gly Ala Asn Phe Val Leu Lys
                165                 170                 175

Ser Lys Met Val Ser Gly Tyr Lys Asn Tyr Asp Asp Ser Lys Phe Met
            180                 185                 190

Asn Gln Ser Glu Ile Ala Gly Ile Asn Asp Glu Ala Phe Gln Lys Lys
        195                 200                 205

Leu Trp Asp Glu Met Ser Asp Leu Asn Glu Leu Leu Val Phe Lys Ser
    210                 215                 220

Leu Glu Glu Asn Gln Lys Lys Phe Ser Lys Val Met Gly Thr Ala Ala
225                 230                 235                 240

Leu Gly Gly Ala Ala Ser Lys Ala Ala Ala Gln Ala Asp Lys Leu Gly
                245                 250                 255

Ala Asp Leu Asp Asp Phe Asp Lys Asp Met Glu Asp Phe Thr Ser Asn
            260                 265                 270

Lys Pro Ala Lys Ser Glu Arg Thr Ala Thr Ala Pro Ser Thr Pro Glu
        275                 280                 285

Pro Ser Asp Asp Gly Leu Asp Asp Leu Leu Ala Gly Leu His His His
    290                 295                 300

His His His
305


<210> SEQ ID NO 32
```

<211> LENGTH: 150
<212> TYPE: PRT
<213> ORGANISM: Artificial Sequence
<220> FEATURE:
<223> OTHER INFORMATION: Synthetic: VR7_25_26Y_CHis

<400> SEQUENCE: 32

Met Lys Thr Glu Ile Glu Tyr Lys Leu Glu Val Phe Gln Asp Glu Leu
1 5 10 15

Asp Ala Asp Leu Lys Ile Asp Gly Thr Gln Ile Gln Tyr Glu Thr Gln
20 25 30

Asn Asn Val Leu Leu His Ser Lys Trp Leu Arg Leu Tyr Thr Asn Cys
35 40 45

Lys Lys Glu Ile Met Arg Leu Glu Ile Gln Lys Lys Thr Ala Leu Lys
50 55 60

Lys Arg Leu Asp His Tyr Thr Gly Arg Gly Asp Pro Gly Glu Glu Val
65 70 75 80

Cys Met Asp Val Tyr Glu Lys Ser Glu Leu Lys Thr Val Met Ala Ala
85 90 95

Asp Ser Ser Val Leu Lys Ile Asp Thr Ser Ile Gln Tyr Trp Ala Leu
100 105 110

Leu Gln Asp Phe Cys Ser Ala Ala Leu Asp Gly Val Lys Ser Arg Ser
115 120 125

Phe Ala Leu Lys His Met Leu Glu Ile Arg Gln Phe Glu Ala Gly Lys
130 135 140

His His His His His His
145 150

<210> SEQ ID NO 33
<211> LENGTH: 397
<212> TYPE: PRT
<213> ORGANISM: Artificial Sequence
<220> FEATURE:
<223> OTHER INFORMATION: Synthetic: Phage_T4_uvsX

<400> SEQUENCE: 33

Met His His His His His His Ser Asp Leu Lys Ser Arg Leu Ile Lys
1 5 10 15

Ala Ser Thr Ser Lys Leu Thr Ala Glu Leu Thr Ala Ser Lys Phe Phe
20 25 30

Asn Glu Lys Asp Val Val Arg Thr Lys Ile Pro Met Met Asn Ile Ala
35 40 45

Leu Ser Gly Glu Ile Thr Gly Gly Met Gln Ser Gly Leu Leu Ile Leu
50 55 60

Ala Gly Pro Ser Lys Ser Phe Lys Ser Asn Phe Gly Leu Thr Met Val
65 70 75 80

Ser Ser Tyr Met Arg Gln Tyr Pro Asp Ala Val Cys Leu Phe Tyr Asp
85 90 95

Ser Glu Phe Gly Ile Thr Pro Ala Tyr Leu Arg Ser Met Gly Val Asp
100 105 110

Pro Glu Arg Val Ile His Thr Pro Val Gln Ser Leu Glu Gln Leu Arg
115 120 125

Ile Asp Met Val Asn Gln Leu Asp Ala Ile Glu Arg Gly Glu Lys Val
130 135 140

Val Val Phe Ile Asp Ser Leu Gly Asn Leu Ala Ser Lys Lys Glu Thr
145 150 155 160

Glu Asp Ala Leu Asn Glu Lys Val Val Ser Asp Met Thr Arg Ala Lys

```
                165                 170                 175

Thr Met Lys Ser Leu Phe Arg Ile Val Thr Pro Tyr Phe Ser Thr Lys
            180                 185                 190

Asn Ile Pro Cys Ile Ala Ile Asn His Thr Tyr Glu Thr Gln Glu Met
        195                 200                 205

Phe Ser Lys Thr Val Met Gly Gly Gly Thr Gly Pro Met Tyr Ser Ala
    210                 215                 220

Asp Thr Val Phe Ile Ile Gly Lys Arg Gln Ile Lys Asp Gly Ser Asp
225                 230                 235                 240

Leu Gln Gly Tyr Gln Phe Val Leu Asn Val Glu Lys Ser Arg Thr Val
                245                 250                 255

Lys Glu Lys Ser Lys Phe Phe Ile Asp Val Lys Phe Asp Gly Gly Ile
            260                 265                 270

Asp Pro Tyr Ser Gly Leu Leu Asp Met Ala Leu Glu Leu Gly Phe Val
        275                 280                 285

Val Lys Pro Lys Asn Gly Trp Tyr Ala Arg Glu Phe Leu Asp Glu Glu
    290                 295                 300

Thr Gly Glu Met Ile Arg Glu Glu Lys Ser Trp Arg Ala Lys Asp Thr
305                 310                 315                 320

Asn Cys Thr Thr Phe Trp Gly Pro Leu Phe Lys His Gln Pro Phe Arg
                325                 330                 335

Asp Ala Ile Lys Arg Ala Tyr Gln Leu Gly Ala Ile Asp Ser Asn Glu
            340                 345                 350

Ile Val Glu Ala Glu Val Asp Glu Leu Ile Asn Ser Lys Val Glu Lys
        355                 360                 365

Phe Lys Ser Pro Glu Ser Lys Ser Lys Ser Ala Ala Asp Leu Glu Thr
    370                 375                 380

Asp Leu Glu Gln Leu Ser Asp Met Glu Glu Phe Asn Glu
385                 390                 395


<210> SEQ ID NO 34
<211> LENGTH: 143
<212> TYPE: PRT
<213> ORGANISM: Artificial Sequence
<220> FEATURE:
<223> OTHER INFORMATION: Synthetic: Phage_T4_uvsY

<400> SEQUENCE: 34

Met His His His His His His Arg Leu Glu Asp Leu Gln Glu Glu Leu
1               5                   10                  15

Lys Lys Asp Val Phe Ile Asp Ser Thr Lys Leu Gln Tyr Glu Ala Ala
            20                  25                  30

Asn Asn Val Met Leu Tyr Ser Lys Trp Leu Asn Lys His Ser Ser Ile
        35                  40                  45

Lys Lys Glu Met Leu Arg Ile Glu Ala Gln Lys Lys Val Ala Leu Lys
    50                  55                  60

Ala Arg Leu Asp Tyr Tyr Ser Gly Arg Gly Asp Gly Asp Glu Phe Ser
65                  70                  75                  80

Met Asp Arg Tyr Glu Lys Ser Glu Met Lys Thr Val Leu Ser Ala Asp
                85                  90                  95

Lys Asp Val Leu Lys Val Asp Thr Ser Leu Gln Tyr Trp Gly Ile Leu
            100                 105                 110

Leu Asp Phe Cys Ser Gly Ala Leu Asp Ala Ile Lys Ser Arg Gly Phe
        115                 120                 125

Ala Ile Lys His Ile Gln Asp Met Arg Ala Phe Glu Ala Gly Lys
```

130 135 140

<210> SEQ ID NO 35
<211> LENGTH: 306
<212> TYPE: PRT
<213> ORGANISM: Artificial Sequence
<220> FEATURE:
<223> OTHER INFORMATION: Synthetic: Phage_T4_GP32

<400> SEQUENCE: 35

Met His His His His His His Phe Lys Arg Lys Ser Thr Ala Glu Leu
1 5 10 15

Ala Ala Gln Met Ala Lys Leu Asn Gly Asn Lys Gly Phe Ser Ser Glu
20 25 30

Asp Lys Gly Glu Trp Lys Leu Lys Leu Asp Asn Ala Gly Asn Gly Gln
35 40 45

Ala Val Ile Arg Phe Leu Pro Ser Lys Asn Asp Glu Gln Ala Pro Phe
50 55 60

Ala Ile Leu Val Asn His Gly Phe Lys Lys Asn Gly Lys Trp Tyr Ile
65 70 75 80

Glu Thr Cys Ser Ser Thr His Gly Asp Tyr Asp Ser Cys Pro Val Cys
85 90 95

Gln Tyr Ile Ser Lys Asn Asp Leu Tyr Asn Thr Asp Asn Lys Glu Tyr
100 105 110

Ser Leu Val Lys Arg Lys Thr Ser Tyr Trp Ala Asn Ile Leu Val Val
115 120 125

Lys Asp Pro Ala Ala Pro Glu Asn Glu Gly Lys Val Phe Lys Tyr Arg
130 135 140

Phe Gly Lys Lys Ile Trp Asp Lys Ile Asn Ala Met Ile Ala Val Asp
145 150 155 160

Val Glu Met Gly Glu Thr Pro Val Asp Val Thr Cys Pro Trp Glu Gly
165 170 175

Ala Asn Phe Val Leu Lys Val Lys Gln Val Ser Gly Phe Ser Asn Tyr
180 185 190

Asp Glu Ser Lys Phe Leu Asn Gln Ser Ala Ile Pro Asn Ile Asp Asp
195 200 205

Glu Ser Phe Gln Lys Glu Leu Phe Glu Gln Met Val Asp Leu Ser Glu
210 215 220

Met Thr Ser Lys Asp Lys Phe Lys Ser Phe Glu Glu Leu Asn Thr Lys
225 230 235 240

Phe Gly Gln Val Met Gly Thr Ala Val Met Gly Gly Ala Ala Ala Thr
245 250 255

Ala Ala Lys Lys Ala Asp Lys Val Ala Asp Asp Leu Asp Ala Phe Asn
260 265 270

Val Asp Asp Phe Asn Thr Lys Thr Glu Asp Asp Phe Met Ser Ser Ser
275 280 285

Ser Gly Ser Ser Ser Ser Ala Asp Asp Thr Asp Leu Asp Asp Leu Leu
290 295 300

Asn Asp
305

<210> SEQ ID NO 36
<211> LENGTH: 387
<212> TYPE: PRT
<213> ORGANISM: Artificial Sequence
<220> FEATURE:
<223> OTHER INFORMATION: Synthetic: RM-CK

<400> SEQUENCE: 36

Met His His His His His His Pro Phe Gly Asn Thr His Asn Lys Tyr
1 5 10 15

Lys Leu Asn Tyr Lys Ser Glu Glu Glu Tyr Pro Asp Leu Ser Lys His
20 25 30

Asn Asn His Met Ala Lys Val Leu Thr Pro Asp Leu Tyr Lys Lys Leu
35 40 45

Arg Asp Lys Glu Thr Pro Ser Gly Phe Thr Leu Asp Asp Val Ile Gln
50 55 60

Thr Gly Val Asp Asn Pro Gly His Pro Phe Ile Met Thr Val Gly Cys
65 70 75 80

Val Ala Gly Asp Glu Glu Ser Tyr Thr Val Phe Lys Asp Leu Phe Asp
85 90 95

Pro Ile Ile Gln Asp Arg His Gly Gly Phe Lys Pro Thr Asp Lys His
100 105 110

Lys Thr Asp Leu Asn His Glu Asn Leu Lys Gly Gly Asp Asp Leu Asp
115 120 125

Pro His Tyr Val Leu Ser Ser Arg Val Arg Thr Gly Arg Ser Ile Lys
130 135 140

Gly Tyr Thr Leu Pro Pro His Cys Ser Arg Gly Glu Arg Arg Ala Val
145 150 155 160

Glu Lys Leu Ser Val Glu Ala Leu Asn Ser Leu Thr Gly Glu Phe Lys
165 170 175

Gly Lys Tyr Tyr Pro Leu Lys Ser Met Thr Glu Gln Glu Gln Gln Gln
180 185 190

Leu Ile Asp Asp His Phe Leu Phe Asp Lys Pro Val Ser Pro Leu Leu
195 200 205

Leu Ala Ser Gly Met Ala Arg Asp Trp Pro Asp Ala Arg Gly Ile Trp
210 215 220

His Asn Asp Asn Lys Ser Phe Leu Val Trp Val Asn Glu Glu Asp His
225 230 235 240

Leu Arg Val Ile Ser Met Glu Lys Gly Gly Asn Met Lys Glu Val Phe
245 250 255

Arg Arg Phe Cys Val Gly Leu Gln Lys Ile Glu Glu Ile Phe Lys Lys
260 265 270

Ala Gly His Pro Phe Met Trp Asn Glu His Leu Gly Tyr Val Leu Thr
275 280 285

Cys Pro Ser Asn Leu Gly Thr Gly Leu Arg Gly Gly Val His Val Lys
290 295 300

Leu Ala His Leu Ser Lys His Pro Lys Phe Glu Glu Ile Leu Thr Arg
305 310 315 320

Leu Arg Leu Gln Lys Arg Gly Thr Gly Gly Val Asp Thr Ala Ala Val
325 330 335

Gly Ser Val Phe Asp Ile Ser Asn Ala Asp Arg Leu Gly Ser Ser Glu
340 345 350

Val Glu Gln Val Gln Leu Val Val Asp Gly Val Lys Leu Met Val Glu
355 360 365

Met Glu Lys Lys Leu Glu Lys Gly Gln Ser Ile Asp Asp Met Ile Pro
370 375 380

Ala Gln Lys
385

<210> SEQ ID NO 37
<211> LENGTH: 387
<212> TYPE: PRT
<213> ORGANISM: Artificial Sequence
<220> FEATURE:
<223> OTHER INFORMATION: Synthetic: RM-CK_G268N

<400> SEQUENCE: 37

```
Met His His His His His His Pro Phe Gly Asn Thr His Asn Lys Tyr
1               5                   10                  15

Lys Leu Asn Tyr Lys Ser Glu Glu Glu Tyr Pro Asp Leu Ser Lys His
            20                  25                  30

Asn Asn His Met Ala Lys Val Leu Thr Pro Asp Leu Tyr Lys Lys Leu
        35                  40                  45

Arg Asp Lys Glu Thr Pro Ser Gly Phe Thr Leu Asp Asp Val Ile Gln
    50                  55                  60

Thr Gly Val Asp Asn Pro Gly His Pro Phe Ile Met Thr Val Gly Cys
65                  70                  75                  80

Val Ala Gly Asp Glu Glu Ser Tyr Thr Val Phe Lys Asp Leu Phe Asp
                85                  90                  95

Pro Ile Ile Gln Asp Arg His Gly Gly Phe Lys Pro Thr Asp Lys His
            100                 105                 110

Lys Thr Asp Leu Asn His Glu Asn Leu Lys Gly Gly Asp Asp Leu Asp
        115                 120                 125

Pro His Tyr Val Leu Ser Ser Arg Val Arg Thr Gly Arg Ser Ile Lys
    130                 135                 140

Gly Tyr Thr Leu Pro Pro His Cys Ser Arg Gly Glu Arg Arg Ala Val
145                 150                 155                 160

Glu Lys Leu Ser Val Glu Ala Leu Asn Ser Leu Thr Gly Glu Phe Lys
                165                 170                 175

Gly Lys Tyr Tyr Pro Leu Lys Ser Met Thr Glu Gln Glu Gln Gln Gln
            180                 185                 190

Leu Ile Asp Asp His Phe Leu Phe Asp Lys Pro Val Ser Pro Leu Leu
        195                 200                 205

Leu Ala Ser Gly Met Ala Arg Asp Trp Pro Asp Ala Arg Gly Ile Trp
    210                 215                 220

His Asn Asp Asn Lys Ser Phe Leu Val Trp Val Asn Glu Glu Asp His
225                 230                 235                 240

Leu Arg Val Ile Ser Met Glu Lys Gly Gly Asn Met Lys Glu Val Phe
                245                 250                 255

Arg Arg Phe Cys Val Gly Leu Gln Lys Ile Glu Glu Ile Phe Lys Lys
            260                 265                 270

Ala Asn His Pro Phe Met Trp Asn Glu His Leu Gly Tyr Val Leu Thr
        275                 280                 285

Cys Pro Ser Asn Leu Gly Thr Gly Leu Arg Gly Gly Val His Val Lys
    290                 295                 300

Leu Ala His Leu Ser Lys His Pro Lys Phe Glu Glu Ile Leu Thr Arg
305                 310                 315                 320

Leu Arg Leu Gln Lys Arg Gly Thr Gly Gly Val Asp Thr Ala Ala Val
                325                 330                 335

Gly Ser Val Phe Asp Ile Ser Asn Ala Asp Arg Leu Gly Ser Ser Glu
            340                 345                 350

Val Glu Gln Val Gln Leu Val Val Asp Gly Val Lys Leu Met Val Glu
        355                 360                 365

Met Glu Lys Lys Leu Glu Lys Gly Gln Ser Ile Asp Asp Met Ile Pro
```

370 375 380

Ala Gln Lys
385

<210> SEQ ID NO 38
<211> LENGTH: 387
<212> TYPE: PRT
<213> ORGANISM: Artificial Sequence
<220> FEATURE:
<223> OTHER INFORMATION: Synthetic: Carp-M1-CK

<400> SEQUENCE: 38

Met His His His His His His Pro Phe Gly Asn Thr His Asn Asn Phe
1 5 10 15

Lys Leu Asn Tyr Ser Val Asp Asp Glu Phe Pro Asp Leu Ala Lys His
20 25 30

Asn Asn His Met Ala Lys Val Leu Thr Lys Glu Met Tyr Gly Lys Leu
35 40 45

Arg Asp Lys Gln Thr Ser Thr Gly Phe Thr Leu Asp Asp Ala Ile Gln
50 55 60

Thr Gly Val Asp Asn Pro Gly His Pro Phe Ile Met Thr Val Gly Cys
65 70 75 80

Val Ala Gly Asp Glu Glu Ser Tyr Glu Val Phe Lys Asp Leu Phe Asp
85 90 95

Pro Val Ile Ser Asp Arg His Gly Gly Tyr Lys Ala Thr Asp Lys His
100 105 110

Lys Thr Asp Leu Asn Phe Glu Asn Leu Lys Gly Gly Asp Asp Leu Asp
115 120 125

Pro Asn Tyr Val Leu Ser Ser Arg Val Arg Thr Gly Arg Ser Ile Lys
130 135 140

Gly Tyr Ala Leu Pro Pro His Asn Ser Arg Gly Glu Arg Arg Ala Val
145 150 155 160

Glu Lys Leu Ser Val Glu Ala Leu Asn Ser Leu Asp Gly Glu Phe Lys
165 170 175

Gly Lys Tyr Tyr Pro Leu Lys Ser Met Thr Asp Ala Glu Gln Glu Gln
180 185 190

Leu Ile Ala Asp His Phe Leu Phe Asp Lys Pro Val Ser Pro Leu Leu
195 200 205

Leu Ala Ala Gly Met Ala Arg Asp Trp Pro Asp Ala Arg Gly Ile Trp
210 215 220

His Asn Glu Asn Lys Thr Phe Leu Val Trp Val Asn Glu Glu Asp His
225 230 235 240

Leu Arg Val Ile Ser Met Gln Pro Gly Gly Asn Met Lys Glu Val Phe
245 250 255

Arg Arg Phe Cys Val Gly Leu Gln Arg Ile Glu Glu Ile Phe Lys Lys
260 265 270

His Asn His Gly Phe Met Trp Asn Glu His Leu Gly Phe Ile Leu Thr
275 280 285

Cys Pro Ser Asn Leu Gly Thr Gly Leu Arg Gly Gly Val His Val Lys
290 295 300

Leu Pro Lys Leu Ser Thr His Ala Lys Phe Asp Glu Ile Leu Thr Arg
305 310 315 320

Leu Arg Leu Gln Lys Arg Gly Thr Gly Gly Val Asp Thr Ala Ser Val
325 330 335

Gly Gly Val Phe Asp Ile Ser Asn Ala Asp Arg Ile Gly Ser Ser Glu 340 345 350

Val Asp Gln Val Gln Cys Val Val Asp Gly Val Lys Leu Met Ile Glu
355 360 365

Met Glu Lys Lys Leu Glu Lys Gly Glu Ser Ile Asp Ser Met Ile Pro
370 375 380

Ala Gln Lys
385

<210> SEQ ID NO 39
<211> LENGTH: 30
<212> TYPE: DNA
<213> ORGANISM: Artificial Sequence
<220> FEATURE:
<223> OTHER INFORMATION: Synthetic

<400> SEQUENCE: 39
gcgaacgggt gagtaacacg tatccaatct 30

<210> SEQ ID NO 40
<211> LENGTH: 32
<212> TYPE: DNA
<213> ORGANISM: Artificial Sequence
<220> FEATURE:
<223> OTHER INFORMATION: Synthetic

<400> SEQUENCE: 40
agccattacc tgctaaagtc attcttccca aa 32

<210> SEQ ID NO 41
<211> LENGTH: 29
<212> TYPE: DNA
<213> ORGANISM: Artificial Sequence
<220> FEATURE:
<223> OTHER INFORMATION: Synthetic

<400> SEQUENCE: 41
agcatgtggt ttaatttgat gttacgcgg 29

<210> SEQ ID NO 42
<211> LENGTH: 32
<212> TYPE: DNA
<213> ORGANISM: Artificial Sequence
<220> FEATURE:
<223> OTHER INFORMATION: Synthetic

<400> SEQUENCE: 42
ccatgcacca tctgtcactc cgttaacctc cg 32

<210> SEQ ID NO 43
<211> LENGTH: 39
<212> TYPE: DNA
<213> ORGANISM: Artificial Sequence
<220> FEATURE:
<223> OTHER INFORMATION: Synthetic

<400> SEQUENCE: 43
tgttacgcgg agaaccttac ccacgacatc cttcgcaat 39

<210> SEQ ID NO 44
<211> LENGTH: 32
<212> TYPE: DNA
<213> ORGANISM: Artificial Sequence
<220> FEATURE:
<223> OTHER INFORMATION: Synthetic

<400> SEQUENCE: 44
agagatcggg agcctaaatc tcccctcaat gg 32

<210> SEQ ID NO 45
<211> LENGTH: 34
<212> TYPE: DNA
<213> ORGANISM: Artificial Sequence
<220> FEATURE:
<223> OTHER INFORMATION: Synthetic

<400> SEQUENCE: 45
tcgagattgt gcggttatta atgagtcgtt tggg 34

<210> SEQ ID NO 46
<211> LENGTH: 43
<212> TYPE: DNA
<213> ORGANISM: Artificial Sequence
<220> FEATURE:
<223> OTHER INFORMATION: Synthetic

<400> SEQUENCE: 46
tgccacaact agatacatcc acatgattca ttacatcaat aat 43

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
gcgaacgggt gagtaacacg tatccaatct 30

<210> SEQ ID NO 48
<211> LENGTH: 32
<212> TYPE: DNA
<213> ORGANISM: Artificial Sequence
<220> FEATURE:
<223> OTHER INFORMATION: Synthetic

<400> SEQUENCE: 48
agccattacc tgctaaagtc attcttccca aa 32

<210> SEQ ID NO 49
<211> LENGTH: 568
<212> TYPE: DNA
<213> ORGANISM: Mycoplasma pneumoniae

<400> SEQUENCE: 49
aatactttag aggcgaacgg gtgagtaaca cgtatccaat ctaccttata atgggggata 60
actagttgaa agactagcta ataccgcata agaactttgg ttcgcatgaa tcaaagttga 120
aaggacctgc aagggttcgt tatttgatga gggtgcgcca tatcagctag ttggtggggt 180
aacggcctac caaggcaatg acgtgtagct atgctgagaa gtagaatagc cacaatggga 240
ctgagacacg gcccatactc ctacgggagg cagcagtagg gaatttttca caatgagcga 300
aagcttgatg gagcaatgcc gcgtgaacga tgaaggtctt taagattgta aagttctttt 360
atttgggaag aatgacttta gcaggtaatg gctagagttt gactgtacca ttttgaataa 420
gtgacgacta actatgtgcc agcagtcgcg gtaatacata ggtcgcaagc gttatccgga 480
tttattgggc gtaaagcaag cgcaggcgga ttgaaaagtc tggtgttaaa ggcagctgct 540
taacagttgt atgcattgga aactatta 568

<210> SEQ ID NO 50
<211> LENGTH: 32
<212> TYPE: DNA
<213> ORGANISM: Artificial Sequence
<220> FEATURE:
<223> OTHER INFORMATION: Synthetic

<400> SEQUENCE: 50
agagatcggg agcctaaatc tcccctcaat gg 32

<210> SEQ ID NO 51
<211> LENGTH: 34
<212> TYPE: DNA
<213> ORGANISM: Artificial Sequence
<220> FEATURE:
<223> OTHER INFORMATION: Synthetic

<400> SEQUENCE: 51
tcgagattgt gcggttatta atgagtcgtt tggg 34

<210> SEQ ID NO 52
<211> LENGTH: 43
<212> TYPE: DNA
<213> ORGANISM: Artificial Sequence
<220> FEATURE:
<223> OTHER INFORMATION: Synthetic

<400> SEQUENCE: 52
tgccacaact agatacatcc acatgattca ttacatcaat aat 43

<210> SEQ ID NO 53
<211> LENGTH: 32
<212> TYPE: DNA
<213> ORGANISM: Artificial Sequence
<220> FEATURE:
<223> OTHER INFORMATION: Synthetic

<400> SEQUENCE: 53
cccacgccaa cgtcaagacc attcaagact cc 32

<210> SEQ ID NO 54
<211> LENGTH: 45
<212> TYPE: DNA
<213> ORGANISM: Artificial Sequence
<220> FEATURE:
<223> OTHER INFORMATION: Synthetic

<400> SEQUENCE: 54
caaatgaagc cattcgctca ttagtcgaag gacaaagcgc agacc 45

<210> SEQ ID NO 55
<211> LENGTH: 32
<212> TYPE: DNA
<213> ORGANISM: Artificial Sequence
<220> FEATURE:
<223> OTHER INFORMATION: Synthetic

<400> SEQUENCE: 55
tccaattcgt gatagtctac agtacggcta cc 32

<210> SEQ ID NO 56
<211> LENGTH: 855
<212> TYPE: DNA
<213> ORGANISM: Grass Carp Reovirus
<220> FEATURE:

<221> NAME/KEY: misc_feature
<223> OTHER INFORMATION: Grass Carp Reovirus GCRV VP7

<400> SEQUENCE: 56
attctagcta gcatgccact tcacatgatt ccgcaagtcg cccacgctat ggtgcgtgca 60
gccgctgcag gacgccttac cttatacaca agaactagaa ctgagaccac caactttgat 120
cacgctgagt acgtcacctg cgggcggtac accatctgcg ccttctgcct tacgactctg 180
gctccccacg ccaacgtcaa gaccattcaa gactcccacg cttgttcacg tcaaccaaat 240
gaagccattc gctcattagt cgaagtgagt gacaaagcgc agaccgccct cgtcggtagc 300
cgtactgtag actatcacga attggatgtg aaagctgggt tcgtcgcccc aactgccgat 360
gaaacaatag ccccctctaa ggatatcgtc gaacttccgt ttcgcacctg tgacttgtac 420
gattcctctg ctaccgcttg cgtccgaaat cactgccagg ccggtcacga cggcgttatc 480
cacctcccga tcctttctgg agatttcaaa ttgcctaacg agcatcccac caaaccgttg 540
gacgatacgc atccccacga caaggtgctg actcgctgcc ccaagactgg tctcctcctc 600
gtccatgaca ctcacgcaca cgccaccgcc gtagttgcca ccgctgctac gagagctatc 660
ctcatgcacg acctccttac atcagcgaac gcggatgacg gccatcaagc acgttccgct 720
tgctacggtc cagcgtttaa caacctgacc ttcgcttgcc actccacctg tgcttcagat 780
atggctcact tcgactgcgg ccagatcgtt ggactcgact tgcatgtgga gccatccgat 840
taactcgagc ggaat 855

<210> SEQ ID NO 57
<211> LENGTH: 30
<212> TYPE: DNA
<213> ORGANISM: Artificial Sequence
<220> FEATURE:
<223> OTHER INFORMATION: Synthetic

<400> SEQUENCE: 57
gcgaacgggt gagtaacacg tatccaatct 30

<210> SEQ ID NO 58
<211> LENGTH: 30
<212> TYPE: DNA
<213> ORGANISM: Artificial Sequence
<220> FEATURE:
<223> OTHER INFORMATION: Synthetic

<400> SEQUENCE: 58
caaagttctt atgcggtatt agctagtctt 30

<210> SEQ ID NO 59
<211> LENGTH: 29
<212> TYPE: DNA
<213> ORGANISM: Artificial Sequence
<220> FEATURE:
<223> OTHER INFORMATION: Synthetic

<400> SEQUENCE: 59
agcatgtggt ttaatttgat gttacgcgg 29

<210> SEQ ID NO 60
<211> LENGTH: 32
<212> TYPE: DNA
<213> ORGANISM: Artificial Sequence
<220> FEATURE:
<223> OTHER INFORMATION: Synthetic

```
<400> SEQUENCE: 60

ccatgcacca tctgtcactc cgttaacctc cg                                32


<210> SEQ ID NO 61
<211> LENGTH: 398
<212> TYPE: PRT
<213> ORGANISM: Unknown
<220> FEATURE:
<223> OTHER INFORMATION: VR7_uvsX
<220> FEATURE:
<221> NAME/KEY: misc_feature
<222> LOCATION: (70)..(70)
<223> OTHER INFORMATION: Xaa can be any naturally occurring amino acid

<400> SEQUENCE: 61

Met Ser Ile Ala Asp Leu Lys Ser Arg Leu Ile Lys Ala Ser Thr Ser
1               5                   10                  15

Lys Met Thr Ala Thr Leu Lys Ser Lys Phe Phe Asn Asp Lys Asp Val
            20                  25                  30

Val Arg Thr Lys Ile Pro Met Leu Asn Ile Ala Ile Ser Gly Ala Leu
        35                  40                  45

Asp Gly Gly Met Gln Ser Gly Leu Thr Ile Phe Ala Gly Pro Ser Lys
    50                  55                  60

His Phe Lys Ser Asn Xaa Gly Leu Thr Met Val Ser Ala Tyr Met Asn
65                  70                  75                  80

Lys Pro Glu Ala Ile Cys Leu Phe Tyr Asp Ser Glu Phe Gly Ile Thr
                85                  90                  95

Glu Ala Tyr Leu Arg Ala Met Lys Val Asp Pro Glu Arg Val Ile His
            100                 105                 110

Thr Pro Ile Gln Ser Val Glu Gln Leu Lys Val Asp Met Val Asn Gln
        115                 120                 125

Leu Glu Ala Ile Glu Arg Gly Glu Lys Val Ile Ile Phe Ile Asp Ser
    130                 135                 140

Ile Gly Asn Met Ala Ser Lys Lys Glu Thr Glu Asp Ala Leu Asn Glu
145                 150                 155                 160

Lys Val Val Gly Asp Met Thr Arg Ala Lys Ser Leu Lys Ser Leu Phe
                165                 170                 175

Arg Ile Val Thr Pro Phe Phe Ser Ile Lys Asp Ile Pro Cys Val Ala
            180                 185                 190

Val Asn His Thr Ile Glu Thr Ile Glu Met Tyr Ser Lys Thr Thr Val
        195                 200                 205

Met Thr Gly Gly Thr Gly Val Met Tyr Ser Ala Asp Thr Val Phe Ile
    210                 215                 220

Ile Gly Lys Arg Gln Ile Lys Glu Thr Gly Lys Glu Leu Glu Gly Phe
225                 230                 235                 240

Gln Phe Val Leu Asn Ala Glu Lys Ser Arg Met Val Lys Glu Lys Ser
                245                 250                 255

Lys Phe Phe Ile Asp Val Lys Phe Asp Gly Gly Ile Asp Val Lys Phe
            260                 265                 270

Asp Gly Gly Ile Asp Pro Tyr Ser Gly Leu Leu Asp Met Ala Met Glu
        275                 280                 285

Ile Gly Phe Val Val Lys Pro Val Gly Trp Tyr Asn Arg Glu Tyr Leu
    290                 295                 300

Asp Val Glu Thr Gly Glu Met Val Arg Glu Glu Lys Ser Trp Arg Ala
305                 310                 315                 320

Lys Asp Thr Asn Cys Thr Glu Phe Trp Gly Pro Leu Phe Lys His Glu
```

```
                325                 330                 335

Pro Phe Arg Asp Ala Ile Lys Arg His Tyr Gln Leu Gly Ala Ile Asp
            340                 345                 350

Ser Asn Ala Val Val Asp Ala Glu Val Asp Glu Leu Ile Ala Ser Lys
        355                 360                 365

Val Glu Lys Tyr Ser Ala Pro Val Gly Lys Thr Lys Pro Ser Ala Ala
    370                 375                 380

Asp Ile Glu Asn Asp Leu Asp Met Met Glu Asp Leu Asp Glu
385                 390                 395


<210> SEQ ID NO 62
<211> LENGTH: 388
<212> TYPE: PRT
<213> ORGANISM: Unknown
<220> FEATURE:
<223> OTHER INFORMATION: VR5_uvsX

<400> SEQUENCE: 62

Met Ser Asp Leu Lys Ser Arg Leu Ile Lys Ala Ser Thr Ser Lys Met
1               5                   10                  15

Thr Ala Asp Leu Thr Lys Ser Lys Leu Phe Asn Gly Arg Asp Glu Val
            20                  25                  30

Pro Thr Arg Ile Pro Met Leu Asn Ile Ala Leu Gly Gly Ala Leu Asn
        35                  40                  45

Ala Gly Leu Gln Ser Gly Leu Thr Ile Phe Ala Ala Pro Ser Lys His
    50                  55                  60

Phe Lys Thr Leu Phe Gly Leu Thr Met Val Ala Ala Tyr Met Lys Lys
65                  70                  75                  80

Tyr Pro Asp Ala Ile Cys Leu Phe Tyr Asp Ser Glu Phe Gly Ala Ser
                85                  90                  95

Glu Ser Tyr Phe Arg Ser Met Gly Val Asp Leu Glu Arg Val Val His
            100                 105                 110

Thr Pro Ile Gln Ser Val Glu Gln Leu Lys Val Asp Met Thr Asn Gln
        115                 120                 125

Leu Glu Glu Ile Thr Arg Gly Glu Lys Val Ile Ile Phe Ile Asp Ser
    130                 135                 140

Gly Asn Thr Ala Ser Lys Lys Glu Thr Glu Asp Ala Leu Asn Glu Lys
145                 150                 155                 160

Val Val Gly Asp Met Thr Arg Ala Lys Ser Leu Lys Ser Leu Phe Arg
                165                 170                 175

Ile Val Thr Pro Tyr Leu Thr Ile Lys Asp Ile Pro Cys Val Ala Ile
            180                 185                 190

Asn His Thr Ala Met Glu Ile Gly Gly Met Tyr Pro Lys Glu Ile Met
        195                 200                 205

Gly Gly Gly Thr Gly Ile Leu Tyr Ser Ala Ser Thr Val Phe Phe Ile
    210                 215                 220

Ser Lys Arg Gln Val Lys Asp Gly Thr Glu Leu Thr Gly Tyr Asp Phe
225                 230                 235                 240

Thr Leu Lys Ala Glu Lys Ser Arg Thr Val Lys Glu Lys Ser Thr Phe
                245                 250                 255

Pro Ile Thr Val Asn Phe Glu Gly Gly Ile Asp Pro Phe Ser Gly Leu
            260                 265                 270

Leu Glu Met Ala Thr Glu Ile Gly Phe Val Val Lys Pro Lys Ala Gly
        275                 280                 285

Trp Tyr Asn Arg Ala Phe Leu Asp Glu Thr Thr Gly Glu Met Val Gln
```

```
    290                 295                 300

Glu Glu Lys Ser Trp Arg Ala Lys Ala Thr Asp Cys Val Glu Phe Trp
305                 310                 315                 320

Gly Pro Leu Phe Lys His Ala Pro Phe Arg Ala Ala Ile Glu Asn Lys
                325                 330                 335

Tyr Lys Leu Gly Ala Ile Asn Ser Ile Lys Glu Val Asp Asp Ala Val
            340                 345                 350

Asn Asp Leu Ile Asn Ser Arg Val Ser Lys Asn Val Ala Val Lys Ser
        355                 360                 365

Gly Asp Ala Gln Ser Ala Ala Asp Ile Glu Asn Asp Leu Glu Glu Met
    370                 375                 380

Asp Leu Asn Asp
385


<210> SEQ ID NO 63
<211> LENGTH: 391
<212> TYPE: PRT
<213> ORGANISM: Unknown
<220> FEATURE:
<223> OTHER INFORMATION: T6_uvsX

<400> SEQUENCE: 63

Met Ser Ile Ala Asp Leu Lys Ser Arg Leu Ile Lys Ala Ser Thr Ser
1               5                   10                  15

Lys Met Thr Ala Glu Leu Thr Thr Ser Lys Phe Phe Asn Glu Lys Asp
            20                  25                  30

Val Ile Arg Thr Lys Ile Pro Met Leu Asn Ile Ala Ile Ser Gly Ala
        35                  40                  45

Ile Asp Gly Gly Met Gln Ser Gly Leu Thr Ile Phe Ala Gly Pro Ser
    50                  55                  60

Lys Met Phe Lys Ser Asn Met Ser Leu Thr Met Val Ala Ala Tyr Leu
65                  70                  75                  80

Asn Lys Tyr Pro Asp Ala Val Cys Leu Phe Tyr Asp Ser Glu Phe Gly
                85                  90                  95

Ile Thr Pro Ala Tyr Leu Arg Ser Met Gly Val Asp Pro Glu Arg Val
            100                 105                 110

Ile His Thr Pro Ile Gln Ser Val Glu Gln Leu Lys Ile Asp Met Val
        115                 120                 125

Asn Gln Leu Glu Ala Ile Glu Arg Gly Lys Val Ile Val Phe Ile Asp
    130                 135                 140

Ser Ile Gly Asn Met Ala Ser Lys Lys Glu Thr Glu Asp Ala Leu Asn
145                 150                 155                 160

Glu Lys Ser Val Ala Asp Met Thr Arg Ala Lys Ser Leu Lys Ser Leu
                165                 170                 175

Phe Arg Ile Val Thr Pro Tyr Phe Ser Ile Lys Asn Ile Pro Cys Val
            180                 185                 190

Ala Val Asn His Thr Ile Glu Thr Ile Glu Met Phe Ser Lys Thr Val
        195                 200                 205

Met Thr Gly Gly Thr Gly Val Met Tyr Ser Ala Asp Thr Val Phe Ile
    210                 215                 220

Ile Gly Lys Arg Gln Ile Lys Asp Gly Ser Asp Leu Gln Gly Tyr Gln
225                 230                 235                 240

Phe Val Leu Asn Val Glu Lys Ser Thr Arg Val Lys Glu Lys Ser Lys
                245                 250                 255

Phe Phe Ile Asp Val Lys Phe Asp Gly Gly Ile Asp Pro Tyr Ser Gly
```

```
            260                 265                 270

Leu Leu Asp Met Ala Leu Glu Leu Gly Phe Val Val Lys Pro Lys Asn
        275                 280                 285

Gly Trp Tyr Ala Arg Glu Phe Leu Asp Glu Thr Thr Gly Glu Met Ile
    290                 295                 300

Arg Glu Glu Lys Ser Trp Arg Ala Lys Asp Thr Asn Cys Thr Thr Phe
305                 310                 315                 320

Trp Gly Pro Leu Phe Lys His Gln Pro Phe Arg Asp Ala Ile Lys Arg
                325                 330                 335

Ala Tyr Gln Leu Gly Ala Ile Asp Ser Asn Glu Ile Val Glu Ala Glu
            340                 345                 350

Val Asp Glu Leu Ile Asn Ser Lys Val Glu Lys Phe Lys Ser Pro Glu
        355                 360                 365

Ser Lys Ser Lys Ala Ala Asp Leu Glu Thr Asp Leu Glu Gln Leu Ser
    370                 375                 380

Asp Met Glu Glu Phe Asn Glu
385                 390


<210> SEQ ID NO 64
<211> LENGTH: 388
<212> TYPE: PRT
<213> ORGANISM: Unknown
<220> FEATURE:
<223> OTHER INFORMATION: RB69_uvsX

<400> SEQUENCE: 64

Met Ser Asp Leu Lys Ser Arg Leu Ile Lys Ala Ser Thr Ser Lys Met
1               5                   10                  15

Thr Ala Asp Leu Thr Lys Ser Lys Leu Phe Asn Asn Arg Asp Glu Val
            20                  25                  30

Pro Thr Arg Ile Pro Met Leu Asn Ile Ala Leu Gly Gly Ala Leu Asn
        35                  40                  45

Ala Gly Leu Gln Ser Gly Leu Thr Ile Phe Ala Ala Pro Ser Lys His
    50                  55                  60

Phe Lys Thr Leu Phe Gly Leu Thr Met Val Ala Ala Tyr Met Lys Lys
65                  70                  75                  80

Tyr Lys Asp Ala Ile Cys Leu Phe Tyr Asp Ser Glu Phe Gly Ala Ser
                85                  90                  95

Glu Ser Tyr Phe Arg Ser Met Gly Val Asp Leu Asp Arg Val Val His
            100                 105                 110

Thr Pro Ile Gln Ser Val Glu Leu Lys Val Asp Met Thr Asn Gln Leu
        115                 120                 125

Asp Ala Ile Glu Arg Gly Asp Lys Val Ile Ile Phe Ile Asp Ser Ile
    130                 135                 140

Gly Asn Thr Ala Ser Lys Lys Glu Thr Glu Asp Ala Leu Asn Glu Lys
145                 150                 155                 160

Val Val Gly Asp Met Ser Arg Ala Lys Ala Leu Lys Ser Leu Phe Arg
                165                 170                 175

Ile Val Thr Pro Tyr Leu Thr Ile Lys Asp Ile Pro Cys Val Ala Ile
            180                 185                 190

Asn His Thr Ala Met Glu Ile Gly Gly Leu Tyr Pro Lys Glu Ile Met
        195                 200                 205

Gly Gly Gly Thr Gly Ile Leu Tyr Ser Ala Asn Thr Val Phe Phe Ile
    210                 215                 220

Ser Lys Arg Gln Val Lys Asp Gly Thr Glu Leu Thr Gly Tyr Asp Phe
```

```
225                 230                 235                 240

Thr Leu Lys Ala Glu Lys Ser Arg Thr Val Lys Glu Lys Ser Thr Phe
                245                 250                 255

Pro Ile Thr Val Asn Phe Asp Gly Gly Ile Asp Phe Ser Gly Leu Leu
            260                 265                 270

Glu Met Ala Thr Glu Ile Gly Phe Val Val Lys Pro Lys Ala Gly Trp
        275                 280                 285

Tyr Ala Arg Glu Phe Leu Asp Glu Glu Thr Gly Glu Met Ile Arg Glu
    290                 295                 300

Glu Lys Ser Trp Arg Ala Lys Ala Thr Asp Cys Val Glu Phe Trp Gly
305                 310                 315                 320

Pro Leu Phe Lys His Lys Pro Phe Arg Asp Ala Ile Glu Thr Lys Tyr
                325                 330                 335

Lys Leu Gly Ala Ile Ser Ser Ile Lys Glu Val Asp Asp Ala Val Asn
            340                 345                 350

Asp Leu Ile Asn Cys Lys Ala Thr Thr Lys Val Pro Val Lys Thr Ser
        355                 360                 365

Asp Ala Pro Ser Ala Ala Asp Ile Glu Asn Asp Leu Asp Glu Met Glu
    370                 375                 380

Asp Phe Asp Glu
385


<210> SEQ ID NO 65
<211> LENGTH: 386
<212> TYPE: PRT
<213> ORGANISM: Unknown
<220> FEATURE:
<223> OTHER INFORMATION: T4_uvsx

<400> SEQUENCE: 65

Met Ser Asp Leu Lys Ser Arg Leu Ile Lys Ala Ser Thr Ser Lys Leu
1               5                   10                  15

Thr Ala Glu Leu Thr Ala Ser Lys Phe Phe Asn Glu Lys Asp Val Val
            20                  25                  30

Arg Thr Lys Ile Pro Met Met Asn Ile Ala Leu Ser Gly Glu Ile Thr
        35                  40                  45

Gly Gly Met Gln Ser Gly Leu Leu Ile Leu Ala Gly Pro Ser Lys Ser
    50                  55                  60

Phe Lys Ser Asn Phe Gly Leu Thr Met Val Ser Ser Tyr Met Arg Gln
65                  70                  75                  80

Tyr Pro Asp Ala Val Cys Leu Phe Tyr Asp Ser Glu Phe Gly Ile Thr
                85                  90                  95

Pro Ala Tyr Leu Arg Ser Lys Met Gly Val Asp Pro Glu Arg Val Ile
            100                 105                 110

His Thr Pro Val Gln Ser Leu Arg Ile Asp Met Val Asn Gln Leu Asp
        115                 120                 125

Ala Ile Glu Arg Gly Glu Lys Val Val Val Phe Ile Asp Ser Leu Gly
    130                 135                 140

Asn Leu Ala Ser Lys Lys Glu Thr Glu Asp Ala Leu Asn Glu Lys Val
145                 150                 155                 160

Val Ser Asp Met Thr Arg Ala Lys Thr Met Lys Ser Leu Phe Arg Ile
                165                 170                 175

Val Thr Pro Tyr Ser Thr Lys Asn Ile Pro Cys Ile Ala Ile Asn His
            180                 185                 190

Thr Tyr Glu Thr Gln Glu Met Phe Ser Lys Thr Val Met Gly Gly Thr
```

-continued

```
        195                 200                 205

Gly Pro Met Tyr Ser Ala Asp Thr Val Phe Ile Ile Gly Lys Arg Gln
    210                 215                 220

Ile Lys Asp Gly Ser Asp Leu Gln Gly Tyr Gln Phe Val Leu Asn Glu
225                 230                 235                 240

Lys Ser Arg Thr Val Lys Glu Lys Ser Lys Phe Phe Ile Asp Val Lys
                245                 250                 255

Phe Asp Gly Gly Ile Asp Pro Tyr Ser Gly Leu Leu Asp Met Ala Leu
            260                 265                 270

Glu Leu Gly Phe Val Val Lys Pro Lys Asn Gly Trp Tyr Ala Arg Glu
        275                 280                 285

Phe Leu Asp Glu Glu Thr Gly Glu Met Ile Arg Glu Glu Lys Ser Trp
    290                 295                 300

Arg Ala Lys Asp Thr Asn Cys Thr Thr Phe Trp Gly Pro Leu Phe Lys
305                 310                 315                 320

His Gln Pro Phe Arg Asp Ala Ile Lys Arg Ala Tyr Gln Leu Gly Ala
                325                 330                 335

Ile Asp Ser Asn Glu Ile Val Glu Ala Glu Val Asp Glu Leu Ile Asn
            340                 345                 350

Ser Lys Val Glu Lys Phe Lys Ser Pro Glu Ser Lys Ser Lys Ser Ala
        355                 360                 365

Ala Asp Leu Glu Thr Asp Leu Glu Gln Leu Ser Asp Met Glu Glu Phe
    370                 375                 380

Asn Glu
385
```